US012577550B2

(12) United States Patent
Dong et al.

(10) Patent No.: US 12,577,550 B2
(45) Date of Patent: Mar. 17, 2026

(54) ENGINEERED BOTULINUM NEUROTOXIN

(71) Applicant: President and Fellows of Harvard College, Cambridge, MA (US)

(72) Inventors: Min Dong, Weatogue, CT (US); Lisheng Peng, Guangzhou (CN); Liang Tao, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 998 days.

(21) Appl. No.: 17/582,958

(22) Filed: Jan. 24, 2022

(65) Prior Publication Data

US 2022/0154160 A1    May 19, 2022

Related U.S. Application Data

(62) Division of application No. 15/561,355, filed as application No. PCT/US2016/024211 on Mar. 25, 2016, now Pat. No. 11,268,080.

(Continued)

(51) Int. Cl.
  *C12N 9/52*      (2006.01)
  *C07K 14/33*     (2006.01)
  (Continued)

(52) U.S. Cl.
  CPC .............. *C12N 9/52* (2013.01); *C07K 14/33* (2013.01); *C12N 15/1055* (2013.01);
  (Continued)

(58) Field of Classification Search
  CPC ...... C12N 9/52; C12N 15/1055; C07K 14/33; C07K 2319/50; C07K 2319/74;
  (Continued)

(56) References Cited

U.S. PATENT DOCUMENTS

| 4,518,584 A | 5/1985 | Mark et al. |
| 4,737,462 A | 4/1988 | Mark et al. |

(Continued)

FOREIGN PATENT DOCUMENTS

| CA | 2874587 A1 | 12/2013 |
| CN | 101184770 A | 5/2008 |

(Continued)

OTHER PUBLICATIONS

Puigbo P, Guzman E, Romeu A, Garcia-Vallve S. Optimizer: a web server for optimizing the codon usage of DNA sequences. Nucleic Acids Res. Jul. 2007;35(Web Server issue):W126-31. doi: 10.1093/nar/gkm219. Epub Apr. 16, 2007. PMID: 17439967; PMCID: PMC1933141. (Year: 2007).*

(Continued)

*Primary Examiner* — Robert B Mondesi
(74) *Attorney, Agent, or Firm* — Choate, Hall & Stewart LLP; Brenda Herschbach Jarrell; Stephanie L. Schonewald

(57) ABSTRACT

Disclosed herein is a botulinum neurotoxin (BoNT) polypeptide with a modified receptor binding domain (H$_C$) having one or more amino acid mutations that modify the binding of the BoNT to the receptor. Specific mutations and combinations of mutations are also disclosed. Isolated modified H$_C$ polypeptides comprising the modified H$_C$, chimeric molecules, pharmaceutical compositions, and methods of making and using the same are also disclosed. Methods of identifying additional such modified receptor binding domains, are further disclosed.

13 Claims, 32 Drawing Sheets

Specification includes a Sequence Listing.

Related U.S. Application Data

(60) Provisional application No. 62/138,818, filed on Mar. 26, 2015.

(51) Int. Cl.
  *C12N 15/10*          (2006.01)
  *A61K 38/00*          (2006.01)
(52) U.S. Cl.
  CPC ...... *C12Y 304/24069* (2013.01); *A61K 38/00* (2013.01); *C07K 2319/50* (2013.01); *C07K 2319/74* (2013.01); *G01N 2333/952* (2013.01)
(58) Field of Classification Search
  CPC ............ C12Y 304/24069; A61K 38/00; G01N 2333/952; Y02A 50/30; A61P 25/00
  USPC ...................................................... 424/94.67
  See application file for complete search history.

(56)                References Cited

U.S. PATENT DOCUMENTS

| | | | | |
|---|---|---|---|---|
| 5,053,005 | A | 10/1991 | Borodic et al. | |
| 5,714,468 | A | 2/1998 | Binder | |
| 5,721,215 | A | 2/1998 | Aoki et al. | |
| 5,766,605 | A | 6/1998 | Sanders et al. | |
| 5,989,545 | A | 11/1999 | Foster et al. | |
| 6,113,915 | A | 9/2000 | Aoki et al. | |
| 6,967,088 | B1 | 11/2005 | Williams et al. | |
| 7,189,541 | B2 | 3/2007 | Donovan | |
| 7,514,088 | B2 | 4/2009 | Steward et al. | |
| 7,645,570 | B2 | 1/2010 | Fernandez-Salas et al. | |
| 7,985,554 | B2 | 7/2011 | Chapman et al. | |
| 8,052,979 | B2 | 11/2011 | Steward et al. | |
| 8,445,650 | B2 | 5/2013 | Simpson et al. | |
| 8,476,024 | B2 | 7/2013 | Mahrhold et al. | |
| 8,481,040 | B2 | 7/2013 | Rummel et al. | |
| 8,586,081 | B2 | 11/2013 | Singh et al. | |
| 8,841,111 | B2 | 9/2014 | Steward et al. | |
| 9,598,685 | B2 * | 3/2017 | Dong ...................... A61P 43/00 | |
| 10,030,238 | B2 | 7/2018 | Cossins et al. | |
| 10,190,110 | B2 * | 1/2019 | Dong ...................... A61P 21/02 | |
| 10,266,816 | B2 | 4/2019 | Rummel et al. | |
| 10,457,927 | B2 | 10/2019 | Dolly et al. | |
| 10,844,362 | B2 | 11/2020 | Dong et al. | |
| 10,883,096 | B2 | 1/2021 | Rummel et al. | |
| 11,104,891 | B2 | 8/2021 | Dong et al. | |
| 11,117,935 | B2 | 9/2021 | Dong et al. | |
| 2004/0013687 | A1 | 1/2004 | Simpson et al. | |
| 2006/0211619 | A1 | 9/2006 | Steward et al. | |
| 2007/0166332 | A1 | 7/2007 | Steward et al. | |
| 2007/0299008 | A1 | 12/2007 | Rummel | |
| 2008/0032931 | A1 | 2/2008 | Steward et al. | |
| 2009/0023901 | A1 | 1/2009 | Steward et al. | |
| 2009/0311275 | A1 | 12/2009 | Rummel et al. | |
| 2011/0171226 | A1 | 7/2011 | Johnson et al. | |
| 2011/0189158 | A1 | 8/2011 | Frevert | |
| 2012/0039941 | A1 | 2/2012 | Barbieri et al. | |
| 2012/0178140 | A1 | 7/2012 | Steward et al. | |
| 2015/0166972 | A1 | 6/2015 | Dong et al. | |
| 2017/0226496 | A1 | 8/2017 | Dong et al. | |
| 2018/0080016 | A1 | 3/2018 | Dong et al. | |
| 2019/0127427 | A1 | 5/2019 | Liu | |
| 2019/0185524 | A1 | 6/2019 | Dong et al. | |
| 2019/0256834 | A1 | 8/2019 | Dong et al. | |
| 2022/0033447 | A1 | 2/2022 | Dong et al. | |

FOREIGN PATENT DOCUMENTS

| | | | |
|---|---|---|---|
| CN | 101903035 | A | 12/2010 |
| CN | 101918021 | A | 12/2010 |
| CN | 102131823 | A | 7/2011 |
| CN | 102481351 | A | 5/2012 |
| CN | 104736166 | A | 6/2015 |
| JP | 2008-538902 | A | 11/2008 |

| | | | | | |
|---|---|---|---|---|---|
| KR | 10-2008-0014754 | A | 2/2008 | | |
| WO | WO-95/32738 | A1 | 12/1995 | | |
| WO | WO-95/33850 | A1 | 12/1995 | | |
| WO | WO-96/33273 | A1 | 10/1996 | | |
| WO | WO-98/07864 | A1 | 2/1998 | | |
| WO | WO-1998/008540 | A1 | 3/1998 | | |
| WO | WO-99/17806 | A1 | 4/1999 | | |
| WO | WO-2006/001676 | A1 | 1/2006 | | |
| WO | WO-2006/114308 | A3 | 11/2006 | | |
| WO | WO-2007/144493 | A2 | 12/2007 | | |
| WO | WO-2008/059126 | A1 | 5/2008 | | |
| WO | WO-2008/090287 | A2 | 7/2008 | | |
| WO | WO-2009/014854 | A1 | 1/2009 | | |
| WO | WO-2009/015840 | A2 | 2/2009 | | |
| WO | WO-2009/038770 | A2 | 3/2009 | | |
| WO | WO-2009/055350 | A1 | 4/2009 | | |
| WO | WO-2009/055351 | A1 | 4/2009 | | |
| WO | WO-2009/130600 | A2 | 10/2009 | | |
| WO | WO-2013/180799 | A1 | 12/2013 | | |
| WO | WO-2013180799 | A9 * | 12/2014 | ............ | A61K 38/00 |
| WO | WO-2016/154534 | A1 | 9/2016 | | |
| WO | WO-2017/214447 | A1 | 12/2017 | | |
| WO | WO-2018/039506 | A1 | 3/2018 | | |

OTHER PUBLICATIONS

Aoki, K. Roger, Botulinum toxin: A Successful Therapeutic Protein, Curr Med Chem, 11: 3085-3092 (2004).

Arnau, J. et al., Current strategies for the use of affinity tags and tag removal for the purification of recombinant proteins, Protein expression and purification, 48(1):1-13 (2006).

Arnon et al., Botulinum Toxin as a Biological Weapon: Medical and Public Health Management, Jama, 285: 1059-1070 (2001).

Atassi et al., Immune recognition of BoNTs A and B: how anti-toxin antibodies that bind to the heavy chain obstruct toxin action, Toxicon, 54(5): 600-613 (2009).

Atassi et al., Molecular immune recognition of botulinum neurotoxin B. The light chain regions that bind human blocking antibodies from toxin-treated cervical dystonia patients. Antigenic structure of the entire BoNT/B molecule, Immunobiol, 217: 17-27 (2012).

Atassi et al., Molecular recognition of botulinum neurotoxin B heavy chain by human antibodies from cervical dystonia patients that develop immunoresistance to toxin treatment, Mol Immunol, 45(15): 3878-3888 (2008).

Bauer, C. et al., A genetic enrichment for mutations constructed by oligodeoxynucleotide-directed mutagenesis, Gene, 37(1-3):73-81 (1985).

Benoit, R. et al., Structural basis for recognition of synaptic vesicle protein 2C by botulinum neurotoxin A, Nature, 505(7481):108-11 (2014).

Berntsson, R. et al., Crystal structures of botulinum neurotoxin DC in complex with its protein receptors synaptotagmin I and II, Structure, 21(9):1602-11 (2013).

Berntsson, R. et al., Structure of dual receptor binding to botulinum neurotoxin B, Nature Communications, 4 (2013).

Berry, M.J. et al., Substitution of cystein for selenocysteine in type I iodothyronine deiodinase reduces the catalytic efficiency of the protein but enhances its translation, Endocrinology, 131(4):1848-1852 (1992).

Binz, T., et al., Clostridial neurotoxins: mechanism of SNARE cleavage and outlook on potential substrate specificity reengineering, Toxins (Basel), 2(4):665-82 (2010).

Blasi, J. et al., Botulinum neurotoxin A selectively cleaves the synaptic protein SNAP-25, Nature, 365(6442):160-3 (1993).

Bonventre P. and Kempe, L., Physiology of toxin production by Clostridium botulinum types A and B. III. Effect of pH and temperature during incubation on growth, autolysis, and toxin production, Appl Microbiol., 7:374-7 (1959).

Bonventre, P. and Kempe, L., Physiology of toxin production by Clostridium botulinum types A and B. IV. Activation of the toxin, J. Bacteriol, 79(1):24-32 (1960).

Brin et al., Safety and efficacy of NeuroBloc (botulinum toxin type B) in type A-resistant cervical dystonia, Neurology, 53: 1431-1438 (1999).

(56)     References Cited

OTHER PUBLICATIONS

Brodsky, M. et al., Diffusion of botulinum toxins, Tremor Other Hyperkinet Mov (NY), 7 pages (2012).

Chai et al., Structural basis of cell surface receptor recognition by botulinum neurotoxin B, Nature, 444(7122):1096-1100 (2006).

Chapman et al., Comparison of Botulinum Neurotoxin Preparations for the Treatment of Cervical Dystonia, Clin Ther, 29: 1325-1337 (2007).

Chen, S. and Barbieri, J., Engineering botulinum neurotoxin to extend therapeutic intervention, Proc Natl Acad Sci USA, 106(23):9180-4 (2009).

Chen, X. et al., Fusion protein linkers: property, design and functionality, Advanced drug delivery reviews, 65(10):1357-1369 (2013).

Comella, C. et al., Comparison of botulinum toxin serotypes A and B for the treatment of cervical dystonia, Neurology, 65(9):1423-9 (2005).

Cote et al., Botulinum toxin type A injections: adverse events reported to the US Food and Drug Administration in therapeutic and cosmetic cases, J Am Acad Dermatol, 53: 407-415 (2005).

Craxton, A manual collection of Syt, Esyt, Rph3a, Rph3al, Doc2, and Dblc2 genes from 46 metazoan genomes—an open access resource for neuroscience and evolutionary biology, BMC Genomics, 11(37): 1-21 (2010).

Dasgupta, B. and Boroff, D., Chromatographic isolation of hemagglutinin-free neurotoxin from crystalline toxin of Clostridium botulinum type A, Biochim Biophys Acta., 147(3):603-5 (1967).

DATABASE Geneseq [Online], Modified Clostridial toxin construct BoNT/B-HA-17 beta, retrieved from EBI accession No. GSP:AZY12935, Database accession No. AZY12935 sequence, 2 pages (2012).

DATABASE UniProt [Online], Neurotoxin B8, retrieved from EBI accession No. UNIPROT:M9VUL2, Database accession No. M9VUL2 sequence, 2 pages (2013).

Dekleva, M.L. et al., Nicking of single chain Clostridium botulinum type A neurotoxin by an endogenous protease, Biochem Biophys Res Commun, 162(2):767-72 (1989).

Dolimbek et al., Immune recognition of botulinum neurotoxin B: antibody-binding regions on the heavy chain of the toxin, Mol Immunol, 45: 910-924 (2008).

Dolly, J. et al., Neuro-exocytosis: botulinum toxins as inhibitory probes and versatile therapeutics, Curr Opin Pharmacol., 9(3):326-35 (2009).

Dong et al. Glycosylated SV2A and SV2B Mediate the Entry of Botulinum neurotoxin E into neurons, Mol Biol Cell, 19: 5226-5237 (2008).

Dong et al., Mechanism of botulinum neurotoxin B and G entry into hippocampal neurons, J Cell Biol, 179(7): 1511-1522 (2007).

Dong et al., SV2 is the Protein Receptor for Botulinum Neurotoxin A, Science, 312(5773):592-596 (2006) .

Dong et al., Synaptotagmins I and II mediate entry of botulinum neurotoxin B into cells, J Cell Biol, 162(7): 1293-1303 (2003).

Duff J. et al., Studies on immunity to toxins of Clostridium botulinum. I. A simplified procedure for isolation of type A toxin, J Bacteriol., 73(1):42-7 (1957).

Duff, J. et al., Studies on immunity to toxins of Clostridium botulinum. II. Production and purification of type B toxin for toxoid, J Bacteriol., 73(5):597-601 (1957).

Finzi, E. and Rosenthal, N., Treatment of depression with onabotulinumtoxinA: a randomized, double-blind, placebo controlled trial, J Psychiatr Res., 52:1-6 (2014).

Frankel, A.E., et al., Characterization of diphtheria fusion proteins targeted to the human interleukin-3 receptor, Protein Eng., 13(8):575-581 (2000).

Fu et al., Glycosylated SV2 and Gangliosides as Dual Receptors for Botulinum Neurotoxin Serotype F, Biochemistry, 48(24): 5631-5641 (2009).

Gasser, B. et al., Antibody production with yeasts to filamentous fungi: on the road to large scale?, Biotechnology Letters, 29(2):201-212 (2007).

Guo, J. et al., Engineering Clostridia Neurotoxins with elevated catalytic activity, Toxicon, 74:158-66 (2013).

Hexsel, C. et al., Botulinum toxin type A for aging face and aesthetic uses, Dermatol Ther., 24(1):54-61 (2011).

Hill et al., Genetic diversity among Botulinum Neurotoxin-producing clostridial strains, J Bacteriol, 189(3): 818-832 (2007).

Humeau et al., How botulinum and tetanus neurotoxins block neurotransmitter release, Biochimie, 82(5):427-446 (2000).

Ihara et al., Sequence of the gene for Clostridium botulinum type B neurotoxin associated with infant botulism, expression of the C-terminal half of heavy chain and its binding activity, Biochim Biophys Acta, 1625: 19-26 (2003).

International Search Report for PCT/US2016/024211 (Engineered Botulinum Neurotoxin, filed Mar. 25, 2016), issued by ISA/EPO, 8 pages (Sep. 9, 2016).

International Search Report for PCT/US2013/030737 (Engineered Botulinum Neurotoxin, filed Mar. 13, 2013), issued by ISA/EP, 6 pages (Oct. 11, 2013).

International Search Report for PCT/US2017/048508 (Engineered Botulinum Neurotoxin, filed Aug. 24, 2017), issued by ISA/EP, 7 pages (Oct. 24, 2017).

Jackson, J. et al., Botulinum toxin A for prophylactic treatment of migraine and tension headaches in adults: a meta-analysis, JAMA, 307(16):1736-45 (2012).

Jahn, E.M., et al., How to systematically evaluate immunogenicity of therapeutic proteins-regulatory considerations, New biotechnology, 25(5):280-286 (2009).

Jahn, R. and Scheller, R., SNAREs—engines for membrane fusion, Nat Rev Mol Cell Biol., 7(9):631-43 (2006).

Jankovic, J. and Brin, M., Therapeutic uses of botulinum toxin, N Engl J Med., 324(17):1186-94 (1991).

Jiang, Y. et al., Current and potential urological applications of botulinum toxin A, Nat Rev Urol., 12(9):519-33 (2015).

Jin et al., Botulinum neurotoxin B recognizes its protein receptor with high affinity and specificity, Nature, 444(7122):1092-1095 (2006).

Jin, R. et al., Botulinum neurotoxin B recognizes its protein receptor with high affinity and specificity, Nature, 444(21):1092-1095 (2006).

Johnson, Eric A., Clostridial toxins as therapeutic agents: benefits of nature's most toxic proteins, Annu Rev Microbiol, 53: 551-575 (1999).

Karimova, G. et al., A bacterial two-hybrid system based on a reconstituted signal transduction pathway, Proc Natl Acad Sci USA, 95(10):5752-6 (1998).

Kohda, T. et al., Differential contribution of the residues in C-terminal half of the heavy chain of botulinum neurotoxin type B to its binding to the ganglioside GT1b and the synaptotagmin 2/GT1b complex, Microbial Pathogenesis, 42:72-79 (2007).

Kozaki et al., Characterization of Clostridium botulinum Type B Neurotoxin Associated with Infant Botulism in Japan, Infect Immun, 66(10): 4811-4816 (1998).

Lacy, D. et al., Crystal structure of botulinum neurotoxin type A and implications for toxicity, Nat Struct Biol., 5(10):898-902 (1998).

Lalli et al., Functional characterisation of tetanus and botulinum neurotoxins binding domains, J Cell Sci, 112: 2715-2724 (1999).

Lalli et al., The Journey of tetanus and botulinum neurotoxins in neurons, Trends Microbiol, 11 (9): 431-437 (2003).

Lange et al., Neutralizing Antibodies and Secondary Therapy Failure After Treatment With Botulinum Toxin Type A: Much Ado About Nothing?, Clin Neuropharmacol, 32: 213-218 (2009).

Lee, K., et al., Molecular basis for disruption of E-cadherin adhesion by botulinum neurotoxin A complex, Science, 344(6190):1405-10 (2014).

Li, X. et al., Clostridium butyricum-Guardian of intestinal health, Fudan University Press, pp. 347-348 (2008) NON-ENGLISH.

Lietzow, M. et al., Composition and Molecular Size of Clostridium botulinum Type A Toxin-Hemagglutinin Complex, Protein J., 28:250-251 (2009).

Lim, E. et al., Botulinum toxin: A novel therapeutic option for bronchial asthma?, Medical Hypotheses, 66:915-919 (2006).

Maeda, Y. et al., Engineering of functional chimeric protein G-Vargula Luciferase, Analytical biochemistry, 249(2):147-152 (1997).

(56) References Cited

OTHER PUBLICATIONS

Mahrold et al., The synaptic vesicle protein 2C mediates the uptake of botulinum neurotoxin A into phrenic nerves, FEBS Lett, 580: 2011-2014 (2006).

Malizio, C. et al., Purification of Clostridium botulinum type A neurotoxin, Methods Mol Biol., 145:27-39 (2000).

Masuyer, G. et al., Engineered botulinum neurotoxins as new therapeutics, Annu Rev Pharmacol Toxicol., 54:27-51 (2014).

Montal, M., Botulinum neurotoxin: a marvel of protein design, Annu Rev Biochem, 79:591-617 (2010).

Montecucco, C. and Molgo, J., Botulinal neurotoxins: revival of an old killer, Curr Opin Pharmacol, 5: 274-279 (2005).

Montecucco, How do tetanus and botulinum toxins bind to neuronal membranes?, TIBS, 11: 314-317 (1986).

Moriishi et al., Mosaic structures of neurotoxins produced from Clostridium botulinum types C and D organisms, Biochim Biophys Acta, 1307: 123-126 (1996).

Muller, S. et al., Spliceosomal peptide P140 for immunotherapy of systemic lupus erythematosus: results of an early phase II clinical trial, Arthritis & Rheumatism, Official Journal of the American College of Rheumatology, 58(12):3873-3883 (2008).

Munchau, A. and Bhatia, K., Regular Review: Uses of botulinum toxin injection in medicine today, British Medical Journal, 320 (77228):161-165 (2000).

Naumann, M. et al., Botulinum Toxin in Treatment of Neurological Disorders of the Autonomic Nervous System, Arch Neurol., 56:914-916 (1999).

Nishiki et al., Identification of Protein Receptor for Clostridium botulinum Type B Neurotoxin in Rat Brain Synaptosomes, J Biol Chem, 269(14): 10498-10503 (1994).

Nishiki et al., The high-affinity binding of Clostridium botulinum type B neurotoxin to synaptotagmin II associated with gangliosides GT1b/GD1a, FEBS Lett 378: 253-257 (1996).

Orlando, M., Modification of proteins and low molecular weight substances with hydroxyethyl starch (HES), Inauguraldissertation, Giesen, p. 166, c. 15 (2003).

Pang et al., Synaptotagmin-2 Is Essential for Survival and Contributes to Ca2+ Triggering of Neurotransmitter Release in Central and Neuromuscular Synapses, J Neurosci, 26(52): 13493-13504 (2006).

Pappert et al., Botulinum Toxin Type B vs. Type A in Toxin-Naive patients with Cervical Dystonia: Randomized, Double-Blind, Noninferiority Trial, Mov Disord, 23(4): 510-517 (2008).

Peng et al., Botulinum Neurotoxin D Uses Synaptic Vesicle Protein SV2 and Gangliosides as Receptors, PLoS Pathog, 7: e1002008 (2011).

Peng et al., Botulinum neurotoxin D-C uses synaptotagmin I/II as receptors and human synaptotagmin II is not an effective receptor for type B, D-C, and G toxins, J Cell Sci, 125(13):3233-3242 (2012).

Peng, L. et al., Widespread sequence variations in VAMP1 across vertebrates suggest a potential selective pressure from botulinum neurotoxins, PLoS Pathog, 10(7):e1004177 (2014).

Pickett, A. and Perrow, K., Composition and molecular size of Clostridium botulinum Type A toxin-hemagglutinin complex, Protein J., 28(5):248-9 (2009).

Pickett, A., Botulinum Toxin as a Clinical Product: Manufacture and Pharmacology. In Clinical Applications of Botulinum Neurotoxin, Current Topics in Neurotoxicity, Springer New York, pp. 7-49 (2014).

Pirazzini, M et al., Neutralisation of specific surface carboxylates speeds up translocation of botulinum neurotoxin type B enzymatic domain, FEBS Lett, 587(23):3831-6 (2013).

Rossetto, O. et al., Botulinum neurotoxins: genetic, structural and mechanistic insights, Nat Rev Microbiol., 12(8):535-49 (2014).

Rummel et al., Botulinum neurotoxins C, E and F bind gangliosides via a conserved binding site prior to stimulation—dependent uptake with botulinum neurotoxin F utilising the three isoforms of SV2 as second receptor, J Neurochem, 110: 1942-1954 (2009).

Rummel et al., Exchange of the HCC domain mediating double receptor recognition improves the pharmacodynamic properties of botulinum neurotoxin, FEBS J, 278: 4506-4515 (2011).

Rummel et al., Identification of the protein receptor binding site of botulinum neurotoxins B and G proves the double-receptor concept, PNAS, 104(1): 359-364 (2007).

Rummel, A. et al., Synaptotagmins I and II Act as Nerve Cell Receptors for Botulinum Neurotoxin G, The Journal of Biological Chemistry, 279(29): 30865-30870 (2004).

Rummel, A. et al., The HCC-domain of botulinum neurotoxins A and B exhibits a singular ganglioside binding site displaying serotype specific carbohydrate interaction, Mol Microbiol, 51: 631-643 (2004).

Schantz, E. and Johnson, E., Properties and use of botulinum toxin and other microbial neurotoxins in medicine, Microbiol Rev., 56(1):80-99 (1992).

Schiavo et al., Neurotoxins affecting neuroexocytosis, Physiol Rev, 80: 717-766 (2000).

Schiavo, G. et al, Botulinum neurotoxin type B, UnitProtKB—P10844 (BXB_CLOBO), 7 pages (2007).

Sikorra, S. et al., Identification and Characterization of Botulinum Neurotoxin A Substrate Binding Pockets and Their Re-Engineering for Human SNAP-23, J Mol Biol., 428(2Pt A):372-384 (2016).

Snipe, P. and Sommer, H., Studies on botulinus toxin 3. Acid precipitation of botulinus toxin, The Journal of infectious diseases, 43(2):152-160 (1928).

Stanker, L. et al., A Monoclonal Antibody Based Capture ELISA for Botulinum Neutotoxin Serotype B: Toxin Detection in Food, Toxins, 5:2212-2226 (2013).

Strotmeier, J. et al., Human synaptotagmin-II is not a high affinity receptor for botulinum neurotoxin B and G: increased therapeutic dosage and immunogenicity, FEBS Lett, 586(4):310-3 (2012).

Südhof, T. and Rothman, J., Membrane fusion: grappling with SNARE and SM proteins, Science, 323(5913):474-7 (2009).

Sutton, R. et al., Crystal structure of a SNARE complex involved in synaptic exocytosis at 2.4 A resolution, Nature, 395(6700):347-53 (1998).

Tao, L. and Biswas, I., ClpL is required for folding of CtsR in *Streptococcus* mutans, J Bacteriol., 195(3):576-84 (2013).

Truong, D. and Jost, W., Botulinum toxin: clinical use, Parkinsonism Relat Disord., 12(6):331-55 (2006).

Tse, C. et al., Preparation and characterisation of homogeneous neurotoxin type A from Clostridium botulinum. Its inhibitory action on neuronal release of acetylcholine in the absence and presence of beta-bungarotoxin, Eur J Biochem., 122(3):493-500 (1982).

Turton et al., Botulinum and Tetanus Neurotoxins: structure, function and therapeutic utility, Trends Biochem. Sci., 27(11 ): 552-558 (2002).

Van Baar et al., Characterisation of botulinum toxins type A and B, by matrix-assisted laser desorption ionisation and electrospray mass spectrometry, Journal of Chromatography A, 970(1-2): 95-115 (2002).

Visco, A. et al., Anticholinergic therapy vs. onabotulinumtoxinA for urgency urinary incontinence., N Engl J Med., 367(19):1803-13 (2012).

Walder, R. and Walder, J., Oligodeoxynucleotide-directed mutagenesis using the yeast transformation system, Gene, 42(2):133-9 (1986).

Wang et al., Longer-acting and highly potent chimaeric inhibitors of excessive exocytosis created with domains from botulinum neurotoxin A and B, Biochem J, 444: 59-67 (2012).

Written Opinion for PCT/US2016/024211 (Engineered Botulinum Neurotoxin, filed Mar. 25, 2016), issued by ISA/EPO, 8 pages (Sep. 9, 2016).

Written Opinion for PCT/US2013/030737 (Engineered Botulinum Neurotoxin, filed Mar. 13, 2013), issued by ISA/EP, 8 pages (Oct. 11, 2013).

Written Opinion for PCT/US2017/048508 (Engineered Botulinum Neurotoxin, filed Aug. 24, 2017), issued by ISA/EP, 13 pages (Oct. 24, 2017).

Yamasaki, S. et al., Cleavage of members of the synaptobrevin/VAMP family by types D and F botulinal neurotoxins and tetanus toxin, J Biol Chem, 269(17):12764-72 (1994).

(56) References Cited

OTHER PUBLICATIONS

Fischer, A., Synchronized Chaperone Function of Botulinum Neu-
rotoxin Domains Mediates Light Chain Translocation into Neurons,
Botulinum Neurotoxins, 364:115-137 (2012).
You, Z, et al., Advances in research on vaccines and antibodies for
defending against botulism, Military Medical Sciences, 7:550-554.
(2013).
Wenwen, X, and Jing-Lin, W., Research progress of Clostridial
neurotoxins, Chinese Bulletin of Life Sciences, 28(1); 11 pages
(2016) English Abstract.

* cited by examiner

FIG. 1A

Three-domain structure of BoNTs

Light chain (50 kDa)          Heavy chain (100 kDa)

NH$_2$-  (protease domain)   (translocation   (receptor-binding
                              domain)          domain)

S—S     H$_N$     H$_C$     -COOH

| Toxins | Protein Receptors |
| --- | --- |
| BoNT/B, G, D-C | Synaptotagmin I and II (Syt I/II) |
| BoNT/A, E, D, F | SV2A, B, and C |

| Residue in BoNT/B | Close to residue X in Syt II | Residue in BoNT/B | Close to residue X in Syt II |
|---|---|---|---|
| 1113 | 57 | 1194 | 47, 50, 51 and 54 |
| 1115 | 53 | 1196 | 47 and 50 |
| 1116 | 53 and 57 | 1197 | 47 and 50 |
| 1117 | 50, 53 and 54 | 1199 | 47 |
| 1118 | 54 and 57 | 1201 | 47 and 51 |
| 1178 | 50 | 1203 | 51 and 55 |
| 1181 | 47 | 1204 | 51, 54 and 55 |
| 1183 | 54 and 55 | 1245 | 57 |
| 1191 | 58 | 1256 | 57 |
| 1192 | 57 | | |

*FIG. 3B*

Summary of the BACTH screening

| Residue position | Total number of screened colonies | Number of blue colonies* | Percentage of blue colonies* |
|---|---|---|---|
| 1113 | 935 | 0 | 0 |
| 1115 | 382 | 0 | 0 |
| 1116 | >1000 | 0 | 0 |
| 1117 | >1000 | 0 | 0 |
| 1118 | >1000 | 0 | 0 |
| 1178 | 380 | 29 | 7.6 |
| 1181 | 440 | 0 | 0 |
| 1183 | 980 | 39 | 4.0 |
| 1191 | 874 | 198 | 22.7 |
| 1192 | >1000 | 0 | 0 |
| 1194 | 620 | 0 | 0 |
| 1196 | >1000 | 0 | 0 |
| 1197 | >1000 | 0 | 0 |
| 1199 | 624 | 32 | 5.1 |
| 1201 | 634 | 0 | 0 |
| 1203 | 612 | 0 | 0 |
| 1204 | 764 | 0 | 0 |
| 1245 | 394 | 0 | 0 |
| 1256 | 488 | 0 | 0 |

FIG. 5A

Mutations obtained from blue colonies

| Residue position | Mutations obtained from deep blue colonies | Mutations obtained from light blue colonies |
|---|---|---|
| 1191 | M, C, V, Q, L, Y | S, A, T, N |
| 1183 |  | C, P |
| 1199 |  | W, E, Y, H |
| 1178 |  | Y, Q, A, S |

FIG. 5B

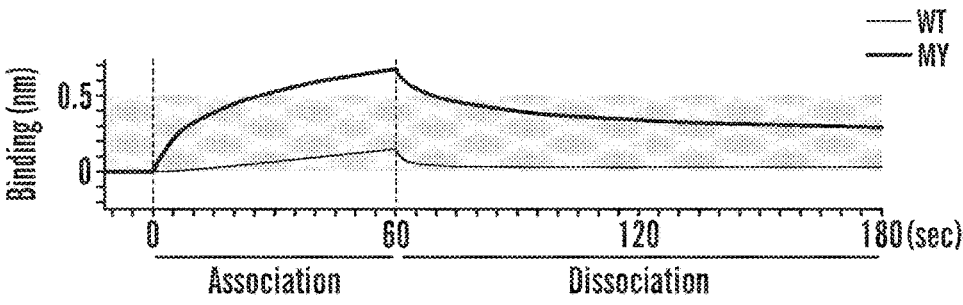

*FIG.* *8A*

| Ligand | Analyte (BoNT/B $H_C$ mutants) | $k_{on}$ (1/Ms) | $k_{on}$ error | $k_{off}$ (1/s) | $k_{off}$ error | $k_D$ (μM) |
|---|---|---|---|---|---|---|
| GST-mSyt II | WT | $1.47 \times 10^4$ | $5.89 \times 10^2$ | $1.98 \times 10^{-3}$ | $5.18 \times 10^{-5}$ | 0.13 |
| GST-hSyt II | WT | NA | NA | NA | NA | > 20 |
|  | E1191M | $5.21 \times 10^3$ | $2.11 \times 10^2$ | $3.51 \times 10^{-2}$ | $4.62 \times 10^{-4}$ | 6.7 |
|  | E1191M, S1199W | $1.65 \times 10^4$ | $3.87 \times 10^2$ | $1.81 \times 10^{-2}$ | $1.79 \times 10^{-4}$ | 1.10 |
|  | E1191M, S1199Y | $1.56 \times 10^4$ | $3.72 \times 10^2$ | $1.13 \times 10^{-2}$ | $1.74 \times 10^{-4}$ | 0.72 |
|  | E1191M, W1178Q | $2.23 \times 10^4$ | $1.33 \times 10^3$ | $3.52 \times 10^{-2}$ | $8.25 \times 10^{-4}$ | 1.58 |
|  | E1191C, S1199W | $1.32 \times 10^4$ | $4.70 \times 10^2$ | $1.19 \times 10^{-2}$ | $8.90 \times 10^{-4}$ | 0.90 |
|  | E1191C, S1199Y | $1.47 \times 10^4$ | $4.96 \times 10^2$ | $1.44 \times 10^{-2}$ | $1.91 \times 10^{-4}$ | 0.98 |
|  | E1191C, W1178Q | $6.89 \times 10^3$ | $5.18 \times 10^2$ | $2.96 \times 10^{-2}$ | $3.23 \times 10^{-4}$ | 4.30 |
|  | E1191Q, S1199W | $8.28 \times 10^3$ | $5.50 \times 10^2$ | $2.21 \times 10^{-2}$ | $3.34 \times 10^{-4}$ | 2.67 |
|  | E1191Q, S1199Y | $2.42 \times 10^4$ | $1.16 \times 10^3$ | $2.85 \times 10^{-2}$ | $4.60 \times 10^{-4}$ | 1.18 |
|  | E1191Q, W1178Q | NA | NA | NA | NA | > 20 |
|  | E1191V, S1199W | $1.86 \times 10^4$ | $6.49 \times 10^2$ | $1.30 \times 10^{-2}$ | $2.44 \times 10^{-4}$ | 0.70 |
|  | E1191V, S1199Y | $2.31 \times 10^4$ | $9.18 \times 10^2$ | $1.35 \times 10^{-2}$ | $2.68 \times 10^{-4}$ | 0.59 |
|  | E1191V, W1178Q | $6.08 \times 10^3$ | $4.64 \times 10^2$ | $1.83 \times 10^{-2}$ | $2.75 \times 10^{-4}$ | 3.01 |
|  | E1191M, S1199W, W1178Q | $1.52 \times 10^4$ | $3.49 \times 10^2$ | $1.72 \times 10^{-2}$ | $1.71 \times 10^{-4}$ | 1.13 |

*FIG.* *8B*

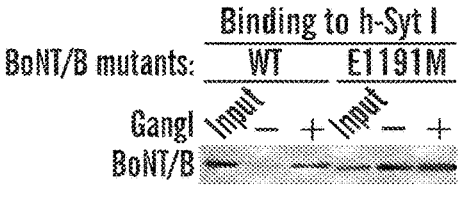
*FIG. 9A*
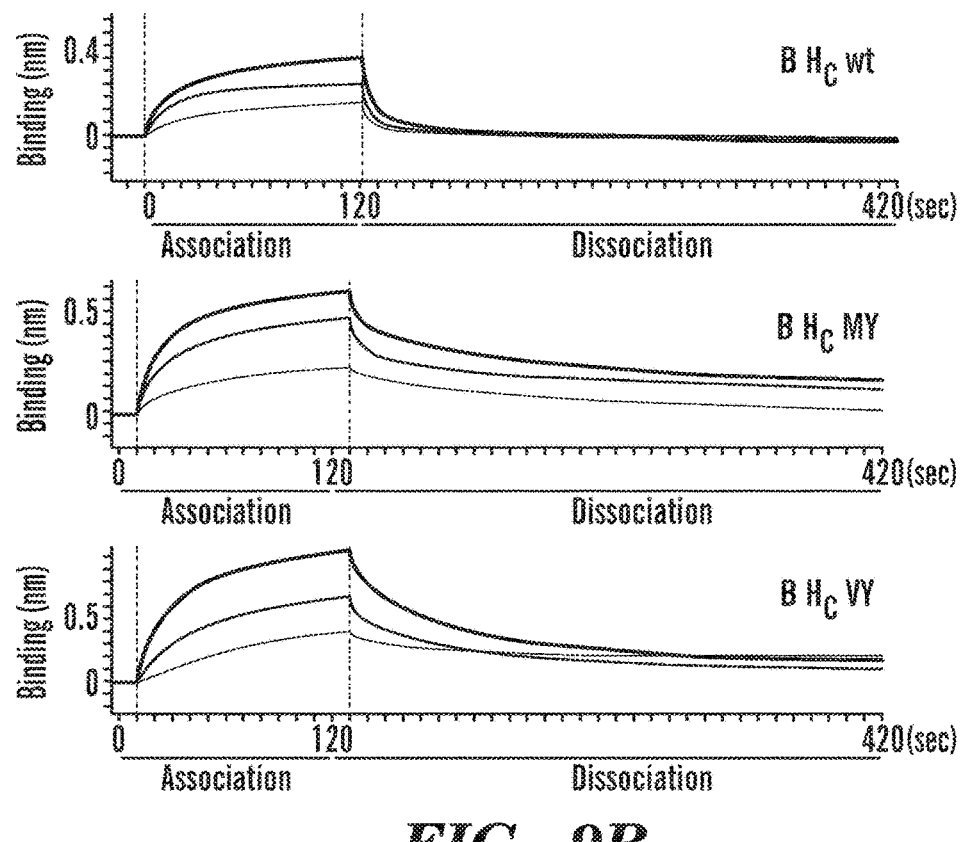
*FIG. 9B*
|  | $k_{on}$ (1/Ms) | $k_{on}$ error | $k_{off}$ (1/s) | $k_{off}$ error | $k_D$ ($\mu$M) |
|---|---|---|---|---|---|
| B $H_C$ wt | NA | NA | NA | NA | $> 20$ |
| B $H_C$ MY | $4.82d'10^3$ | $2.96d'10^2$ | $1.40d'10^{-2}$ | $4.55d'10^{-4}$ | 2.90 |
| B $H_C$ VY | $2.71d'10^3$ | $9.11d'10^1$ | $1.58d'10^{-2}$ | $2.10d'10^{-4}$ | 5.82 |
*FIG. 9C*

Protein sequence of BoNT/B-HC (strain 1) (residues 857-1291
of BoNT/B, strain 1, GenBank:
AB232927.1)

NSEILNNIILNLRYKDNNLIDLSGYGAKVEVYDGVELNDKNQFKLTSSANSKIRVTQNQN
IIFNSVFLDFSVSFWIRIPKYKNDGIQNYIHNEYTIINCMKNNSGWKISIRGNRIIWTLIDIN
GKTKSVFFEYNIREDISEYINRWFFVTITNNLNNAKIYINGKLESNTDIKDIREVIANGEIIF
KLDGDIDRTQFIWMKYFSIFNTELSQSNIEERYKIQSYSEYLKDFWGNPLMYNKEYYMF
NAGNKNSYIKLKKDSPVGEILTRSKYNQNSKYINYRDLYIGEKFIIRRKSNSQSINDDIVR
KEDYIYLDFFNLNQEWRVYTYKYFKKEEEKLFLAPISDSDEFYNTIQIKEYDEQPTYSCQ
LLFKKDEESTDEIGLIGIHRFYESGIVFEEYKDYFCISKWYLKEVKRKPYNLKLGCNWQFI
PKDEGWTE

*FIG. 12*

The nucleic acid sequence encoding BoNT/B-HC (strain B1)
(residues 857-1291 of BoNT/B,strain 1, based on GenBank:
AB232927.1). Note: the sequence has been optimized for
expression in E.coli

```
AACAGCGAAATCCTGAACAACATTATTCTGAACCTGCGCTATAAAGATAACAACCTGATTGA
TCTGAGCGGCTATGGCGCGAAAGTGGAAGTGTATGATGGCGTGGAACTGAACGATAAAAA
CCAGTTCAAACTGACCAGCTCTGCGAACAGCAAAATTCGTGTGACCCAGAACCAGAACATT
ATCTTCAACAGCGTGTTTCTGGATTTTAGCGTGAGCTTTTGGATTCGCATCCCGAAATATAA
AAACGATGGCATCCAGAACTATATCCACAACGAATACACCATTATCAACTGCATGAAAAACA
ACAGCGGCTGGAAAATTAGCATTCGTGGCAACCGTATTATTTGGACCCTGATCGATATTAA
CGGCAAAACCAAAAGCGTGTTCTTCGAATACAACATCCGCGAAGATATCAGCGAATACATT
AACCGCTGGTTCTTTGTGACCATTACCAACAACCTGAACAACGCGAAATTTATATCAACGG
TAAACTGGAAAGCAACACCGATATCAAAGATATCCGCGAAGTGATTGCGAACGGCGAAATC
ATCTTTAAACTGGATGGCGATATTGATCGTACCCAGTTCATCTGGATGAAATACTTCAGCAT
CTTCAACACCGAACTGAGCCAGAGCAACATTGAAGAACGCTACAAAATCCAGAGCTATAGC
GAATACCTGAAAGATTTTTGGGGCAATCCGCTGATGTATAACAAAGAGTATTACATGTTCAA
CGCGGGTAACAAAAACAGCTATATCAAACTGAAAAAAGATAGCCCGGTGGGCGAAATTCTG
ACCCGTAGCAAATATAACCAGAACAGCAAATACATCAACTATCGCGATCTGTATATCGGCG
AAAAATTTATCATTCGCCGCAAAGCAACAGCCAGAGCATTAACGATGATATCGTGCGCAA
AGAAGATTATATCTACCTGGATTTTTTCAACCTGAACCAGGAATGGCGCGTTTATACCTATA
AATATTTCAAAAAAGAGGAAGAGAAACTGTTTCTGGCCCCGATTAGCGATAGCGATGAATTT
TACAACACCATCCAAATTAAAGAATACGATGAACAGCCGACCTATAGCTGCCAGCTGCTGT
TTAAAAAAGATGAAGAAAGCACCGATGAAATTGGCCTGATTGGCATCCATCGTTTCTATGAA
AGCGGCATCGTGTTCGAAGAATATAAAGATTATTTCTGCATCAGCAAATGGTATCTGAAAGA
AGTGAAACGCAAACCGTATAACCTGAAACTGGGCTGCAACTGGCAGTTTATTCCGAAAGAT
GAAGGCTGGACCGAATAA
```

*FIG. 13*

Clostridium botulinum serotype A:
(1296 a.a.)
Met Pro Phe Val Asn Lys Gln Phe Asn Tyr Lys Asp Pro Val Asn Gly
Val Asp Ile Ala Tyr Ile Lys Ile Pro Asn Ala Gly Gln Met Gln Pro
Val Lys Ala Phe Lys Ile His Asn Lys Ile Trp Val Ile Pro Glu Arg
Asp Thr Phe Thr Asn Pro Glu Glu Gly Asp Leu Asn Pro Pro Pro Glu
Ala Lys Gln Val Pro Val Ser Tyr Tyr Asp Ser Thr Tyr Leu Ser Thr
Asp Asn Glu Lys Asp Asn Tyr Leu Lys Gly Val Thr Lys Leu Phe Glu
Arg Ile Tyr Ser Thr Asp Leu Gly Arg Met Leu Leu Thr Ser Ile Val
Arg Gly Ile Pro Phe Trp Gly Gly Ser Thr Ile Asp Thr Glu Leu Lys
Val Ile Asp Thr Asn Cys Ile Asn Val Ile Gln Pro Asp Gly Ser Tyr
Arg Ser Glu Glu Leu Asn Leu Val Ile Ile Gly Pro Ser Ala Asp Ile
Ile Gln Phe Glu Cys Lys Ser Phe Gly His Glu Val Leu Asn Leu Thr
Arg Asn Gly Tyr Gly Ser Thr Gln Tyr Ile Arg Phe Ser Pro Asp Phe
Thr Phe Gly Phe Glu Glu Ser Leu Glu Val Asp Thr Asn Pro Leu Leu
Gly Ala Gly Lys Phe Ala Thr Asp Pro Ala Val Thr Leu Ala His Glu
Leu Ile His Ala Gly His Arg Leu Tyr Gly Ile Ala Ile Asn Pro Asn
Arg Val Phe Lys Val Asn Thr Asn Ala Tyr Tyr Glu Met Ser Gly Leu
Glu Val Ser Phe Glu Glu Leu Arg Thr Phe Gly Gly His Asp Ala Lys
Phe Ile Asp Ser Leu Gln Glu Asn Glu Phe Arg Leu Tyr Tyr Tyr Asn
Lys Phe Lys Asp Ile Ala Ser Thr Leu Asn Lys Ala Lys Ser Ile Val
Gly Thr Thr Ala Ser Leu Gln Tyr Met Lys Asn Val Phe Lys Glu Lys
Tyr Leu Leu Ser Glu Asp Thr Ser Gly Lys Phe Ser Val Asp Lys Leu
Lys Phe Asp Lys Leu Tyr Lys Met Leu Thr Glu Ile Tyr Thr Glu Asp
Asn Phe Val Lys Phe Phe Lys Val Leu Asn Arg Lys Thr Tyr Leu Asn
Phe Asp Lys Ala Val Phe Lys Ile Asn Ile Val Pro Lys Val Asn Tyr
Thr Ile Tyr Asp Gly Phe Asn Leu Arg Asn Thr Asn Leu Ala Ala Asn
Phe Asn Gly Gln Asn Thr Glu Ile Asn Asn Met Asn Phe Thr Lys Leu
Lys Asn Phe Thr Gly Leu Phe Glu Phe Tyr Lys Leu Leu Cys Val Arg
Gly Ile Ile Thr Ser Lys Thr Lys Ser Leu Asp Lys Gly Tyr Asn Lys
Ala Leu Asn Asp Leu Cys Ile Lys Val Asn Asn Trp Asp Leu Phe Phe
Ser Pro Ser Glu Asp Asn Phe Thr Asn Asp Leu Asn Lys Gly Glu Glu
Ile Thr Ser Asp Thr Asn Ile Glu Ala Ala Glu Glu Asn Ile Ser Leu
Asp Leu Ile Gln Gln Tyr Tyr Leu Thr Phe Asn Phe Asp Asn Glu Pro
Glu Asn Ile Ser Ile Glu Asn Leu Ser Ser Asp Ile Ile Gly Gln Leu
Glu Leu Met Pro Asn Ile Glu Arg Phe Pro Asn Gly Lys Lys Tyr Glu
Leu Asp Lys Tyr Thr Met Phe His Tyr Leu Arg Ala Gln Glu Phe Glu
His Gly Lys Ser Arg Ile Ala Leu Thr Asn Ser Val Asn Glu Ala Leu
Leu Asn Pro Ser Arg Val Tyr Thr Phe Phe Ser Ser Asp Tyr Val Lys
Lys Val Asn Lys Ala Thr Glu Ala Ala Met Phe Leu Gly Trp Val Glu
Gln Leu Val Tyr Asp Phe Thr Asp Glu Thr Ser Glu Val Ser Thr Thr
Asp Lys Ile Ala Asp Ile Thr Ile Ile Ile Pro Tyr Ile Gly Pro Ala
Leu Asn Ile Gly Asn Met Leu Tyr Lys Asp Asp Phe Val Gly Ala Leu
Ile Phe Ser Gly Ala Val Ile Leu Leu Glu Phe Ile Pro Glu Ile Ala
Ile Pro Val Leu Gly Thr Phe Ala Leu Val Ser Tyr Ile Ala Asn Lys
Val Leu Thr Val Gln Thr Ile Asp Asn Ala Leu Ser Lys Arg Asn Glu
Lys Trp Asp Glu Val Tyr Lys Tyr Ile Val Thr Asn Trp Leu Ala Lys

*FIG. 14*

```
Val Asn Thr Gln Ile Asp Leu Ile Arg Lys Lys Met Lys Glu Ala Leu
Glu Asn Gln Ala Glu Ala Thr Lys Ala Ile Ile Asn Tyr Gln Tyr Asn
Gln Tyr Thr Glu Glu Glu Lys Asn Asn Ile Asn Phe Asn Ile Asp Asp
Leu Ser Ser Lys Leu Asn Glu Ser Ile Asn Lys Ala Met Ile Asn Ile
Asn Lys Phe Leu Asn Gln Cys Ser Val Ser Tyr Leu Met Asn Ser Met
Ile Pro Tyr Gly Val Lys Arg Leu Glu Asp Phe Asp Ala Ser Leu Lys
Asp Ala Leu Leu Lys Tyr Ile Tyr Asp Asn Arg Gly Thr Leu Ile Gly
Gln Val Asp Arg Leu Lys Asp Lys Val Asn Asn Thr Leu Ser Thr Asp
Ile Pro Phe Gln Leu Ser Lys Tyr Val Asp Asn Gln Arg Leu Leu Ser
Thr Phe Thr Glu Tyr Ile Lys Asn Ile Ile Asn Thr Ser Ile Leu Asn
Leu Arg Tyr Glu Ser Asn His Leu Ile Asp Leu Ser Arg Tyr Ala Ser
Lys Ile Asn Ile Gly Ser Lys Val Asn Phe Asp Pro Ile Asp Lys Asn
Gln Ile Gln Leu Phe Asn Leu Glu Ser Ser Lys Ile Glu Val Ile Leu
Lys Asn Ala Ile Val Tyr Asn Ser Met Tyr Glu Asn Phe Ser Thr Ser
Phe Trp Ile Arg Ile Pro Lys Tyr Phe Asn Ser Ile Ser Leu Asn Asn
Glu Tyr Thr Ile Ile Asn Cys Met Glu Asn Asn Ser Gly Trp Lys Val
Ser Leu Asn Tyr Gly Glu Ile Ile Trp Thr Leu Gln Asp Thr Gln Glu
Ile Lys Gln Arg Val Val Phe Lys Tyr Ser Gln Met Ile Asn Ile Ser
Asp Tyr Ile Asn Arg Trp Ile Phe Val Thr Ile Thr Asn Asn Arg Leu
Asn Asn Ser Lys Ile Tyr Ile Asn Gly Arg Leu Ile Asp Gln Lys Pro
Ile Ser Asn Leu Gly Asn Ile His Ala Ser Asn Asn Ile Met Phe Lys
Leu Asp Gly Cys Arg Asp Thr His Arg Tyr Ile Trp Ile Lys Tyr Phe
Asn Leu Phe Asp Lys Glu Leu Asn Glu Lys Glu Ile Lys Asp Leu Tyr
Asp Asn Gln Ser Asn Ser Gly Ile Leu Lys Asp Phe Trp Gly Asp Tyr
Leu Gln Tyr Asp Lys Pro Tyr Tyr Met Leu Asn Leu Tyr Asp Pro Asn
Lys Tyr Val Asp Val Asn Asn Val Gly Ile Arg Gly Tyr Met Tyr Leu
Lys Gly Pro Arg Gly Ser Val Met Thr Thr Asn Ile Tyr Leu Asn Ser
Ser Leu Tyr Arg Gly Thr Lys Phe Ile Ile Lys Lys Tyr Ala Ser Gly
Asn Lys Asp Asn Ile Val Arg Asn Asn Asp Arg Val Tyr Ile Asn Val
Val Val Lys Asn Lys Glu Tyr Arg Leu Ala Thr Asn Ala Ser Gln Ala
Gly Val Glu Lys Ile Leu Ser Ala Leu Glu Ile Pro Asp Val Gly Asn
Leu Ser Gln Val Val Val Met Lys Ser Lys Asn Asp Gln Gly Ile Thr
Asn Lys Cys Lys Met Asn Leu Gln Asp Asn Asn Gly Asn Asp Ile Gly
Phe Ile Gly Phe His Gln Phe Asn Asn Ile Ala Lys Leu Val Ala Ser
Asn Trp Tyr Asn Arg Gln Ile Glu Arg Ser Ser Arg Thr Leu Gly Cys
Ser Trp Glu Phe Ile Pro Val Asp Asp Gly Trp Gly Glu Arg Pro Leu
```

Clostridium botulinum serotype B
(1291 a.a.)

```
Met Pro Val Thr Ile Asn Asn Phe Asn Tyr Asn Asp Pro Ile Asp Asn
Asn Asn Ile Ile Met Met Glu Pro Pro Phe Ala Arg Gly Thr Gly Arg
Tyr Tyr Lys Ala Phe Lys Ile Thr Asp Arg Ile Trp Ile Ile Pro Glu
Arg Tyr Thr Phe Gly Tyr Lys Pro Glu Asp Phe Asn Lys Ser Ser Gly
Ile Phe Asn Arg Asp Val Cys Glu Tyr Tyr Asp Pro Asp Tyr Leu Asn
Thr Asn Asp Lys Lys Asn Ile Phe Leu Gln Thr Met Ile Lys Leu Phe
Asn Arg Ile Lys Ser Lys Pro Leu Gly Glu Lys Leu Leu Glu Met Ile
Ile Asn Gly Ile Pro Tyr Leu Gly Asp Arg Arg Val Pro Leu Glu Glu
Phe Asn Thr Asn Ile Ala Ser Val Thr Val Asn Lys Leu Ile Ser Asn
Pro Gly Glu Val Glu Arg Lys Lys Gly Ile Phe Ala Asn Leu Ile Ile
Phe Gly Pro Gly Pro Val Leu Asn Glu Asn Glu Thr Ile Asp Ile Gly
Ile Gln Asn His Phe Ala Ser Arg Glu Gly Phe Gly Gly Ile Met Gln
Met Lys Phe Cys Pro Glu Tyr Val Ser Val Phe Asn Asn Val Gln Glu
Asn Lys Gly Ala Ser Ile Phe Asn Arg Arg Gly Tyr Phe Ser Asp Pro
Ala Leu Ile Leu Met His Glu Leu Ile His Val Leu His Gly Leu Tyr
Gly Ile Lys Val Asp Asp Leu Pro Ile Val Pro Asn Glu Lys Lys Phe
Phe Met Gln Ser Thr Asp Ala Ile Gln Ala Glu Glu Leu Tyr Thr Phe
Gly Gly Gln Asp Pro Ser Ile Ile Thr Pro Ser Thr Asp Lys Ser Ile
Tyr Asp Lys Val Leu Gln Asn Phe Arg Gly Ile Val Asp Arg Leu Asn
Lys Val Leu Val Cys Ile Ser Asp Pro Asn Ile Asn Ile Asn Ile Tyr
Lys Asn Lys Phe Lys Asp Lys Tyr Lys Phe Val Glu Asp Ser Glu Gly
Lys Tyr Ser Ile Asp Val Glu Ser Phe Asp Lys Leu Tyr Lys Ser Leu
Met Phe Gly Phe Thr Glu Thr Asn Ile Ala Glu Asn Tyr Lys Ile Lys
Thr Arg Ala Ser Tyr Phe Ser Asp Ser Leu Pro Pro Val Lys Ile Lys
Asn Leu Leu Asp Asn Glu Ile Tyr Thr Ile Glu Glu Gly Phe Asn Ile
Ser Asp Lys Asp Met Glu Lys Glu Tyr Arg Gly Gln Asn Lys Ala Ile
Asn Lys Gln Ala Tyr Glu Glu Ile Ser Lys Glu His Leu Ala Val Tyr
Lys Ile Gln Met Cys Lys Ser Val Lys Ala Pro Gly Ile Cys Ile Asp
Val Asp Asn Glu Asp Leu Phe Phe Ile Ala Asp Lys Asn Ser Phe Ser
Asp Asp Leu Ser Lys Asn Glu Arg Ile Glu Tyr Asn Thr Gln Ser Asn
Tyr Ile Glu Asn Asp Phe Pro Ile Asn Glu Leu Ile Leu Asp Thr Asp
Leu Ile Ser Lys Ile Glu Leu Pro Ser Glu Asn Thr Glu Ser Leu Thr
Asp Phe Asn Val Asp Val Pro Val Tyr Glu Lys Gln Pro Ala Ile Lys
Lys Ile Phe Thr Asp Glu Asn Thr Ile Phe Gln Tyr Leu Tyr Ser Gln
Thr Phe Pro Leu Asp Ile Arg Asp Ile Ser Leu Thr Ser Ser Phe Asp
Asp Ala Leu Leu Phe Ser Asn Lys Val Tyr Ser Phe Phe Ser Met Asp
Tyr Ile Lys Thr Ala Asn Lys Val Val Glu Ala Gly Leu Phe Ala Gly
Trp Val Lys Gln Ile Val Asn Asp Phe Val Ile Glu Ala Asn Lys Ser
Asn Thr Met Asp Lys Ile Ala Asp Ile Ser Leu Ile Val Pro Tyr Ile
Gly Leu Ala Leu Asn Val Gly Asn Glu Thr Ala Lys Gly Asn Phe Glu
Asn Ala Phe Glu Ile Ala Gly Ala Ser Ile Leu Leu Glu Phe Ile Pro
Glu Leu Leu Ile Pro Val Val Gly Ala Phe Leu Leu Glu Ser Tyr Ile
Asp Asn Lys Asn Lys Ile Ile Lys Thr Ile Asp Asn Ala Leu Thr Lys
Arg Asn Glu Lys Trp Ser Asp Met Tyr Gly Leu Ile Val Ala Gln Trp
Leu Ser Thr Val Asn Thr Gln Phe Tyr Thr Ile Lys Glu Gly Met Tyr
```

```
Lys Ala Leu Asn Tyr Gln Ala Gln Ala Leu Glu Glu Ile Ile Lys Tyr
Arg Tyr Asn Ile Tyr Ser Glu Lys Glu Lys Ser Asn Ile Asn Ile Asp
Phe Asn Asp Ile Asn Ser Lys Leu Asn Glu Gly Ile Asn Gln Ala Ile
Asp Asn Ile Asn Asn Phe Ile Asn Gly Cys Ser Val Ser Tyr Leu Met
Lys Lys Met Ile Pro Leu Ala Val Glu Lys Leu Leu Asp Phe Asp Asn
Thr Leu Lys Lys Asn Leu Leu Asn Tyr Ile Asp Glu Asn Lys Leu Tyr
Leu Ile Gly Ser Ala Glu Tyr Glu Lys Ser Lys Val Asn Lys Tyr Leu
Lys Thr Ile Met Pro Phe Asp Leu Ser Ile Tyr Thr Asn Asp Thr Ile
Leu Ile Glu Met Phe Asn Lys Tyr Asn Ser Glu Ile Leu Asn Asn Ile
Ile Leu Asn Leu Arg Tyr Lys Asp Asn Asn Leu Ile Asp Leu Ser Gly
Tyr Gly Ala Lys Val Glu Val Tyr Asp Gly Val Glu Leu Asn Asp Lys
Asn Gln Phe Lys Leu Thr Ser Ser Ala Asn Ser Lys Ile Arg Val Thr
Gln Asn Gln Asn Ile Ile Phe Asn Ser Val Phe Leu Asp Phe Ser Val
Ser Phe Trp Ile Arg Ile Pro Lys Tyr Lys Asn Asp Gly Ile Gln Asn
Tyr Ile His Asn Glu Tyr Thr Ile Ile Asn Cys Met Lys Asn Asn Ser
Gly Trp Lys Ile Ser Ile Arg Gly Asn Arg Ile Ile Trp Thr Leu Ile
Asp Ile Asn Gly Lys Thr Lys Ser Val Phe Phe Glu Tyr Asn Ile Arg
Glu Asp Ile Ser Glu Tyr Ile Asn Arg Trp Phe Phe Val Thr Ile Thr
Asn Asn Leu Asn Asn Ala Lys Ile Tyr Ile Asn Gly Lys Leu Glu Ser
Asn Thr Asp Ile Lys Asp Ile Arg Glu Val Ile Ala Asn Gly Glu Ile
Ile Phe Lys Leu Asp Gly Asp Ile Asp Arg Thr Gln Phe Ile Trp Met
Lys Tyr Phe Ser Ile Phe Asn Thr Glu Leu Ser Gln Ser Asn Ile Glu
Glu Arg Tyr Lys Ile Gln Ser Tyr Ser Glu Tyr Leu Lys Asp Phe Trp
Gly Asn Pro Leu Met Tyr Asn Lys Glu Tyr Tyr Met Phe Asn Ala Gly
Asn Lys Asn Ser Tyr Ile Lys Leu Lys Lys Asp Ser Pro Val Gly Glu
Ile Leu Thr Arg Ser Lys Tyr Asn Gln Asn Ser Lys Tyr Ile Asn Tyr
Arg Asp Leu Tyr Ile Gly Glu Lys Phe Ile Ile Arg Arg Lys Ser Asn
Ser Gln Ser Ile Asn Asp Asp Ile Val Arg Lys Glu Asp Tyr Ile Tyr
Leu Asp Phe Phe Asn Leu Asn Gln Glu Trp Arg Val Tyr Thr Tyr Lys
Tyr Phe Lys Lys Glu Glu Glu Lys Leu Phe Leu Ala Pro Ile Ser Asp
Ser Asp Glu Phe Tyr Asn Thr Ile Gln Ile Lys Glu Tyr Asp Glu Gln
Pro Thr Tyr Ser Cys Gln Leu Leu Phe Lys Lys Asp Glu Glu Ser Thr
Asp Glu Ile Gly Leu Ile Gly Ile His Arg Phe Tyr Glu Ser Gly Ile
Val Phe Glu Glu Tyr Lys Asp Tyr Phe Cys Ile Ser Lys Trp Tyr Leu
Lys Glu Val Lys Arg Lys Pro Tyr Asn Leu Lys Leu Gly Cys Asn Trp
Gln Phe Ile Pro Lys Asp Glu Gly Trp Thr Glu
```

```
Clostridium botulinum serotype C1
(1291 a.a.)
Met Pro Ile Thr Ile Asn Asn Phe Asn Tyr Ser Asp Pro Val Asp Asn
Lys Asn Ile Leu Tyr Leu Asp Thr His Leu Asn Thr Leu Ala Asn Glu
Pro Glu Lys Ala Phe Arg Ile Thr Gly Asn Ile Trp Val Ile Pro Asp
Arg Phe Ser Arg Asn Ser Asn Pro Asn Leu Asn Lys Pro Pro Arg Val
Thr Ser Pro Lys Ser Gly Tyr Tyr Asp Pro Asn Tyr Leu Ser Thr Asp
Ser Asp Lys Asp Pro Phe Leu Lys Glu Ile Ile Lys Leu Phe Lys Arg
Ile Asn Ser Arg Glu Ile Gly Glu Glu Leu Ile Tyr Arg Leu Ser Thr
Asp Ile Pro Phe Pro Gly Asn Asn Asn Thr Pro Ile Asn Thr Phe Asp
Phe Asp Val Asp Phe Asn Ser Val Asp Val Lys Thr Arg Gln Gly Asn
Asn Trp Val Lys Thr Gly Ser Ile Asn Pro Ser Val Ile Ile Thr Gly
Pro Arg Glu Asn Ile Ile Asp Pro Glu Thr Ser Thr Phe Lys Leu Thr
Asn Asn Thr Phe Ala Ala Gln Glu Gly Phe Gly Ala Leu Ser Ile Ile
Ser Ile Ser Pro Arg Phe Met Leu Thr Tyr Ser Asn Ala Thr Asn Asp
Val Gly Glu Gly Arg Phe Ser Lys Ser Glu Phe Cys Met Asp Pro Ile
Leu Ile Leu Met His Glu Leu Asn His Ala Met His Asn Leu Tyr Gly
Ile Ala Ile Pro Asn Asp Gln Thr Ile Ser Ser Val Thr Ser Asn Ile
Phe Tyr Ser Gln Tyr Asn Val Lys Leu Glu Tyr Ala Glu Ile Tyr Ala
Phe Gly Gly Pro Thr Ile Asp Leu Ile Pro Lys Ser Ala Arg Lys Tyr
Phe Glu Glu Lys Ala Leu Asp Tyr Tyr Arg Ser Ile Ala Lys Arg Leu
Asn Ser Ile Thr Thr Ala Asn Pro Ser Ser Phe Asn Lys Tyr Ile Gly
Glu Tyr Lys Gln Lys Leu Ile Arg Lys Tyr Arg Phe Val Val Glu Ser
Ser Gly Glu Val Thr Val Asn Arg Asn Lys Phe Val Glu Leu Tyr Asn
Glu Leu Thr Gln Ile Phe Thr Glu Phe Asn Tyr Ala Lys Ile Tyr Asn
Val Gln Asn Arg Lys Ile Tyr Leu Ser Asn Val Tyr Thr Pro Val Thr
Ala Asn Ile Leu Asp Asp Asn Val Tyr Asp Ile Gln Asn Gly Phe Asn
Ile Pro Lys Ser Asn Leu Asn Val Leu Phe Met Gly Gln Asn Leu Ser
Arg Asn Pro Ala Leu Arg Lys Val Asn Pro Glu Asn Met Leu Tyr Leu
Phe Thr Lys Phe Cys His Lys Ala Ile Asp Gly Arg Ser Leu Tyr Asn
Lys Thr Leu Asp Cys Arg Glu Leu Leu Val Lys Asn Thr Asp Leu Pro
Phe Ile Gly Asp Ile Ser Asp Val Lys Thr Asp Ile Phe Leu Arg Lys
Asp Ile Asn Glu Glu Thr Glu Val Ile Tyr Tyr Pro Asp Asn Val Ser
Val Asp Gln Val Ile Leu Ser Lys Asn Thr Ser Glu His Gly Gln Leu
Asp Leu Leu Tyr Pro Ser Ile Asp Ser Glu Ser Glu Ile Leu Pro Gly
Glu Asn Gln Val Phe Tyr Asp Asn Arg Thr Gln Asn Val Asp Tyr Leu
Asn Ser Tyr Tyr Tyr Leu Glu Ser Gln Lys Leu Ser Asp Asn Val Glu
Asp Phe Thr Phe Thr Arg Ser Ile Glu Glu Ala Leu Asp Asn Ser Ala
Lys Val Tyr Thr Tyr Phe Pro Thr Leu Ala Asn Lys Val Asn Ala Gly
Val Gln Gly Gly Leu Phe Leu Met Trp Ala Asn Asp Val Val Glu Asp
Phe Thr Thr Asn Ile Leu Arg Lys Asp Thr Leu Asp Lys Ile Ser Asp
Val Ser Ala Ile Ile Pro Tyr Ile Gly Pro Ala Leu Asn Ile Ser Asn
Ser Val Arg Arg Gly Asn Phe Thr Glu Ala Phe Ala Val Thr Gly Val
Thr Ile Leu Leu Glu Ala Phe Pro Glu Phe Thr Ile Pro Ala Leu Gly
Ala Phe Val Ile Tyr Ser Lys Val Gln Glu Arg Asn Glu Ile Ile Lys
Thr Ile Asp Asn Cys Leu Glu Gln Arg Ile Lys Arg Trp Lys Asp Ser
Tyr Glu Trp Met Met Gly Thr Trp Leu Ser Arg Ile Ile Thr Gln Phe
Asn Asn Ile Ser Tyr Gln Met Tyr Asp Ser Leu Asn Tyr Gln Ala Gly
```

```
Ala Ile Lys Ala Lys Ile Asp Leu Glu Tyr Lys Lys Tyr Ser Gly Ser
Asp Lys Glu Asn Ile Lys Ser Gln Val Glu Asn Leu Lys Asn Ser Leu
Asp Val Lys Ile Ser Glu Ala Met Asn Asn Ile Asn Lys Phe Ile Arg
Glu Cys Ser Val Thr Tyr Leu Phe Lys Asn Met Leu Pro Lys Val Ile
Asp Glu Leu Asn Glu Phe Asp Arg Asn Thr Lys Ala Lys Leu Ile Asn
Leu Ile Asp Ser His Asn Ile Ile Leu Val Gly Glu Val Asp Lys Leu
Lys Ala Lys Val Asn Asn Ser Phe Gln Asn Thr Ile Pro Phe Asn Ile
Phe Ser Tyr Thr Asn Asn Ser Leu Leu Lys Asp Ile Ile Asn Glu Tyr
Phe Asn Asn Ile Asn Asp Ser Lys Ile Leu Ser Leu Gln Asn Arg Lys
Asn Thr Leu Val Asp Thr Ser Gly Tyr Asn Ala Glu Val Ser Glu Glu
Gly Asp Val Gln Leu Asn Pro Ile Phe Pro Phe Asp Phe Lys Leu Gly
Ser Ser Gly Glu Asp Arg Gly Lys Val Ile Val Thr Gln Asn Glu Asn
Ile Val Tyr Asn Ser Met Tyr Glu Ser Phe Ser Ile Ser Phe Trp Ile
Arg Ile Asn Lys Trp Val Ser Asn Leu Pro Gly Tyr Thr Ile Ile Asp
Ser Val Lys Asn Asn Ser Gly Trp Ser Ile Gly Ile Ile Ser Asn Phe
Leu Val Phe Thr Leu Lys Gln Asn Glu Asp Ser Glu Gln Ser Ile Asn
Phe Ser Tyr Asp Ile Ser Asn Asn Ala Pro Gly Tyr Asn Lys Trp Phe
Phe Val Thr Val Thr Asn Asn Met Met Gly Asn Met Lys Ile Tyr Ile
Asn Gly Lys Leu Ile Asp Thr Ile Lys Val Lys Glu Leu Thr Gly Ile
Asn Phe Ser Lys Thr Ile Thr Phe Glu Ile Asn Lys Ile Pro Asp Thr
Gly Leu Ile Thr Ser Asp Ser Asp Asn Ile Asn Met Trp Ile Arg Asp
Phe Tyr Ile Phe Ala Lys Glu Leu Asp Gly Lys Asp Ile Asn Ile Leu
Phe Asn Ser Leu Gln Tyr Thr Asn Val Val Lys Asp Tyr Trp Gly Asn
Asp Leu Arg Tyr Asn Lys Glu Tyr Tyr Met Val Asn Ile Asp Tyr Leu
Asn Arg Tyr Met Tyr Ala Asn Ser Arg Gln Ile Val Phe Asn Thr Arg
Arg Asn Asn Asn Asp Phe Asn Glu Gly Tyr Lys Ile Ile Ile Lys Arg
Ile Arg Gly Asn Thr Asn Asp Thr Arg Val Arg Gly Gly Asp Ile Leu
Tyr Phe Asp Met Thr Ile Asn Asn Lys Ala Tyr Asn Leu Phe Met Lys
Asn Glu Thr Met Tyr Ala Asp Asn His Ser Thr Glu Asp Ile Tyr Ala
Ile Gly Leu Arg Glu Gln Thr Lys Asp Ile Asn Asp Asn Ile Ile Phe
Gln Ile Gln Pro Met Asn Asn Thr Tyr Tyr Tyr Ala Ser Gln Ile Phe
Lys Ser Asn Phe Asn Gly Glu Asn Ile Ser Gly Ile Cys Ser Ile Gly
Thr Tyr Arg Phe Arg Leu Gly Gly Asp Trp Tyr Arg His Asn Tyr Leu
Val Pro Thr Val Lys Gln Gly Asn Tyr Ala Ser Leu Leu Glu Ser Thr
Ser Thr His Trp Gly Phe Val Pro Val Ser Glu
```

Clostridium botulinum serotype D
(1276 a.a.)

```
Met Thr Trp Pro Val Lys Asp Phe Asn Tyr Ser Asp Pro Val Asn Asp
Asn Asp Ile Leu Tyr Leu Arg Ile Pro Gln Asn Lys Leu Ile Thr Thr
Pro Val Lys Ala Phe Met Ile Thr Gln Asn Ile Trp Val Ile Pro Glu
Arg Phe Ser Ser Asp Thr Asn Pro Ser Leu Ser Lys Pro Pro Arg Pro
Thr Ser Lys Tyr Gln Ser Tyr Tyr Asp Pro Ser Tyr Leu Ser Thr Asp
Glu Gln Lys Asp Thr Phe Leu Lys Gly Ile Ile Lys Leu Phe Lys Arg
Ile Asn Glu Arg Asp Ile Gly Lys Lys Leu Ile Asn Tyr Leu Val Val
Gly Ser Pro Phe Met Gly Asp Ser Ser Thr Pro Glu Asp Thr Phe Asp
Phe Thr Arg His Thr Thr Asn Ile Ala Val Glu Lys Phe Glu Asn Gly
Ser Trp Lys Val Thr Asn Ile Ile Thr Pro Ser Val Leu Ile Phe Gly
Pro Leu Pro Asn Ile Leu Asp Tyr Thr Ala Ser Leu Thr Leu Gln Gly
Gln Gln Ser Asn Pro Ser Phe Glu Gly Phe Gly Thr Leu Ser Ile Leu
Lys Val Ala Pro Glu Phe Leu Leu Thr Phe Ser Asp Val Thr Ser Asn
Gln Ser Ser Ala Val Leu Gly Lys Ser Ile Phe Cys Met Asp Pro Val
Ile Ala Leu Met His Glu Leu Thr His Ser Leu His Gln Leu Tyr Gly
Ile Asn Ile Pro Ser Asp Lys Arg Ile Arg Pro Gln Val Ser Glu Gly
Phe Phe Ser Gln Asp Gly Pro Asn Val Gln Phe Glu Glu Leu Tyr Thr
Phe Gly Gly Leu Asp Val Glu Ile Ile Pro Gln Ile Glu Arg Ser Gln
Leu Arg Glu Lys Ala Leu Gly His Tyr Lys Asp Ile Ala Lys Arg Leu
Asn Asn Ile Asn Lys Thr Ile Pro Ser Ser Trp Ile Ser Asn Ile Asp
Lys Tyr Lys Lys Ile Phe Ser Glu Lys Tyr Asn Phe Asp Lys Asp Asn
Thr Gly Asn Phe Val Val Asn Ile Asp Lys Phe Asn Ser Leu Tyr Ser
Asp Leu Thr Asn Val Met Ser Glu Val Val Tyr Ser Ser Gln Tyr Asn
Val Lys Asn Arg Thr His Tyr Phe Ser Arg His Tyr Leu Pro Val Phe
Ala Asn Ile Leu Asp Asp Asn Ile Tyr Thr Ile Arg Asp Gly Phe Asn
Leu Thr Asn Lys Gly Phe Asn Ile Glu Asn Ser Gly Gln Asn Ile Glu
Arg Asn Pro Ala Leu Gln Lys Leu Ser Ser Glu Ser Val Val Asp Leu
Phe Thr Lys Val Cys Leu Arg Leu Thr Lys Asn Ser Arg Asp Asp Ser
Thr Cys Ile Lys Val Lys Asn Asn Arg Leu Pro Tyr Val Ala Asp Lys
Asp Ser Ile Ser Gln Glu Ile Phe Glu Asn Lys Ile Ile Thr Asp Glu
Thr Asn Val Gln Asn Tyr Ser Asp Lys Phe Ser Leu Asp Glu Ser Ile
Leu Asp Gly Gln Val Pro Ile Asn Pro Glu Ile Val Asp Pro Leu Leu
Pro Asn Val Asn Met Glu Pro Leu Asn Leu Pro Gly Glu Glu Ile Val
Phe Tyr Asp Asp Ile Thr Lys Tyr Val Asp Tyr Leu Asn Ser Tyr Tyr
Tyr Leu Glu Ser Gln Lys Leu Ser Asn Asn Val Glu Asn Ile Thr Leu
Thr Thr Ser Val Glu Glu Ala Leu Gly Tyr Ser Asn Lys Ile Tyr Thr
Phe Leu Pro Ser Leu Ala Glu Lys Val Asn Lys Gly Val Gln Ala Gly
Leu Phe Leu Asn Trp Ala Asn Glu Val Val Glu Asp Phe Thr Thr Asn
Ile Met Lys Lys Asp Thr Leu Asp Lys Ile Ser Asp Val Ser Val Ile
Ile Pro Tyr Ile Gly Pro Ala Leu Asn Ile Gly Asn Ser Ala Leu Arg
Gly Asn Phe Asn Gln Ala Phe Ala Thr Ala Gly Val Ala Phe Leu Leu
Glu Gly Phe Pro Glu Phe Thr Ile Pro Ala Leu Gly Val Phe Thr Phe
Tyr Ser Ser Ile Gln Glu Arg Glu Lys Ile Ile Lys Thr Ile Glu Asn
Cys Leu Glu Gln Arg Val Lys Arg Trp Lys Asp Ser Tyr Gln Trp Met
Val Ser Asn Trp Leu Ser Arg Ile Thr Thr Gln Phe Asn His Ile Asn
```

```
Tyr Gln Met Tyr Asp Ser Leu Ser Tyr Gln Ala Asp Ala Ile Lys Ala
Lys Ile Asp Leu Glu Tyr Lys Lys Tyr Ser Gly Ser Asp Lys Glu Asn
Ile Lys Ser Gln Val Glu Asn Leu Lys Asn Ser Leu Asp Val Lys Ile
Ser Glu Ala Met Asn Asn Ile Asn Lys Phe Ile Arg Glu Cys Ser Val
Thr Tyr Leu Phe Lys Asn Met Leu Pro Lys Val Ile Asp Glu Leu Asn
Lys Phe Asp Leu Arg Thr Lys Thr Glu Leu Ile Asn Leu Ile Asp Ser
His Asn Ile Ile Leu Val Gly Glu Val Asp Arg Leu Lys Ala Lys Val
Asn Glu Ser Phe Glu Asn Thr Met Pro Phe Asn Ile Phe Ser Tyr Thr
Asn Asn Ser Leu Leu Lys Asp Ile Ile Asn Glu Tyr Phe Asn Ser Ile
Asn Asp Ser Lys Ile Leu Ser Leu Gln Asn Lys Lys Asn Ala Leu Val
Asp Thr Ser Gly Tyr Asn Ala Glu Val Arg Val Gly Asp Asn Val Gln
Leu Asn Thr Ile Tyr Thr Asn Asp Phe Lys Leu Ser Ser Ser Gly Asp
Lys Ile Ile Val Asn Leu Asn Asn Asn Ile Leu Tyr Ser Ala Ile Tyr
Glu Asn Ser Ser Val Ser Phe Trp Ile Lys Ile Ser Lys Asp Leu Thr
Asn Ser His Asn Glu Tyr Thr Ile Ile Asn Ser Ile Glu Gln Asn Ser
Gly Trp Lys Leu Cys Ile Arg Asn Gly Asn Ile Glu Trp Ile Leu Gln
Asp Val Asn Arg Lys Tyr Lys Ser Leu Ile Phe Asp Tyr Ser Glu Ser
Leu Ser His Thr Gly Tyr Thr Asn Lys Trp Phe Phe Val Thr Ile Thr
Asn Asn Ile Met Gly Tyr Met Lys Leu Tyr Ile Asn Gly Glu Leu Lys
Gln Ser Gln Lys Ile Glu Asp Leu Asp Glu Val Lys Leu Asp Lys Thr
Ile Val Phe Gly Ile Asp Glu Asn Ile Asp Glu Asn Gln Met Leu Trp
Ile Arg Asp Phe Asn Ile Phe Ser Lys Glu Leu Ser Asn Glu Asp Ile
Asn Ile Val Tyr Glu Gly Gln Ile Leu Arg Asn Val Ile Lys Asp Tyr
Trp Gly Asn Pro Leu Lys Phe Asp Thr Glu Tyr Tyr Ile Ile Asn Asp
Asn Tyr Ile Asp Arg Tyr Ile Ala Pro Glu Ser Asn Val Leu Val Leu
Val Gln Tyr Pro Asp Arg Ser Lys Leu Tyr Thr Gly Asn Pro Ile Thr
Ile Lys Ser Val Ser Asp Lys Asn Pro Tyr Ser Arg Ile Leu Asn Gly
Asp Asn Ile Ile Leu His Met Leu Tyr Asn Ser Arg Lys Tyr Met Ile
Ile Arg Asp Thr Asp Thr Ile Tyr Ala Thr Gln Gly Gly Glu Cys Ser
Gln Asn Cys Val Tyr Ala Leu Lys Leu Gln Ser Asn Leu Gly Asn Tyr
Gly Ile Gly Ile Phe Ser Ile Lys Asn Ile Val Ser Lys Asn Lys Tyr
Cys Ser Gln Ile Phe Ser Ser Phe Arg Glu Asn Thr Met Leu Leu Ala
Asp Ile Tyr Lys Pro Trp Arg Phe Ser Phe Lys Asn Ala Tyr Thr Pro
Val Ala Val Thr Asn Tyr Glu Thr Lys Leu Leu Ser Thr Ser Ser Phe
Trp Lys Phe Ile Ser Arg Asp Pro Gly Trp Val Glu
```

Clostridium botulinum serotype E
(1252 a.a.)

```
Met Pro Lys Ile Asn Ser Phe Asn Tyr Asn Asp Pro Val Asn Asp Arg
Thr Ile Leu Tyr Ile Lys Pro Gly Gly Cys Gln Glu Phe Tyr Lys Ser
Phe Asn Ile Met Lys Asn Ile Trp Ile Ile Pro Glu Arg Asn Val Ile
Gly Thr Thr Pro Gln Asp Phe His Pro Pro Thr Ser Leu Lys Asn Gly
Asp Ser Ser Tyr Tyr Asp Pro Asn Tyr Leu Gln Ser Asp Glu Glu Lys
Asp Arg Phe Leu Lys Ile Val Thr Lys Ile Phe Asn Arg Ile Asn Asn
Asn Leu Ser Gly Gly Ile Leu Leu Glu Glu Leu Ser Lys Ala Asn Pro
Tyr Leu Gly Asn Asp Asn Thr Pro Asp Asn Gln Phe His Ile Gly Asp
Ala Ser Ala Val Glu Ile Lys Phe Ser Asn Gly Ser Gln Asp Ile Leu
Leu Pro Asn Val Ile Ile Met Gly Ala Glu Pro Asp Leu Phe Glu Thr
Asn Ser Ser Asn Ile Ser Leu Arg Asn Asn Tyr Met Pro Ser Asn His
Gly Phe Gly Ser Ile Ala Ile Val Thr Phe Ser Pro Glu Tyr Ser Phe
Arg Phe Asn Asp Asn Ser Met Asn Glu Phe Ile Gln Asp Pro Ala Leu
Thr Leu Met His Glu Leu Ile His Ser Leu His Gly Leu Tyr Gly Ala
Lys Gly Ile Thr Thr Lys Tyr Thr Ile Thr Gln Lys Gln Asn Pro Leu
Ile Thr Asn Ile Arg Gly Thr Asn Ile Glu Glu Phe Leu Thr Phe Gly
Gly Thr Asp Leu Asn Ile Ile Thr Ser Ala Gln Ser Asn Asp Ile Tyr
Thr Asn Leu Leu Ala Asp Tyr Lys Lys Ile Ala Ser Lys Leu Ser Lys
Val Gln Val Ser Asn Pro Leu Leu Asn Pro Tyr Lys Asp Val Phe Glu
Ala Lys Tyr Gly Leu Asp Lys Asp Ala Ser Gly Ile Tyr Ser Val Asn
Ile Asn Lys Phe Asn Asp Ile Phe Lys Lys Leu Tyr Ser Phe Thr Glu
Phe Asp Leu Ala Thr Lys Phe Gln Val Lys Cys Arg Gln Thr Tyr Ile
Gly Gln Tyr Lys Tyr Phe Lys Leu Ser Asn Leu Leu Asn Asp Ser Ile
Tyr Asn Ile Ser Glu Gly Tyr Asn Ile Asn Asn Leu Lys Val Asn Phe
Arg Gly Gln Asn Ala Asn Leu Asn Pro Arg Ile Ile Thr Pro Ile Thr
Gly Arg Gly Leu Val Lys Lys Ile Ile Arg Phe Cys Lys Asn Ile Val
Ser Val Lys Gly Ile Arg Lys Ser Ile Cys Ile Glu Ile Asn Asn Gly
Glu Leu Phe Phe Val Ala Ser Glu Asn Ser Tyr Asn Asp Asp Asn Ile
Asn Thr Pro Lys Glu Ile Asp Asp Thr Val Thr Ser Asn Asn Asn Tyr
Glu Asn Asp Leu Asp Gln Val Ile Leu Asn Phe Asn Ser Glu Ser Ala
Pro Gly Leu Ser Asp Glu Lys Leu Asn Leu Thr Ile Gln Asn Asp Ala
Tyr Ile Pro Lys Tyr Asp Ser Asn Gly Thr Ser Asp Ile Glu Gln His
Asp Val Asn Glu Leu Asn Val Phe Phe Tyr Leu Asp Ala Gln Lys Val
Pro Glu Gly Glu Asn Asn Val Asn Leu Thr Ser Ser Ile Asp Thr Ala
Leu Leu Glu Gln Pro Lys Ile Tyr Thr Phe Phe Ser Ser Glu Phe Ile
Asn Asn Val Asn Lys Pro Val Gln Ala Ala Leu Phe Val Ser Trp Ile
Gln Gln Val Leu Val Asp Phe Thr Thr Glu Ala Asn Gln Lys Ser Thr
Val Asp Lys Ile Ala Asp Ile Ser Ile Val Val Pro Tyr Ile Gly Leu
Ala Leu Asn Ile Gly Asn Glu Ala Gln Lys Gly Asn Phe Lys Asp Ala
Leu Glu Leu Leu Gly Ala Gly Ile Leu Leu Glu Phe Glu Pro Glu Leu
Leu Ile Pro Thr Ile Leu Val Phe Thr Ile Lys Ser Phe Leu Gly Ser
Ser Asp Asn Lys Asn Lys Val Ile Lys Ala Ile Asn Asn Ala Leu Lys
Glu Arg Asp Glu Lys Trp Lys Glu Val Tyr Ser Phe Ile Val Ser Asn
Trp Met Thr Lys Ile Asn Thr Gln Phe Asn Lys Arg Lys Glu Gln Met
Tyr Gln Ala Leu Gln Asn Gln Val Asn Ala Ile Lys Thr Ile Ile Glu
Ser Lys Tyr Asn Ser Tyr Thr Leu Glu Glu Lys Asn Glu Leu Thr Asn
```

```
Lys Tyr Asp Ile Lys Gln Ile Glu Asn Glu Leu Asn Gln Lys Val Ser
Ile Ala Met Asn Asn Ile Asp Arg Phe Leu Thr Glu Ser Ser Ile Ser
Tyr Leu Met Lys Leu Ile Asn Glu Val Lys Ile Asn Lys Leu Arg Glu
Tyr Asp Glu Asn Val Lys Thr Tyr Leu Leu Asn Tyr Ile Ile Gln His
Gly Ser Ile Leu Gly Glu Ser Gln Gln Glu Leu Asn Ser Met Val Thr
Asp Thr Leu Asn Asn Ser Ile Pro Phe Lys Leu Ser Ser Tyr Thr Asp
Asp Lys Ile Leu Ile Ser Tyr Phe Asn Lys Phe Phe Lys Arg Ile Lys
Ser Ser Ser Val Leu Asn Met Arg Tyr Lys Asn Asp Lys Tyr Val Asp
Thr Ser Gly Tyr Asp Ser Asn Ile Asn Ile Asn Gly Asp Val Tyr Lys
Tyr Pro Thr Asn Lys Asn Gln Phe Gly Ile Tyr Asn Asp Lys Leu Ser
Glu Val Asn Ile Ser Gln Asn Asp Tyr Ile Ile Tyr Asp Asn Lys Tyr
Lys Asn Phe Ser Ile Ser Phe Trp Val Arg Ile Pro Asn Tyr Asp Asn
Lys Ile Val Asn Val Asn Asn Glu Tyr Thr Ile Ile Asn Cys Met Arg
Asp Asn Asn Ser Gly Trp Lys Val Ser Leu Asn His Asn Glu Ile Ile
Trp Thr Leu Gln Asp Asn Ala Gly Ile Asn Gln Lys Leu Ala Phe Asn
Tyr Gly Asn Ala Asn Gly Ile Ser Asp Tyr Ile Asn Lys Trp Ile Phe
Val Thr Ile Thr Asn Asp Arg Leu Gly Asp Ser Lys Leu Tyr Ile Asn
Gly Asn Leu Ile Asp Gln Lys Ser Ile Leu Asn Leu Gly Asn Ile His
Val Ser Asp Asn Ile Leu Phe Lys Ile Val Asn Cys Ser Tyr Thr Arg
Tyr Ile Gly Ile Arg Tyr Phe Asn Ile Phe Asp Lys Glu Leu Asp Glu
Thr Glu Ile Gln Thr Leu Tyr Ser Asn Glu Pro Asn Thr Asn Ile Leu
Lys Asp Phe Trp Gly Asn Tyr Leu Leu Tyr Asp Lys Glu Tyr Tyr Leu
Leu Asn Val Leu Lys Pro Asn Asn Phe Ile Asp Arg Arg Lys Asp Ser
Thr Leu Ser Ile Asn Asn Ile Arg Ser Thr Ile Leu Leu Ala Asn Arg
Leu Tyr Ser Gly Ile Lys Val Lys Ile Gln Arg Val Asn Asn Ser Ser
Thr Asn Asp Asn Leu Val Arg Lys Asn Asp Gln Val Tyr Ile Asn Phe
Val Ala Ser Lys Thr His Leu Phe Pro Leu Tyr Ala Asp Thr Ala Thr
Thr Asn Lys Glu Lys Thr Ile Lys Ile Ser Ser Ser Gly Asn Arg Phe
Asn Gln Val Val Val Met Asn Ser Val Gly Asn Asn Cys Thr Met Asn
Phe Lys Asn Asn Asn Gly Asn Asn Ile Gly Leu Leu Gly Phe Lys Ala
Asp Thr Val Val Ala Ser Thr Trp Tyr Tyr Thr His Met Arg Asp His
Thr Asn Ser Asn Gly Cys Phe Trp Asn Phe Ile Ser Glu Glu His Gly
Trp Gln Glu Lys
```

<div align="center">

*FIG. 18 (cont.)*

</div>

*FIG.* *19*

Clostridium botulinum serotype F
(1274 a.a.)

```
Met Pro Val Ala Ile Asn Ser Phe Asn Tyr Asn Asp Pro Val Asn Asp
Asp Thr Ile Leu Tyr Met Gln Ile Pro Tyr Glu Glu Lys Ser Lys Lys
Tyr Tyr Lys Ala Phe Glu Ile Met Arg Asn Val Trp Ile Ile Pro Glu
Arg Asn Thr Ile Gly Thr Asn Pro Ser Asp Phe Asp Pro Pro Ala Ser
Leu Lys Asn Gly Ser Ser Ala Tyr Tyr Asp Pro Asn Tyr Leu Thr Thr
Asp Ala Glu Lys Asp Arg Tyr Leu Lys Thr Thr Ile Lys Leu Phe Lys
Arg Ile Asn Ser Asn Pro Ala Gly Lys Val Leu Leu Gln Glu Ile Ser
Tyr Ala Lys Pro Tyr Leu Gly Asn Asp His Thr Pro Ile Asp Glu Phe
Ser Pro Val Thr Arg Thr Thr Ser Val Asn Ile Lys Leu Ser Thr Asn
Val Glu Ser Ser Met Leu Leu Asn Leu Leu Val Leu Gly Ala Gly Pro
Asp Ile Phe Glu Ser Cys Cys Tyr Pro Val Arg Lys Leu Ile Asp Pro
Asp Val Val Tyr Asp Pro Ser Asn Tyr Gly Phe Gly Ser Ile Asn Ile
Val Thr Phe Ser Pro Glu Tyr Glu Tyr Thr Phe Asn Asp Ile Ser Gly
Gly His Asn Ser Ser Thr Glu Ser Phe Ile Ala Asp Pro Ala Ile Ser
Leu Ala His Glu Leu Ile His Ala Leu His Gly Leu Tyr Gly Ala Arg
Gly Val Thr Tyr Glu Glu Thr Ile Glu Val Lys Gln Ala Pro Leu Met
Ile Ala Glu Lys Pro Ile Arg Leu Glu Glu Phe Leu Thr Phe Gly Gly
Gln Asp Leu Asn Ile Ile Thr Ser Ala Met Lys Glu Lys Ile Tyr Asn
Asn Leu Leu Ala Asn Tyr Glu Lys Ile Ala Thr Arg Leu Ser Glu Val
Asn Ser Ala Pro Pro Glu Tyr Asp Ile Asn Glu Tyr Lys Asp Tyr Phe
Gln Trp Lys Tyr Gly Leu Asp Lys Asn Ala Asp Gly Ser Tyr Thr Val
Asn Glu Asn Lys Phe Asn Glu Ile Tyr Lys Lys Leu Tyr Ser Phe Thr
Glu Ser Asp Leu Ala Asn Lys Phe Lys Val Lys Cys Arg Asn Thr Tyr
Phe Ile Lys Tyr Glu Phe Leu Lys Val Pro Asn Leu Leu Asp Asp Asp
Ile Tyr Thr Val Ser Glu Gly Phe Asn Ile Gly Asn Leu Ala Val Asn
Asn Arg Gly Gln Ser Ile Lys Leu Asn Pro Lys Ile Ile Asp Ser Ile
Pro Asp Lys Gly Leu Val Glu Lys Ile Val Lys Phe Cys Lys Ser Val
Ile Pro Arg Lys Gly Thr Lys Ala Pro Pro Arg Leu Cys Ile Arg Val
Asn Asn Ser Glu Leu Phe Phe Val Ala Ser Glu Ser Ser Tyr Asn Glu
Asn Asp Ile Asn Thr Pro Lys Glu Ile Asp Asp Thr Thr Asn Leu Asn
Asn Asn Tyr Arg Asn Asn Leu Asp Glu Val Ile Leu Asp Tyr Asn Ser
Gln Thr Ile Pro Gln Ile Ser Asn Arg Thr Leu Asn Thr Leu Val Gln
Asp Asn Ser Tyr Val Pro Arg Tyr Asp Ser Asn Gly Thr Ser Glu Ile
Glu Glu Tyr Asp Val Val Asp Phe Asn Val Phe Phe Tyr Leu His Ala
Gln Lys Val Pro Glu Gly Glu Thr Asn Ile Ser Leu Thr Ser Ser Ile
Asp Thr Ala Leu Leu Glu Glu Ser Lys Asp Ile Phe Phe Ser Ser Glu
Phe Ile Asp Thr Ile Asn Lys Pro Val Asn Ala Ala Leu Phe Ile Asp
Trp Ile Ser Lys Val Ile Arg Asp Phe Thr Thr Glu Ala Thr Gln Lys
Ser Thr Val Asp Lys Ile Ala Asp Ile Ser Leu Ile Val Pro Tyr Val
Gly Leu Ala Leu Asn Ile Ile Ile Glu Ala Glu Lys Gly Asn Phe Glu
Glu Ala Phe Glu Leu Leu Gly Val Gly Ile Leu Leu Glu Phe Val Pro
Glu Leu Thr Ile Pro Val Ile Leu Val Phe Thr Ile Lys Ser Tyr Ile
Asp Ser Tyr Glu Asn Lys Asn Lys Ala Ile Lys Ala Ile Asn Asn Ser
Leu Ile Glu Arg Glu Ala Lys Trp Lys Glu Ile Tyr Ser Trp Ile Val
Ser Asn Trp Leu Thr Arg Ile Asn Thr Gln Phe Asn Lys Arg Lys Glu
```

```
Gln Met Tyr Gln Ala Leu Gln Asn Gln Val Asp Ala Ile Lys Thr Ala
Ile Glu Tyr Lys Tyr Asn Asn Tyr Thr Ser Asp Glu Lys Asn Arg Leu
Glu Ser Glu Tyr Asn Ile Asn Asn Ile Glu Glu Glu Leu Asn Lys Lys
Val Ser Leu Ala Met Lys Asn Ile Glu Arg Phe Met Thr Glu Ser Ser
Ile Ser Tyr Leu Met Lys Leu Ile Asn Glu Ala Lys Val Gly Lys Leu
Lys Lys Tyr Asp Asn His Val Lys Ser Asp Leu Leu Asn Tyr Ile Leu
Asp His Arg Ser Ile Leu Gly Glu Gln Thr Asn Glu Leu Ser Asp Leu
Val Thr Ser Thr Leu Asn Ser Ser Ile Pro Phe Glu Leu Ser Ser Tyr
Thr Asn Asp Lys Ile Leu Ile Ile Tyr Phe Asn Arg Leu Tyr Lys Lys
Ile Lys Asp Ser Ser Ile Leu Asp Met Arg Tyr Glu Asn Asn Lys Phe
Ile Asp Ile Ser Gly Tyr Gly Ser Asn Ile Ser Ile Asn Gly Asn Val
Tyr Ile Tyr Ser Thr Asn Arg Asn Gln Phe Gly Ile Tyr Asn Ser Arg
Leu Ser Glu Val Asn Ile Ala Gln Asn Asn Asp Ile Ile Tyr Asn Ser
Arg Tyr Gln Asn Phe Ser Ile Ser Phe Trp Val Arg Ile Pro Lys His
Tyr Lys Pro Met Asn His Asn Arg Glu Tyr Thr Ile Ile Asn Cys Met
Gly Asn Asn Asn Ser Gly Trp Lys Ile Ser Leu Arg Thr Val Arg Asp
Cys Glu Ile Ile Trp Thr Leu Gln Asp Thr Ser Gly Asn Lys Glu Asn
Leu Ile Phe Arg Tyr Glu Glu Leu Asn Arg Ile Ser Asn Tyr Ile Asn
Lys Trp Ile Phe Val Thr Ile Thr Asn Asn Arg Leu Gly Asn Ser Arg
Ile Tyr Ile Asn Gly Asn Leu Ile Val Glu Lys Ser Ile Ser Asn Leu
Gly Asp Ile His Val Ser Asp Asn Ile Leu Phe Lys Ile Val Gly Cys
Asp Asp Glu Thr Tyr Val Gly Ile Arg Tyr Phe Lys Val Phe Asn Thr
Glu Leu Asp Lys Thr Glu Ile Glu Thr Leu Tyr Ser Asn Glu Pro Asp
Pro Ser Ile Leu Lys Asn Tyr Trp Gly Asn Tyr Leu Leu Tyr Asn Lys
Lys Tyr Tyr Leu Phe Asn Leu Leu Arg Lys Asp Lys Tyr Ile Thr Leu
Asn Ser Gly Ile Leu Asn Ile Asn Gln Gln Arg Gly Val Thr Glu Gly
Ser Val Phe Leu Asn Tyr Lys Leu Tyr Glu Gly Val Glu Val Ile Ile
Arg Lys Asn Gly Pro Ile Asp Ile Ser Asn Thr Asp Asn Phe Val Arg
Lys Asn Asp Leu Ala Tyr Ile Asn Val Val Asp Arg Gly Val Glu Tyr
Arg Leu Tyr Ala Asp Thr Lys Ser Glu Lys Glu Lys Ile Ile Arg Thr
Ser Asn Leu Asn Asp Ser Leu Gly Gln Ile Ile Val Met Asp Ser Ile
Gly Asn Asn Cys Thr Met Asn Phe Gln Asn Asn Asn Gly Ser Asn Ile
Gly Leu Leu Gly Phe His Ser Asn Asn Leu Val Ala Ser Ser Trp Tyr
Tyr Asn Asn Ile Arg Arg Asn Thr Ser Ser Asn Gly Cys Phe Trp Ser
Ser Ile Ser Lys Glu Asn Gly Trp Lys Glu
```

Clostridium botulinum serotype G
(1297 a.a.)

```
Met Pro Val Asn Ile Lys Asn Phe Asn Tyr Asn Asp Pro Ile Asn Asn
Asp Asp Ile Ile Met Met Glu Pro Phe Asn Asp Pro Gly Pro Gly Thr
Tyr Tyr Lys Ala Phe Arg Ile Ile Asp Arg Ile Trp Ile Val Pro Glu
Arg Phe Thr Tyr Gly Phe Gln Pro Asp Gln Phe Asn Ala Ser Thr Gly
Val Phe Ser Lys Asp Val Tyr Glu Tyr Tyr Asp Pro Thr Tyr Leu Lys
Thr Asp Ala Glu Lys Asp Lys Phe Leu Lys Thr Met Ile Lys Leu Phe
Asn Arg Ile Asn Ser Lys Pro Ser Gly Gln Arg Leu Leu Asp Met Ile
Val Asp Ala Ile Pro Tyr Leu Gly Asn Ala Ser Thr Pro Pro Asp Lys
Phe Ala Ala Asn Val Ala Asn Val Ser Ile Asn Lys Lys Ile Ile Gln
Pro Gly Ala Glu Asp Gln Ile Lys Gly Leu Met Thr Asn Leu Ile Ile
Phe Gly Pro Gly Pro Val Leu Ser Asp Asn Phe Thr Asp Ser Met Ile
Met Asn Gly His Ser Pro Ile Ser Glu Gly Phe Gly Ala Arg Met Met
Ile Arg Phe Cys Pro Ser Cys Leu Asn Val Phe Asn Asn Val Gln Glu
Asn Lys Asp Thr Ser Ile Phe Ser Arg Arg Ala Tyr Phe Ala Asp Pro
Ala Leu Thr Leu Met His Glu Leu Ile His Val Leu His Gly Leu Tyr
Gly Ile Lys Ile Ser Asn Leu Pro Ile Thr Pro Asn Thr Lys Glu Phe
Phe Met Gln His Ser Asp Pro Val Gln Ala Glu Glu Leu Tyr Thr Phe
Gly Gly His Asp Pro Ser Val Ile Ser Pro Ser Thr Asp Met Asn Ile
Tyr Asn Lys Ala Leu Gln Asn Phe Gln Asp Ile Ala Asn Arg Leu Asn
Ile Val Ser Ser Ala Gln Gly Ser Gly Ile Asp Ile Ser Leu Tyr Lys
Gln Ile Tyr Lys Asn Lys Tyr Asp Phe Val Glu Asp Pro Asn Gly Lys
Tyr Ser Val Asp Lys Asp Lys Phe Asp Lys Leu Tyr Lys Ala Leu Met
Phe Gly Phe Thr Glu Thr Asn Leu Ala Gly Glu Tyr Gly Ile Lys Thr
Arg Tyr Ser Tyr Phe Ser Glu Tyr Leu Pro Pro Ile Lys Thr Glu Lys
Leu Leu Asp Asn Thr Ile Tyr Thr Gln Asn Glu Gly Phe Asn Ile Ala
Ser Lys Asn Leu Lys Thr Glu Phe Asn Gly Gln Asn Lys Ala Val Asn
Lys Glu Ala Tyr Glu Glu Ile Ser Leu Glu His Leu Val Ile Tyr Arg
Ile Ala Met Cys Lys Pro Val Met Tyr Lys Asn Thr Gly Lys Ser Glu
Gln Cys Ile Ile Val Asn Asn Glu Asp Leu Phe Phe Ile Ala Asn Lys
Asp Ser Phe Ser Lys Asp Leu Ala Lys Ala Glu Thr Ile Ala Tyr Asn
Thr Gln Asn Asn Thr Ile Glu Asn Asn Phe Ser Ile Asp Gln Leu Ile
Leu Asp Asn Asp Leu Ser Ser Gly Ile Asp Leu Pro Asn Glu Asn Thr
Glu Pro Phe Thr Asn Phe Asp Asp Ile Asp Ile Pro Val Tyr Ile Lys
Gln Ser Ala Leu Lys Lys Ile Phe Val Asp Gly Asp Ser Leu Phe Glu
Tyr Leu His Ala Gln Thr Phe Pro Ser Asn Ile Glu Asn Leu Gln Leu
Thr Asn Ser Leu Asn Asp Ala Leu Arg Asn Asn Asn Lys Val Tyr Thr
Phe Phe Ser Thr Asn Leu Val Glu Lys Ala Asn Thr Val Val Gly Ala
Ser Leu Phe Val Asn Trp Val Lys Gly Val Ile Asp Asp Phe Thr Ser
Glu Ser Thr Gln Lys Ser Thr Ile Asp Lys Val Ser Asp Val Ser Ile
Ile Ile Pro Tyr Ile Gly Pro Ala Leu Asn Val Gly Asn Glu Thr Ala
Lys Glu Asn Phe Lys Asn Ala Phe Glu Ile Gly Gly Ala Ala Ile Leu
Met Glu Phe Ile Pro Glu Leu Ile Val Pro Ile Val Gly Phe Phe Thr
Leu Glu Ser Tyr Val Gly Asn Lys Gly His Ile Ile Met Thr Ile Ser
Asn Ala Leu Lys Lys Arg Asp Gln Lys Trp Thr Asp Met Tyr Gly Leu
Ile Val Ser Gln Trp Leu Ser Thr Val Asn Thr Gln Phe Tyr Thr Ile
```

```
Lys Glu Arg Met Tyr Asn Ala Leu Asn Asn Gln Ser Gln Ala Ile Glu
Lys Ile Ile Glu Asp Gln Tyr Asn Arg Tyr Ser Glu Glu Asp Lys Met
Asn Ile Asn Ile Asp Phe Asn Asp Ile Asp Phe Lys Leu Asn Gln Ser
Ile Asn Leu Ala Ile Asn Asn Ile Asp Asp Phe Ile Asn Gln Cys Ser
Ile Ser Tyr Leu Met Asn Arg Met Ile Pro Leu Ala Val Lys Lys Leu
Lys Asp Phe Asp Asp Asn Leu Lys Arg Asp Leu Leu Glu Tyr Ile Asp
Thr Asn Glu Leu Tyr Leu Leu Asp Glu Val Asn Ile Leu Lys Ser Lys
Val Asn Arg His Leu Lys Asp Ser Ile Pro Phe Asp Leu Ser Leu Tyr
Thr Lys Asp Thr Ile Leu Ile Gln Val Phe Asn Asn Tyr Ile Ser Asn
Ile Ser Ser Asn Ala Ile Leu Ser Leu Ser Tyr Arg Gly Gly Arg Leu
Ile Asp Ser Ser Gly Tyr Gly Ala Thr Met Asn Val Gly Ser Asp Val
Ile Phe Asn Asp Ile Gly Asn Gly Gln Phe Lys Leu Asn Asn Ser Glu
Asn Ser Asn Ile Thr Ala His Gln Ser Lys Phe Val Val Tyr Asp Ser
Met Phe Asp Asn Phe Ser Ile Asn Phe Trp Val Arg Thr Pro Lys Tyr
Asn Asn Asn Asp Ile Gln Thr Tyr Leu Gln Asn Glu Tyr Thr Ile Ile
Ser Cys Ile Lys Asn Asp Ser Gly Trp Lys Val Ser Ile Lys Gly Asn
Arg Ile Ile Trp Thr Leu Ile Asp Val Asn Ala Lys Ser Lys Ser Ile
Phe Phe Glu Tyr Ser Ile Lys Asp Asn Ile Ser Asp Tyr Ile Asn Lys
Trp Phe Ser Ile Thr Ile Thr Asn Asp Arg Leu Gly Asn Ala Asn Ile
Tyr Ile Asn Gly Ser Leu Lys Lys Ser Glu Lys Ile Leu Asn Leu Asp
Arg Ile Asn Ser Ser Asn Asp Ile Asp Phe Lys Leu Ile Asn Cys Thr
Asp Thr Thr Lys Phe Val Trp Ile Lys Asp Phe Asn Ile Phe Gly Arg
Glu Leu Asn Ala Thr Glu Val Ser Ser Leu Tyr Trp Ile Gln Ser Ser
Thr Asn Thr Leu Lys Asp Phe Trp Gly Asn Pro Leu Arg Tyr Asp Thr
Gln Tyr Tyr Leu Phe Asn Gln Gly Met Gln Asn Ile Tyr Ile Lys Tyr
Phe Ser Lys Ala Ser Met Gly Glu Thr Ala Pro Arg Thr Asn Phe Asn
Asn Ala Ala Ile Asn Tyr Gln Asn Leu Tyr Leu Gly Leu Arg Phe Ile
Ile Lys Lys Ala Ser Asn Ser Arg Asn Ile Asn Asn Asp Asn Ile Val
Arg Glu Gly Asp Tyr Ile Tyr Leu Asn Ile Asp Asn Ile Ser Asp Glu
Ser Tyr Arg Val Tyr Val Leu Val Asn Ser Lys Glu Ile Gln Thr Gln
Leu Phe Leu Ala Pro Ile Asn Asp Asp Pro Thr Phe Tyr Asp Val Leu
Gln Ile Lys Lys Tyr Tyr Glu Lys Thr Thr Tyr Asn Cys Gln Ile Leu
Cys Glu Lys Asp Thr Lys Thr Phe Gly Leu Phe Gly Ile Gly Lys Phe
Val Lys Asp Tyr Gly Tyr Val Trp Asp Thr Tyr Asp Asn Tyr Phe Cys
Ile Ser Gln Trp Tyr Leu Arg Arg Ile Ser Glu Asn Ile Asn Lys Leu
Arg Leu Gly Cys Asn Trp Gln Phe Ile Pro Val Asp Glu Gly Trp Thr
Glu
```

FIG. 20 (cont.)

*Clostridium botulinum* Serotype B, Strain Eklund 17B   (BoNT/B4)

MPVTINNFNYNDPIDNDNIIMMEPPFARGTGRYYKAFKITDRIW
IIPERYTFGYKPEDFNKSSGIFNRDVCEYYDPDYLNTNDKKNIFLQTMIKLFNRIKSK
PLGEKLLEMIINGIPYLGDRRVPLEEFNTNIASVTVNKLISNPGEVEQKKGIFANLII
FGPGPVLNENETIDIGIQNHFASREGFGGIMQMKFCPEYVSVFNNVQENKGASIFNRR
GYFSDPALILMHELIHVLHGLYGIKVDDLPIVPNEKKFFMQSTDTIQAEELYTFGGQD
PSIISPSTDKSIYDKVLQNFRGIVDRLNKVLVCISDPNININIYKNKFKDKYKFVEDS
EGKYSIDVESFNKLYKSLMFGFTEINIAENYKIKTRASYFSDSLPPVKIKNLLDNEIY
TIEEGFNISDKNMGKEYRGQNKAINKQAYEEISKEHLAVYKIQMCKSVKVPGICIDVD
NENLFFIADKNSFSDDLSKNERVEYNTQNNYIGNDFPINELILDTDLISKIELPSENT
ESLTDFNVDVPVYEKQPAIKKVFTDENTIFQYLYSQTFPLNIRDISLTSSFDDALLVS
SKVYSFFSMDYIKTANKVVEAGLFAGWVKQIVDDFVIEANKSSTMDKIADISLIVPYI
GLALNVGDETAKGNFESAFEIAGSSILLEFIPELLIPVVGVFLLESYIDNKNKIIKTI
DNALTKRVEKWIDMYGLIVAQWLSTVNTQFYTIKEGMYKALNYQAQALEEIIKYKYNI
YSEEEKSNININFNDINSKLNDGINQAMDNINDFINECSVSYLMKKMIPLAVKKLLDF
DNTLKKNLLNYIDENKLYLIGSVEDEKSKVDKYLKTIIPFDLSTYTNNEILIKIFNKY
NSEILNNIILNLRYRDNNLIDLSGYGAKVEVYDGVKLNDKNQFKLTSSADSKIRVTQN
QNIIFNSMFLDFSVSFWIRIPKYRNDDIQNYIHNEYTIINCMKNNSGWKISIRGNRII
WTLIDINGKTKSVFFEYNIREDISEYINRWFFVTITNNLDNAKIYINGTLESNMDIKD
IGEVIVNGEITFKLDGDVDRTQFIWMKYFSIFNTQLNQSNIKEIYKIQSYSEYLKDFW
GNPLMYNKEYYMFNAGNKNSYIKLVKDSSVGEILIRSKYNQNSNYINYRNLYIGEKFI
IRRKSNSQSINDDIVRKEDYIHLDFVNSNEEWRVYAYKNFKEQEQKLFLSIIYDSNEF
YKTIQIKEYDEQPTYSCQLLFKKDEESTDDIGLIGIHRFYESGVLRKKYKDYFCISKW
YLKEVKRKPYKSNLGCNWQFIPKDEGWTE

*FIG. 21*

SEQUENCE LISTING

```
<160> NUMBER OF SEQ ID NOS: 14

<210> SEQ ID NO 1
<211> LENGTH: 22
<212> TYPE: PRT
<213> ORGANISM: Mus sp.

<400> SEQUENCE: 1

Gly Glu Ser Gln Glu Asp Met Phe Ala Lys Leu Lys Glu Lys Phe Phe
1               5                   10                  15

Asn Glu Ile Asn Lys Ile
            20

<210> SEQ ID NO 2
<211> LENGTH: 435
<212> TYPE: PRT
<213> ORGANISM: Clostridium botulinum

<400> SEQUENCE: 2

Asn Ser Glu Ile Leu Asn Asn Ile Ile Leu Asn Leu Arg Tyr Lys Asp
1               5                   10                  15
```

-continued

```
Asn Asn Leu Ile Asp Leu Ser Gly Tyr Gly Ala Lys Val Glu Val Tyr
            20                  25                  30

Asp Gly Val Glu Leu Asn Asp Lys Asn Gln Phe Lys Leu Thr Ser Ser
            35                  40                  45

Ala Asn Ser Lys Ile Arg Val Thr Gln Asn Gln Asn Ile Ile Phe Asn
        50                  55                  60

Ser Val Phe Leu Asp Phe Ser Val Ser Phe Trp Ile Arg Ile Pro Lys
65                  70                  75                  80

Tyr Lys Asn Asp Gly Ile Gln Asn Tyr Ile His Asn Glu Tyr Thr Ile
                85                  90                  95

Ile Asn Cys Met Lys Asn Asn Ser Gly Trp Lys Ile Ser Ile Arg Gly
            100                 105                 110

Asn Arg Ile Ile Trp Thr Leu Ile Asp Ile Asn Gly Lys Thr Lys Ser
            115                 120                 125

Val Phe Phe Glu Tyr Asn Ile Arg Glu Asp Ile Ser Glu Tyr Ile Asn
        130                 135                 140

Arg Trp Phe Phe Val Thr Ile Thr Asn Asn Leu Asn Asn Ala Lys Ile
145                 150                 155                 160

Tyr Ile Asn Gly Lys Leu Glu Ser Asn Thr Asp Ile Lys Asp Ile Arg
                165                 170                 175

Glu Val Ile Ala Asn Gly Glu Ile Ile Phe Lys Leu Asp Gly Asp Ile
            180                 185                 190

Asp Arg Thr Gln Phe Ile Trp Met Lys Tyr Phe Ser Ile Phe Asn Thr
            195                 200                 205

Glu Leu Ser Gln Ser Asn Ile Glu Glu Arg Tyr Lys Ile Gln Ser Tyr
        210                 215                 220

Ser Glu Tyr Leu Lys Asp Phe Trp Gly Asn Pro Leu Met Tyr Asn Lys
225                 230                 235                 240

Glu Tyr Tyr Met Phe Asn Ala Gly Asn Lys Asn Ser Tyr Ile Lys Leu
                245                 250                 255

Lys Lys Asp Ser Pro Val Gly Glu Ile Leu Thr Arg Ser Lys Tyr Asn
            260                 265                 270

Gln Asn Ser Lys Tyr Ile Asn Tyr Arg Asp Leu Tyr Ile Gly Glu Lys
            275                 280                 285

Phe Ile Ile Arg Arg Lys Ser Asn Ser Gln Ser Ile Asn Asp Asp Ile
        290                 295                 300

Val Arg Lys Glu Asp Tyr Ile Tyr Leu Asp Phe Phe Asn Leu Asn Gln
305                 310                 315                 320

Glu Trp Arg Val Tyr Thr Tyr Lys Tyr Phe Lys Lys Glu Glu Glu Lys
                325                 330                 335

Leu Phe Leu Ala Pro Ile Ser Asp Ser Asp Glu Phe Tyr Asn Thr Ile
            340                 345                 350

Gln Ile Lys Glu Tyr Asp Glu Gln Pro Thr Tyr Ser Cys Gln Leu Leu
            355                 360                 365

Phe Lys Lys Asp Glu Glu Ser Thr Asp Glu Ile Gly Leu Ile Gly Ile
        370                 375                 380

His Arg Phe Tyr Glu Ser Gly Ile Val Phe Glu Glu Tyr Lys Asp Tyr
385                 390                 395                 400

Phe Cys Ile Ser Lys Trp Tyr Leu Lys Glu Val Lys Arg Lys Pro Tyr
                405                 410                 415

Asn Leu Lys Leu Gly Cys Asn Trp Gln Phe Ile Pro Lys Asp Glu Gly
            420                 425                 430

Trp Thr Glu
```

-continued

```
          435

<210> SEQ ID NO 3
<211> LENGTH: 1308
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
aacagcgaaa tcctgaacaa cattattctg aacctgcgct ataaagataa caacctgatt       60
gatctgagcg gctatggcgc gaaagtggaa gtgtatgatg gcgtggaact gaacgataaa      120
aaccagttca aactgaccag ctctgcgaac agcaaaattc gtgtgaccca gaaccagaac      180
attatcttca acagcgtgtt tctggatttt agcgtgagct tttggattcg catcccgaaa      240
tataaaaacg atggcatcca gaactatatc cacaacgaat acaccattat caactgcatg      300
aaaaacaaca gcggctggaa aattagcatt cgtggcaacc gtattatttg gaccctgatc      360
gatattaacg gcaaaaccaa aagcgtgttc ttcgaataca catccgcga agatatcagc      420 gaatacatta accgctggtt ctttgtgacc attaccaaca acctgaacaa cgcgaaaatt      480
tatatcaacg gtaaactgga aagcaacacc gatatcaaag atatccgcga agtgattgcg      540
aacggcgaaa tcatctttaa actggatggc gatattgatc gtacccagtt catctggatg      600
aaatacttca gcatcttcaa caccgaactg agccagagca cattgaaga acgctacaaa      660 atccagagct atagcgaata cctgaaagat ttttggggca atccgctgat gtataacaaa      720
gagtattaca tgttcaacgc gggtaacaaa aacagctata tcaaactgaa aaaagatagc      780
ccggtgggcg aaattctgac ccgtagcaaa tataaccaga acagcaaata catcaactat      840
cgcgatctgt atatcggcga aaaatttatc attcgccgca aaagcaacag ccagagcatt      900
aacgatgata tcgtgcgcaa agaagattat atctacctgg attttttcaa cctgaaccag      960
gaatggcgcg tttatacctat aaatatttc aaaaaagagg aagagaaact gtttctggcc     1020
ccgattagcg atagcgatga attttacaac accatccaaa ttaaagaata cgatgaacag     1080
ccgacctata gctgccagct gctgtttaaa aaagatgaag aaagcaccga tgaaattggc     1140
ctgattggca tccatcgttt ctatgaaagc ggcatcgtgt tcgaagaata taagattatt     1200
ttctgcatca gcaaatggta tctgaaagaa gtgaaacgca aaccgtataa cctgaaactg     1260
ggctgcaact ggcagtttat tccgaaagat gaaggctgga ccgaataa              1308

<210> SEQ ID NO 4
<211> LENGTH: 1296
<212> TYPE: PRT
<213> ORGANISM: Clostridium botulinum

<400> SEQUENCE: 4

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
```

-continued

```
                    65                          70                          75                          80

Asp Asn Glu Lys Asp Asn Tyr Leu Lys Gly Val Thr Lys Leu Phe Glu
                    85                          90                          95

Arg Ile Tyr Ser Thr Asp Leu Gly Arg Met Leu Leu Thr Ser Ile Val
                    100                         105                         110

Arg Gly Ile Pro Phe Trp Gly Gly Ser Thr Ile Asp Thr Glu Leu Lys
                    115                         120                         125

Val Ile Asp Thr Asn Cys Ile Asn Val Ile Gln Pro Asp Gly Ser Tyr
        130                         135                         140

Arg Ser Glu Glu Leu Asn Leu Val Ile Ile Gly Pro Ser Ala Asp Ile
145                         150                         155                         160

Ile Gln Phe Glu Cys Lys Ser Phe Gly His Glu Val Leu Asn Leu Thr
                    165                         170                         175

Arg Asn Gly Tyr Gly Ser Thr Gln Tyr Ile Arg Phe Ser Pro Asp Phe
                    180                         185                         190

Thr Phe Gly Phe Glu Glu Ser Leu Glu Val Asp Thr Asn Pro Leu Leu
                    195                         200                         205

Gly Ala Gly Lys Phe Ala Thr Asp Pro Ala Val Thr Leu Ala His Glu
        210                         215                         220

Leu Ile His Ala Gly His Arg Leu Tyr Gly Ile Ala Ile Asn Pro Asn
225                         230                         235                         240

Arg Val Phe Lys Val Asn Thr Asn Ala Tyr Tyr Glu Met Ser Gly Leu
                    245                         250                         255

Glu Val Ser Phe Glu Glu Leu Arg Thr Phe Gly Gly His Asp Ala Lys
                    260                         265                         270

Phe Ile Asp Ser Leu Gln Glu Asn Glu Phe Arg Leu Tyr Tyr Tyr Asn
                    275                         280                         285

Lys Phe Lys Asp Ile Ala Ser Thr Leu Asn Lys Ala Lys Ser Ile Val
        290                         295                         300

Gly Thr Thr Ala Ser Leu Gln Tyr Met Lys Asn Val Phe Lys Glu Lys
305                         310                         315                         320

Tyr Leu Leu Ser Glu Asp Thr Ser Gly Lys Phe Ser Val Asp Lys Leu
                    325                         330                         335

Lys Phe Asp Lys Leu Tyr Lys Met Leu Thr Glu Ile Tyr Thr Glu Asp
        340                         345                         350

Asn Phe Val Lys Phe Phe Lys Val Leu Asn Arg Lys Thr Tyr Leu Asn
        355                         360                         365

Phe Asp Lys Ala Val Phe Lys Ile Asn Ile Val Pro Lys Val Asn Tyr
        370                         375                         380

Thr Ile Tyr Asp Gly Phe Asn Leu Arg Asn Thr Asn Leu Ala Ala Asn
385                         390                         395                         400

Phe Asn Gly Gln Asn Thr Glu Ile Asn Asn Met Asn Phe Thr Lys Leu
                    405                         410                         415

Lys Asn Phe Thr Gly Leu Phe Glu Phe Tyr Lys Leu Leu Cys Val Arg
                    420                         425                         430

Gly Ile Ile Thr Ser Lys Thr Lys Ser Leu Asp Lys Gly Tyr Asn Lys
        435                         440                         445

Ala Leu Asn Asp Leu Cys Ile Lys Val Asn Asn Trp Asp Leu Phe Phe
        450                         455                         460

Ser Pro Ser Glu Asp Asn Phe Thr Asn Asp Leu Asn Lys Gly Glu Glu
465                         470                         475                         480

Ile Thr Ser Asp Thr Asn Ile Glu Ala Ala Glu Glu Asn Ile Ser Leu
                    485                         490                         495
```

-continued

```
Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
            770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910
```

-continued

```
Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295
```

-continued

```
<210> SEQ ID NO 5
<211> LENGTH: 1291
<212> TYPE: PRT
<213> ORGANISM: Clostridium botulinum

<400> SEQUENCE: 5

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380
```

-continued

```
Asn Leu Leu Asp Asn Glu Ile Tyr Thr Ile Glu Glu Gly Phe Asn Ile
385             390             395             400

Ser Asp Lys Asp Met Glu Lys Glu Tyr Arg Gly Gln Asn Lys Ala Ile
            405             410             415

Asn Lys Gln Ala Tyr Glu Glu Ile Ser Lys Glu His Leu Ala Val Tyr
            420             425             430

Lys Ile Gln Met Cys Lys Ser Val Lys Ala Pro Gly Ile Cys Ile Asp
            435             440             445

Val Asp Asn Glu Asp Leu Phe Phe Ile Ala Asp Lys Asn Ser Phe Ser
    450             455             460

Asp Asp Leu Ser Lys Asn Glu Arg Ile Glu Tyr Asn Thr Gln Ser Asn
465             470             475             480

Tyr Ile Glu Asn Asp Phe Pro Ile Asn Glu Leu Ile Leu Asp Thr Asp
            485             490             495

Leu Ile Ser Lys Ile Glu Leu Pro Ser Glu Asn Thr Glu Ser Leu Thr
            500             505             510

Asp Phe Asn Val Asp Val Pro Val Tyr Glu Lys Gln Pro Ala Ile Lys
            515             520             525

Lys Ile Phe Thr Asp Glu Asn Thr Ile Phe Gln Tyr Leu Tyr Ser Gln
    530             535             540

Thr Phe Pro Leu Asp Ile Arg Asp Ile Ser Leu Thr Ser Ser Phe Asp
545             550             555             560

Asp Ala Leu Leu Phe Ser Asn Lys Val Tyr Ser Phe Phe Ser Met Asp
            565             570             575

Tyr Ile Lys Thr Ala Asn Lys Val Val Glu Ala Gly Leu Phe Ala Gly
            580             585             590

Trp Val Lys Gln Ile Val Asn Asp Phe Val Ile Glu Ala Asn Lys Ser
            595             600             605

Asn Thr Met Asp Lys Ile Ala Asp Ile Ser Leu Ile Val Pro Tyr Ile
            610             615             620

Gly Leu Ala Leu Asn Val Gly Asn Glu Thr Ala Lys Gly Asn Phe Glu
625             630             635             640

Asn Ala Phe Glu Ile Ala Gly Ala Ser Ile Leu Leu Glu Phe Ile Pro
            645             650             655

Glu Leu Leu Ile Pro Val Val Gly Ala Phe Leu Leu Glu Ser Tyr Ile
            660             665             670

Asp Asn Lys Asn Lys Ile Ile Lys Thr Ile Asp Asn Ala Leu Thr Lys
            675             680             685

Arg Asn Glu Lys Trp Ser Asp Met Tyr Gly Leu Ile Val Ala Gln Trp
    690             695             700

Leu Ser Thr Val Asn Thr Gln Phe Tyr Thr Ile Lys Glu Gly Met Tyr
705             710             715             720

Lys Ala Leu Asn Tyr Gln Ala Gln Ala Leu Glu Glu Ile Ile Lys Tyr
            725             730             735

Arg Tyr Asn Ile Tyr Ser Glu Lys Glu Lys Ser Asn Ile Asn Ile Asp
            740             745             750

Phe Asn Asp Ile Asn Ser Lys Leu Asn Glu Gly Ile Asn Gln Ala Ile
            755             760             765

Asp Asn Ile Asn Asn Phe Ile Asn Gly Cys Ser Val Ser Tyr Leu Met
            770             775             780

Lys Lys Met Ile Pro Leu Ala Val Glu Lys Leu Leu Asp Phe Asp Asn
785             790             795             800

Thr Leu Lys Lys Asn Leu Leu Asn Tyr Ile Asp Glu Asn Lys Leu Tyr
```

-continued

```
                     805              810              815
Leu Ile Gly Ser Ala Glu Tyr Glu Lys Ser Lys Val Asn Lys Tyr Leu
             820              825              830

Lys Thr Ile Met Pro Phe Asp Leu Ser Ile Tyr Thr Asn Asp Thr Ile
             835              840              845

Leu Ile Glu Met Phe Asn Lys Tyr Asn Ser Glu Ile Leu Asn Asn Ile
         850              855              860

Ile Leu Asn Leu Arg Tyr Lys Asp Asn Asn Leu Ile Asp Leu Ser Gly
865              870              875              880

Tyr Gly Ala Lys Val Glu Val Tyr Asp Gly Val Glu Leu Asn Asp Lys
                 885              890              895

Asn Gln Phe Lys Leu Thr Ser Ser Ala Asn Ser Lys Ile Arg Val Thr
             900              905              910

Gln Asn Gln Asn Ile Ile Phe Asn Ser Val Phe Leu Asp Phe Ser Val
             915              920              925

Ser Phe Trp Ile Arg Ile Pro Lys Tyr Lys Asn Asp Gly Ile Gln Asn
         930              935              940

Tyr Ile His Asn Glu Tyr Thr Ile Ile Asn Cys Met Lys Asn Asn Ser
945              950              955              960

Gly Trp Lys Ile Ser Ile Arg Gly Asn Arg Ile Ile Trp Thr Leu Ile
                 965              970              975

Asp Ile Asn Gly Lys Thr Lys Ser Val Phe Phe Glu Tyr Asn Ile Arg
             980              985              990

Glu Asp Ile Ser Glu Tyr Ile Asn  Arg Trp Phe Phe Val  Thr Ile Thr
             995              1000              1005

Asn Asn  Leu Asn Asn Ala Lys  Ile Tyr Ile Asn Gly  Lys Leu Glu
    1010              1015              1020

Ser Asn  Thr Asp Ile Lys Asp  Ile Arg Glu Val Ile  Ala Asn Gly
    1025              1030              1035

Glu Ile  Ile Phe Lys Leu Asp  Gly Asp Ile Asp Arg  Thr Gln Phe
    1040              1045              1050

Ile Trp  Met Lys Tyr Phe Ser  Ile Phe Asn Thr Glu  Leu Ser Gln
    1055              1060              1065

Ser Asn  Ile Glu Glu Arg Tyr  Lys Ile Gln Ser Tyr  Ser Glu Tyr
    1070              1075              1080

Leu Lys  Asp Phe Trp Gly Asn  Pro Leu Met Tyr Asn  Lys Glu Tyr
    1085              1090              1095

Tyr Met  Phe Asn Ala Gly Asn  Lys Asn Ser Tyr Ile  Lys Leu Lys
    1100              1105              1110

Lys Asp  Ser Pro Val Gly Glu  Ile Leu Thr Arg Ser  Lys Tyr Asn
    1115              1120              1125

Gln Asn  Ser Lys Tyr Ile Asn  Tyr Arg Asp Leu Tyr  Ile Gly Glu
    1130              1135              1140

Lys Phe  Ile Ile Arg Arg Lys  Ser Asn Ser Gln Ser  Ile Asn Asp
    1145              1150              1155

Asp Ile  Val Arg Lys Glu Asp  Tyr Ile Tyr Leu Asp  Phe Phe Asn
    1160              1165              1170

Leu Asn  Gln Glu Trp Arg Val  Tyr Thr Tyr Lys Tyr  Phe Lys Lys
    1175              1180              1185

Glu Glu  Glu Lys Leu Phe Leu  Ala Pro Ile Ser Asp  Ser Asp Glu
    1190              1195              1200

Phe Tyr  Asn Thr Ile Gln Ile  Lys Glu Tyr Asp Glu  Gln Pro Thr
    1205              1210              1215
```

-continued

```
Tyr Ser  Cys Gln Leu Leu Phe  Lys Lys Asp Glu Glu  Ser Thr Asp
    1220             1225             1230

Glu Ile  Gly Leu Ile Gly Ile  His Arg Phe Tyr Glu  Ser Gly Ile
    1235             1240             1245

Val Phe  Glu Glu Tyr Lys Asp  Tyr Phe Cys Ile Ser  Lys Trp Tyr
    1250             1255             1260

Leu Lys  Glu Val Lys Arg Lys  Pro Tyr Asn Leu Lys  Leu Gly Cys
    1265             1270             1275

Asn Trp  Gln Phe Ile Pro Lys  Asp Glu Gly Trp Thr  Glu
    1280             1285             1290

<210> SEQ ID NO 6
<211> LENGTH: 1291
<212> TYPE: PRT
<213> ORGANISM: Clostridium botulinum

<400> SEQUENCE: 6

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
            195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
```

-continued

```
        290                 295                 300
Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
                355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
                435                 440                 445

Lys Thr Leu Asp Cys Arg Glu Leu Leu Val Lys Asn Thr Asp Leu Pro
        450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
                515                 520                 525

Glu Asn Gln Val Phe Tyr Asp Asn Arg Thr Gln Asn Val Asp Tyr Leu
        530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
                580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
        610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
                675                 680                 685

Thr Ile Asp Asn Cys Leu Glu Gln Arg Ile Lys Arg Trp Lys Asp Ser
        690                 695                 700

Tyr Glu Trp Met Met Gly Thr Trp Leu Ser Arg Ile Ile Thr Gln Phe
705                 710                 715                 720
```

-continued

```
Asn Asn Ile Ser Tyr Gln Met Tyr Asp Ser Leu Asn Tyr Gln Ala Gly
            725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
                900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn  Ala Pro Gly Tyr Asn  Lys Trp Phe
    995                 1000                1005

Phe Val  Thr Val Thr Asn Asn  Met Met Gly Asn Met  Lys Ile Tyr
    1010                1015                1020

Ile Asn  Gly Lys Leu Ile Asp  Thr Ile Lys Val Lys  Glu Leu Thr
    1025                1030                1035

Gly Ile  Asn Phe Ser Lys Thr  Ile Thr Phe Glu Ile  Asn Lys Ile
    1040                1045                1050

Pro Asp  Thr Gly Leu Ile Thr  Ser Asp Ser Asp Asn  Ile Asn Met
    1055                1060                1065

Trp Ile  Arg Asp Phe Tyr Ile  Phe Ala Lys Glu Leu  Asp Gly Lys
    1070                1075                1080

Asp Ile  Asn Ile Leu Phe Asn  Ser Leu Gln Tyr Thr  Asn Val Val
    1085                1090                1095

Lys Asp  Tyr Trp Gly Asn Asp  Leu Arg Tyr Asn Lys  Glu Tyr Tyr
    1100                1105                1110

Met Val  Asn Ile Asp Tyr Leu  Asn Arg Tyr Met Tyr  Ala Asn Ser
    1115                1120                1125
```

-continued

```
Arg Gln  Ile Val Phe Asn Thr  Arg Arg Asn Asn Asn  Asp Phe Asn
    1130             1135             1140

Glu Gly  Tyr Lys Ile Ile Ile  Lys Arg Ile Arg Gly  Asn Thr Asn
    1145             1150             1155

Asp Thr  Arg Val Arg Gly Gly  Asp Ile Leu Tyr Phe  Asp Met Thr
    1160             1165             1170

Ile Asn  Asn Lys Ala Tyr Asn  Leu Phe Met Lys Asn  Glu Thr Met
    1175             1180             1185

Tyr Ala  Asp Asn His Ser Thr  Glu Asp Ile Tyr Ala  Ile Gly Leu
    1190             1195             1200

Arg Glu  Gln Thr Lys Asp Ile  Asn Asp Asn Ile Ile  Phe Gln Ile
    1205             1210             1215

Gln Pro  Met Asn Asn Thr Tyr  Tyr Tyr Ala Ser Gln  Ile Phe Lys
    1220             1225             1230

Ser Asn  Phe Asn Gly Glu Asn  Ile Ser Gly Ile Cys  Ser Ile Gly
    1235             1240             1245

Thr Tyr  Arg Phe Arg Leu Gly  Gly Asp Trp Tyr Arg  His Asn Tyr
    1250             1255             1260

Leu Val  Pro Thr Val Lys Gln  Gly Asn Tyr Ala Ser  Leu Leu Glu
    1265             1270             1275

Ser Thr  Ser Thr His Trp Gly  Phe Val Pro Val Ser  Glu
    1280             1285             1290

<210> SEQ ID NO 7
<211> LENGTH: 1276
<212> TYPE: PRT
<213> ORGANISM: Clostridium botulinum

<400> SEQUENCE: 7

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
            115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
            195                 200                 205
```

-continued

```
Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
                260                 265                 270

Phe Gly Gly Leu Asp Val Glu Ile Ile Pro Gln Ile Glu Arg Ser Gln
                275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
                340                 345                 350

Asp Leu Thr Asn Val Met Ser Glu Val Val Tyr Ser Ser Gln Tyr Asn
    355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
                420                 425                 430

Phe Thr Lys Val Cys Leu Arg Leu Thr Lys Asn Ser Arg Asp Asp Ser
                435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
                500                 505                 510

Pro Asn Val Asn Met Glu Pro Leu Asn Leu Pro Gly Glu Glu Ile Val
    515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
    595                 600                 605

Ile Met Lys Lys Asp Thr Leu Asp Lys Ile Ser Asp Val Ser Val Ile
    610                 615                 620
```

```
Ile Pro Tyr Ile Gly Pro Ala Leu Asn Ile Gly Asn Ser Ala Leu Arg
625             630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
                675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
                755                 760                 765

Ser Glu Ala Met Asn Asn Ile Asn Lys Phe Ile Arg Glu Cys Ser Val
        770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
                820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
        850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
                900                 905                 910

Lys Ile Ile Val Asn Leu Asn Asn Asn Ile Leu Tyr Ser Ala Ile Tyr
                915                 920                 925

Glu Asn Ser Ser Val Ser Phe Trp Ile Lys Ile Ser Lys Asp Leu Thr
        930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
                980                 985                 990

Leu Ser His Thr Gly Tyr Thr Asn  Lys Trp Phe Phe Val  Thr Ile Thr
                995                 1000                1005

Asn Asn  Ile Met Gly Tyr Met  Lys Leu Tyr Ile Asn  Gly Glu Leu
        1010                1015                1020

Lys Gln  Ser Gln Lys Ile Glu  Asp Leu Asp Glu Val  Lys Leu Asp
        1025                1030                1035

Lys Thr  Ile Val Phe Gly Ile  Asp Glu Asn Ile Asp  Glu Asn Gln
```

```
        1040                1045                1050

Met Leu Trp Ile Arg Asp Phe  Asn Ile Phe Ser Lys  Glu Leu Ser
    1055                1060                1065

Asn Glu  Asp Ile Asn Ile Val  Tyr Glu Gly Gln Ile  Leu Arg Asn
    1070                1075                1080

Val Ile  Lys Asp Tyr Trp Gly  Asn Pro Leu Lys Phe  Asp Thr Glu
    1085                1090                1095

Tyr Tyr  Ile Ile Asn Asp Asn  Tyr Ile Asp Arg Tyr  Ile Ala Pro
    1100                1105                1110

Glu Ser  Asn Val Leu Val Leu  Val Gln Tyr Pro Asp  Arg Ser Lys
    1115                1120                1125

Leu Tyr  Thr Gly Asn Pro Ile  Thr Ile Lys Ser Val  Ser Asp Lys
    1130                1135                1140

Asn Pro  Tyr Ser Arg Ile Leu  Asn Gly Asp Asn Ile  Ile Leu His
    1145                1150                1155

Met Leu  Tyr Asn Ser Arg Lys  Tyr Met Ile Ile Arg  Asp Thr Asp
    1160                1165                1170

Thr Ile  Tyr Ala Thr Gln Gly  Gly Glu Cys Ser Gln  Asn Cys Val
    1175                1180                1185

Tyr Ala  Leu Lys Leu Gln Ser  Asn Leu Gly Asn Tyr  Gly Ile Gly
    1190                1195                1200

Ile Phe  Ser Ile Lys Asn Ile  Val Ser Lys Asn Lys  Tyr Cys Ser
    1205                1210                1215

Gln Ile  Phe Ser Ser Phe Arg  Glu Asn Thr Met Leu  Leu Ala Asp
    1220                1225                1230

Ile Tyr  Lys Pro Trp Arg Phe  Ser Phe Lys Asn Ala  Tyr Thr Pro
    1235                1240                1245

Val Ala  Val Thr Asn Tyr Glu  Thr Lys Leu Leu Ser  Thr Ser Ser
    1250                1255                1260

Phe Trp  Lys Phe Ile Ser Arg  Asp Pro Gly Trp Val  Glu
    1265                1270                1275

<210> SEQ ID NO 8
<211> LENGTH: 1252
<212> TYPE: PRT
<213> ORGANISM: Clostridium botulinum

<400> SEQUENCE: 8

Met Pro Lys Ile Asn Ser Phe Asn Tyr Asn Asp Pro Val Asn Asp Arg
1                5                10                15

Thr Ile Leu Tyr Ile Lys Pro Gly Gly Cys Gln Glu Phe Tyr Lys Ser
        20                25                30

Phe Asn Ile Met Lys Asn Ile Trp Ile Ile Pro Glu Arg Asn Val Ile
        35                40                45

Gly Thr Thr Pro Gln Asp Phe His Pro Pro Thr Ser Leu Lys Asn Gly
        50                55                60

Asp Ser Ser Tyr Tyr Asp Pro Asn Tyr Leu Gln Ser Asp Glu Glu Lys
65                70                75                80

Asp Arg Phe Leu Lys Ile Val Thr Lys Ile Phe Asn Arg Ile Asn Asn
                85                90                95

Asn Leu Ser Gly Gly Ile Leu Leu Glu Glu Leu Ser Lys Ala Asn Pro
            100                105                110

Tyr Leu Gly Asn Asp Asn Thr Pro Asp Asn Gln Phe His Ile Gly Asp
        115                120                125
```

-continued

```
Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
                435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
                515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
```

-continued

```
545                   550                   555                   560

Asn Asn Val Asn Lys Pro Val Gln Ala Ala Leu Phe Val Ser Trp Ile
                  565                   570                   575

Gln Gln Val Leu Val Asp Phe Thr Thr Glu Ala Asn Gln Lys Ser Thr
                  580                   585                   590

Val Asp Lys Ile Ala Asp Ile Ser Ile Val Val Pro Tyr Ile Gly Leu
                  595                   600                   605

Ala Leu Asn Ile Gly Asn Glu Ala Gln Lys Gly Asn Phe Lys Asp Ala
            610                   615                   620

Leu Glu Leu Leu Gly Ala Gly Ile Leu Leu Glu Phe Glu Pro Glu Leu
625                   630                   635                   640

Leu Ile Pro Thr Ile Leu Val Phe Thr Ile Lys Ser Phe Leu Gly Ser
                  645                   650                   655

Ser Asp Asn Lys Asn Lys Val Ile Lys Ala Ile Asn Asn Ala Leu Lys
                  660                   665                   670

Glu Arg Asp Glu Lys Trp Lys Glu Val Tyr Ser Phe Ile Val Ser Asn
                  675                   680                   685

Trp Met Thr Lys Ile Asn Thr Gln Phe Asn Lys Arg Lys Glu Gln Met
            690                   695                   700

Tyr Gln Ala Leu Gln Asn Gln Val Asn Ala Ile Lys Thr Ile Ile Glu
705                   710                   715                   720

Ser Lys Tyr Asn Ser Tyr Thr Leu Glu Glu Lys Asn Glu Leu Thr Asn
                  725                   730                   735

Lys Tyr Asp Ile Lys Gln Ile Glu Asn Glu Leu Asn Gln Lys Val Ser
                  740                   745                   750

Ile Ala Met Asn Asn Ile Asp Arg Phe Leu Thr Glu Ser Ser Ile Ser
                  755                   760                   765

Tyr Leu Met Lys Leu Ile Asn Glu Val Lys Ile Asn Lys Leu Arg Glu
            770                   775                   780

Tyr Asp Glu Asn Val Lys Thr Tyr Leu Leu Asn Tyr Ile Ile Gln His
785                   790                   795                   800

Gly Ser Ile Leu Gly Glu Ser Gln Gln Glu Leu Asn Ser Met Val Thr
                  805                   810                   815

Asp Thr Leu Asn Asn Ser Ile Pro Phe Lys Leu Ser Ser Tyr Thr Asp
                  820                   825                   830

Asp Lys Ile Leu Ile Ser Tyr Phe Asn Lys Phe Phe Lys Arg Ile Lys
            835                   840                   845

Ser Ser Ser Val Leu Asn Met Arg Tyr Lys Asn Asp Lys Tyr Val Asp
850                   855                   860

Thr Ser Gly Tyr Asp Ser Asn Ile Asn Ile Asn Gly Asp Val Tyr Lys
865                   870                   875                   880

Tyr Pro Thr Asn Lys Asn Gln Phe Gly Ile Tyr Asn Asp Lys Leu Ser
                  885                   890                   895

Glu Val Asn Ile Ser Gln Asn Asp Tyr Ile Ile Tyr Asp Asn Lys Tyr
                  900                   905                   910

Lys Asn Phe Ser Ile Ser Phe Trp Val Arg Ile Pro Asn Tyr Asp Asn
                  915                   920                   925

Lys Ile Val Asn Val Asn Asn Glu Tyr Thr Ile Ile Asn Cys Met Arg
            930                   935                   940

Asp Asn Asn Ser Gly Trp Lys Val Ser Leu Asn His Asn Glu Ile Ile
945                   950                   955                   960

Trp Thr Leu Gln Asp Asn Ala Gly Ile Asn Gln Lys Leu Ala Phe Asn
                  965                   970                   975
```

-continued

```
Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn Leu Ile Asp Gln Lys  Ser Ile Leu Asn Leu  Gly Asn Ile
    1010                1015                1020

His Val Ser Asp Asn Ile Leu  Phe Lys Ile Val Asn  Cys Ser Tyr
    1025                1030                1035

Thr Arg Tyr Ile Gly Ile Arg  Tyr Phe Asn Ile Phe  Asp Lys Glu
    1040                1045                1050

Leu Asp Glu Thr Glu Ile Gln  Thr Leu Tyr Ser Asn  Glu Pro Asn
    1055                1060                1065

Thr Asn Ile Leu Lys Asp Phe  Trp Gly Asn Tyr Leu  Leu Tyr Asp
    1070                1075                1080

Lys Glu Tyr Tyr Leu Leu Asn  Val Leu Lys Pro Asn  Asn Phe Ile
    1085                1090                1095

Asp Arg Arg Lys Asp Ser Thr  Leu Ser Ile Asn Asn  Ile Arg Ser
    1100                1105                1110

Thr Ile Leu Leu Ala Asn Arg  Leu Tyr Ser Gly Ile  Lys Val Lys
    1115                1120                1125

Ile Gln Arg Val Asn Asn Ser  Ser Thr Asn Asp Asn  Leu Val Arg
    1130                1135                1140

Lys Asn Asp Gln Val Tyr Ile  Asn Phe Val Ala Ser  Lys Thr His
    1145                1150                1155

Leu Phe Pro Leu Tyr Ala Asp  Thr Ala Thr Thr Asn  Lys Glu Lys
    1160                1165                1170

Thr Ile Lys Ile Ser Ser Ser  Gly Asn Arg Phe Asn  Gln Val Val
    1175                1180                1185

Val Met Asn Ser Val Gly Asn  Asn Cys Thr Met Asn  Phe Lys Asn
    1190                1195                1200

Asn Asn Gly Asn Asn Ile Gly  Leu Leu Gly Phe Lys  Ala Asp Thr
    1205                1210                1215

Val Val Ala Ser Thr Trp Tyr  Tyr Thr His Met Arg  Asp His Thr
    1220                1225                1230

Asn Ser Asn Gly Cys Phe Trp  Asn Phe Ile Ser Glu  Glu His Gly
    1235                1240                1245

Trp Gln Glu Lys
    1250

<210> SEQ ID NO 9
<211> LENGTH: 1274
<212> TYPE: PRT
<213> ORGANISM: Clostridium botulinum

<400> SEQUENCE: 9

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
```

-continued

```
65                    70                    75                    80

Asp Ala Glu Lys Asp Arg Tyr Leu Lys Thr Thr Ile Lys Leu Phe Lys
                85                    90                    95

Arg Ile Asn Ser Asn Pro Ala Gly Lys Val Leu Leu Gln Glu Ile Ser
                100                   105                   110

Tyr Ala Lys Pro Tyr Leu Gly Asn Asp His Thr Pro Ile Asp Glu Phe
                115                   120                   125

Ser Pro Val Thr Arg Thr Thr Ser Val Asn Ile Lys Leu Ser Thr Asn
                130                   135                   140

Val Glu Ser Ser Met Leu Leu Asn Leu Leu Val Leu Gly Ala Gly Pro
145                   150                   155                   160

Asp Ile Phe Glu Ser Cys Cys Tyr Pro Val Arg Lys Leu Ile Asp Pro
                165                   170                   175

Asp Val Val Tyr Asp Pro Ser Asn Tyr Gly Phe Gly Ser Ile Asn Ile
                180                   185                   190

Val Thr Phe Ser Pro Glu Tyr Glu Tyr Thr Phe Asn Asp Ile Ser Gly
                195                   200                   205

Gly His Asn Ser Ser Thr Glu Ser Phe Ile Ala Asp Pro Ala Ile Ser
                210                   215                   220

Leu Ala His Glu Leu Ile His Ala Leu His Gly Leu Tyr Gly Ala Arg
225                   230                   235                   240

Gly Val Thr Tyr Glu Glu Thr Ile Glu Val Lys Gln Ala Pro Leu Met
                245                   250                   255

Ile Ala Glu Lys Pro Ile Arg Leu Glu Glu Phe Leu Thr Phe Gly Gly
                260                   265                   270

Gln Asp Leu Asn Ile Ile Thr Ser Ala Met Lys Glu Lys Ile Tyr Asn
                275                   280                   285

Asn Leu Leu Ala Asn Tyr Glu Lys Ile Ala Thr Arg Leu Ser Glu Val
                290                   295                   300

Asn Ser Ala Pro Pro Glu Tyr Asp Ile Asn Glu Tyr Lys Asp Tyr Phe
305                   310                   315                   320

Gln Trp Lys Tyr Gly Leu Asp Lys Asn Ala Asp Gly Ser Tyr Thr Val
                325                   330                   335

Asn Glu Asn Lys Phe Asn Glu Ile Tyr Lys Lys Leu Tyr Ser Phe Thr
                340                   345                   350

Glu Ser Asp Leu Ala Asn Lys Phe Lys Val Lys Cys Arg Asn Thr Tyr
                355                   360                   365

Phe Ile Lys Tyr Glu Phe Leu Lys Val Pro Asn Leu Leu Asp Asp Asp
                370                   375                   380

Ile Tyr Thr Val Ser Glu Gly Phe Asn Ile Gly Asn Leu Ala Val Asn
385                   390                   395                   400

Asn Arg Gly Gln Ser Ile Lys Leu Asn Pro Lys Ile Ile Asp Ser Ile
                405                   410                   415

Pro Asp Lys Gly Leu Val Glu Lys Ile Val Lys Phe Cys Lys Ser Val
                420                   425                   430

Ile Pro Arg Lys Gly Thr Lys Ala Pro Pro Arg Leu Cys Ile Arg Val
                435                   440                   445

Asn Asn Ser Glu Leu Phe Phe Val Ala Ser Glu Ser Ser Tyr Asn Glu
                450                   455                   460

Asn Asp Ile Asn Thr Pro Lys Glu Ile Asp Asp Thr Thr Asn Leu Asn
465                   470                   475                   480

Asn Asn Tyr Arg Asn Asn Leu Asp Glu Val Ile Leu Asp Tyr Asn Ser
                485                   490                   495
```

-continued

```
Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
                580                 585                 590

Trp Ile Ser Lys Val Ile Arg Asp Phe Thr Thr Glu Ala Thr Gln Lys
                595                 600                 605

Ser Thr Val Asp Lys Ile Ala Asp Ile Ser Leu Ile Val Pro Tyr Val
            610                 615                 620

Gly Leu Ala Leu Asn Ile Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
                660                 665                 670

Asp Ser Tyr Glu Asn Lys Asn Lys Ala Ile Lys Ala Ile Asn Asn Ser
            675                 680                 685

Leu Ile Glu Arg Glu Ala Lys Trp Lys Glu Ile Tyr Ser Trp Ile Val
            690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
                740                 745                 750

Glu Ser Glu Tyr Asn Ile Asn Asn Ile Glu Glu Glu Leu Asn Lys Lys
            755                 760                 765

Val Ser Leu Ala Met Lys Asn Ile Glu Arg Phe Met Thr Glu Ser Ser
            770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
            835                 840                 845

Thr Asn Asp Lys Ile Leu Ile Ile Tyr Phe Asn Arg Leu Tyr Lys Lys
            850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
            900                 905                 910
```

-continued

```
Leu Ser Glu Val Asn Ile Ala Gln Asn Asn Asp Ile Ile Tyr Asn Ser
        915                 920                 925

Arg Tyr Gln Asn Phe Ser Ile Ser Phe Trp Val Arg Ile Pro Lys His
        930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
        995                 1000                1005

Lys Trp Ile Phe Val Thr Ile Thr Asn Asn Arg Leu Gly Asn Ser
    1010                1015                1020

Arg Ile Tyr Ile Asn Gly Asn Leu Ile Val Glu Lys Ser Ile Ser
    1025                1030                1035

Asn Leu Gly Asp Ile His Val Ser Asp Asn Ile Leu Phe Lys Ile
    1040                1045                1050

Val Gly Cys Asp Asp Glu Thr Tyr Val Gly Ile Arg Tyr Phe Lys
    1055                1060                1065

Val Phe Asn Thr Glu Leu Asp Lys Thr Glu Ile Glu Thr Leu Tyr
    1070                1075                1080

Ser Asn Glu Pro Asp Pro Ser Ile Leu Lys Asn Tyr Trp Gly Asn
    1085                1090                1095

Tyr Leu Leu Tyr Asn Lys Lys Tyr Tyr Leu Phe Asn Leu Leu Arg
    1100                1105                1110

Lys Asp Lys Tyr Ile Thr Leu Asn Ser Gly Ile Leu Asn Ile Asn
    1115                1120                1125

Gln Gln Arg Gly Val Thr Glu Gly Ser Val Phe Leu Asn Tyr Lys
    1130                1135                1140

Leu Tyr Glu Gly Val Glu Val Ile Ile Arg Lys Asn Gly Pro Ile
    1145                1150                1155

Asp Ile Ser Asn Thr Asp Asn Phe Val Arg Lys Asn Asp Leu Ala
    1160                1165                1170

Tyr Ile Asn Val Val Asp Arg Gly Val Glu Tyr Arg Leu Tyr Ala
    1175                1180                1185

Asp Thr Lys Ser Glu Lys Glu Lys Ile Ile Arg Thr Ser Asn Leu
    1190                1195                1200

Asn Asp Ser Leu Gly Gln Ile Ile Val Met Asp Ser Ile Gly Asn
    1205                1210                1215

Asn Cys Thr Met Asn Phe Gln Asn Asn Asn Gly Ser Asn Ile Gly
    1220                1225                1230

Leu Leu Gly Phe His Ser Asn Asn Leu Val Ala Ser Ser Trp Tyr
    1235                1240                1245

Tyr Asn Asn Ile Arg Arg Asn Thr Ser Ser Asn Gly Cys Phe Trp
    1250                1255                1260

Ser Ser Ile Ser Lys Glu Asn Gly Trp Lys Glu
    1265                1270
```

<210> SEQ ID NO 10
<211> LENGTH: 1297
<212> TYPE: PRT
<213> ORGANISM: Clostridium botulinum

<400> SEQUENCE: 10

-continued

```
Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
            165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
            195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
            245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
            325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415
```

```
Lys Glu Ala Tyr Glu Glu Ile Ser Leu Glu His Leu Val Ile Tyr Arg
            420             425                 430

Ile Ala Met Cys Lys Pro Val Met Tyr Lys Asn Thr Gly Lys Ser Glu
            435             440             445

Gln Cys Ile Ile Val Asn Asn Glu Asp Leu Phe Phe Ile Ala Asn Lys
            450             455             460

Asp Ser Phe Ser Lys Asp Leu Ala Lys Ala Glu Thr Ile Ala Tyr Asn
465             470             475                 480

Thr Gln Asn Asn Thr Ile Glu Asn Asn Phe Ser Ile Asp Gln Leu Ile
                485             490                 495

Leu Asp Asn Asp Leu Ser Ser Gly Ile Asp Leu Pro Asn Glu Asn Thr
            500             505             510

Glu Pro Phe Thr Asn Phe Asp Asp Ile Asp Ile Pro Val Tyr Ile Lys
            515             520             525

Gln Ser Ala Leu Lys Lys Ile Phe Val Asp Gly Asp Ser Leu Phe Glu
            530             535             540

Tyr Leu His Ala Gln Thr Phe Pro Ser Asn Ile Glu Asn Leu Gln Leu
545             550             555                 560

Thr Asn Ser Leu Asn Asp Ala Leu Arg Asn Asn Asn Lys Val Tyr Thr
                565             570             575

Phe Phe Ser Thr Asn Leu Val Glu Lys Ala Asn Thr Val Val Gly Ala
            580             585             590

Ser Leu Phe Val Asn Trp Val Lys Gly Val Ile Asp Asp Phe Thr Ser
            595             600             605

Glu Ser Thr Gln Lys Ser Thr Ile Asp Lys Val Ser Asp Val Ser Ile
            610             615             620

Ile Ile Pro Tyr Ile Gly Pro Ala Leu Asn Val Gly Asn Glu Thr Ala
625             630             635                 640

Lys Glu Asn Phe Lys Asn Ala Phe Glu Ile Gly Gly Ala Ala Ile Leu
                645             650             655

Met Glu Phe Ile Pro Glu Leu Ile Val Pro Ile Val Gly Phe Phe Thr
            660             665             670

Leu Glu Ser Tyr Val Gly Asn Lys Gly His Ile Ile Met Thr Ile Ser
            675             680             685

Asn Ala Leu Lys Lys Arg Asp Gln Lys Trp Thr Asp Met Tyr Gly Leu
            690             695             700

Ile Val Ser Gln Trp Leu Ser Thr Val Asn Thr Gln Phe Tyr Thr Ile
705             710             715                 720

Lys Glu Arg Met Tyr Asn Ala Leu Asn Asn Gln Ser Gln Ala Ile Glu
                725             730             735

Lys Ile Ile Glu Asp Gln Tyr Asn Arg Tyr Ser Glu Glu Asp Lys Met
            740             745             750

Asn Ile Asn Ile Asp Phe Asn Asp Ile Asp Phe Lys Leu Asn Gln Ser
            755             760             765

Ile Asn Leu Ala Ile Asn Asn Ile Asp Asp Phe Ile Asn Gln Cys Ser
            770             775             780

Ile Ser Tyr Leu Met Asn Arg Met Ile Pro Leu Ala Val Lys Lys Leu
785             790             795                 800

Lys Asp Phe Asp Asp Asn Leu Lys Arg Asp Leu Leu Glu Tyr Ile Asp
                805             810             815

Thr Asn Glu Leu Tyr Leu Leu Asp Glu Val Asn Ile Leu Lys Ser Lys
            820             825             830

Val Asn Arg His Leu Lys Asp Ser Ile Pro Phe Asp Leu Ser Leu Tyr
```

-continued

```
                835                840                845
Thr Lys Asp Thr Ile Leu Ile Gln Val Phe Asn Asn Tyr Ile Ser Asn
    850                855                860
Ile Ser Ser Asn Ala Ile Leu Ser Leu Ser Tyr Arg Gly Gly Arg Leu
865                870                875                880
Ile Asp Ser Ser Gly Tyr Gly Ala Thr Met Asn Val Gly Ser Asp Val
                885                890                895
Ile Phe Asn Asp Ile Gly Asn Gly Gln Phe Lys Leu Asn Asn Ser Glu
                900                905                910
Asn Ser Asn Ile Thr Ala His Gln Ser Lys Phe Val Val Tyr Asp Ser
                915                920                925
Met Phe Asp Asn Phe Ser Ile Asn Phe Trp Val Arg Thr Pro Lys Tyr
    930                935                940
Asn Asn Asn Asp Ile Gln Thr Tyr Leu Gln Asn Glu Tyr Thr Ile Ile
945                950                955                960
Ser Cys Ile Lys Asn Asp Ser Gly Trp Lys Val Ser Ile Lys Gly Asn
                965                970                975
Arg Ile Ile Trp Thr Leu Ile Asp Val Asn Ala Lys Ser Lys Ser Ile
                980                985                990
Phe Phe Glu Tyr Ser Ile Lys Asp  Asn Ile Ser Asp Tyr  Ile Asn Lys
                995                1000               1005
Trp Phe  Ser Ile Thr Ile Thr  Asn Asp Arg Leu Gly  Asn Ala Asn
    1010               1015               1020
Ile Tyr  Ile Asn Gly Ser Leu  Lys Lys Ser Glu Lys  Ile Leu Asn
    1025               1030               1035
Leu Asp  Arg Ile Asn Ser Ser  Asn Asp Ile Asp Phe  Lys Leu Ile
    1040               1045               1050
Asn Cys  Thr Asp Thr Thr Lys  Phe Val Trp Ile Lys  Asp Phe Asn
    1055               1060               1065
Ile Phe  Gly Arg Glu Leu Asn  Ala Thr Glu Val Ser  Ser Leu Tyr
    1070               1075               1080
Trp Ile  Gln Ser Ser Thr Asn  Thr Leu Lys Asp Phe  Trp Gly Asn
    1085               1090               1095
Pro Leu  Arg Tyr Asp Thr Gln  Tyr Tyr Leu Phe Asn  Gln Gly Met
    1100               1105               1110
Gln Asn  Ile Tyr Ile Lys Tyr  Phe Ser Lys Ala Ser  Met Gly Glu
    1115               1120               1125
Thr Ala  Pro Arg Thr Asn Phe  Asn Asn Ala Ala Ile  Asn Tyr Gln
    1130               1135               1140
Asn Leu  Tyr Leu Gly Leu Arg  Phe Ile Ile Lys Lys  Ala Ser Asn
    1145               1150               1155
Ser Arg  Asn Ile Asn Asn Asp  Asn Ile Val Arg Glu  Gly Asp Tyr
    1160               1165               1170
Ile Tyr  Leu Asn Ile Asp Asn  Ile Ser Asp Glu Ser  Tyr Arg Val
    1175               1180               1185
Tyr Val  Leu Val Asn Ser Lys  Glu Ile Gln Thr Gln  Leu Phe Leu
    1190               1195               1200
Ala Pro  Ile Asn Asp Asp Pro  Thr Phe Tyr Asp Val  Leu Gln Ile
    1205               1210               1215
Lys Lys  Tyr Tyr Glu Lys Thr  Thr Tyr Asn Cys Gln  Ile Leu Cys
    1220               1225               1230
Glu Lys  Asp Thr Lys Thr Phe  Gly Leu Phe Gly Ile  Gly Lys Phe
    1235               1240               1245
```

```
Val Lys  Asp Tyr Gly Tyr Val  Trp Asp Thr Tyr Asp  Asn Tyr Phe
    1250             1255              1260

Cys Ile  Ser Gln Trp Tyr Leu  Arg Arg Ile Ser Glu  Asn Ile Asn
    1265             1270              1275

Lys Leu  Arg Leu Gly Cys Asn  Trp Gln Phe Ile Pro  Val Asp Glu
    1280             1285              1290

Gly Trp  Thr Glu
    1295

<210> SEQ ID NO 11
<211> LENGTH: 1291
<212> TYPE: PRT
<213> ORGANISM: Clostridium botulinum

<400> SEQUENCE: 11

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Gln Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
```

```
305              310              315              320

Lys Asn Lys Phe Lys Asp Lys Tyr Lys Phe Val Glu Asp Ser Glu Gly
                325              330              335

Lys Tyr Ser Ile Asp Val Glu Ser Phe Asn Lys Leu Tyr Lys Ser Leu
            340              345              350

Met Phe Gly Phe Thr Glu Ile Asn Ile Ala Glu Asn Tyr Lys Ile Lys
            355              360              365

Thr Arg Ala Ser Tyr Phe Ser Asp Ser Leu Pro Pro Val Lys Ile Lys
        370              375              380

Asn Leu Leu Asp Asn Glu Ile Tyr Thr Ile Glu Glu Gly Phe Asn Ile
385              390              395              400

Ser Asp Lys Asn Met Gly Lys Glu Tyr Arg Gly Gln Asn Lys Ala Ile
                405              410              415

Asn Lys Gln Ala Tyr Glu Glu Ile Ser Lys Glu His Leu Ala Val Tyr
            420              425              430

Lys Ile Gln Met Cys Lys Ser Val Lys Val Pro Gly Ile Cys Ile Asp
            435              440              445

Val Asp Asn Glu Asn Leu Phe Phe Ile Ala Asp Lys Asn Ser Phe Ser
        450              455              460

Asp Asp Leu Ser Lys Asn Glu Arg Val Glu Tyr Asn Thr Gln Asn Asn
465              470              475              480

Tyr Ile Gly Asn Asp Phe Pro Ile Asn Glu Leu Ile Leu Asp Thr Asp
                485              490              495

Leu Ile Ser Lys Ile Glu Leu Pro Ser Glu Asn Thr Glu Ser Leu Thr
            500              505              510

Asp Phe Asn Val Asp Val Pro Val Tyr Glu Lys Gln Pro Ala Ile Lys
            515              520              525

Lys Val Phe Thr Asp Glu Asn Thr Ile Phe Gln Tyr Leu Tyr Ser Gln
        530              535              540

Thr Phe Pro Leu Asn Ile Arg Asp Ile Ser Leu Thr Ser Ser Phe Asp
545              550              555              560

Asp Ala Leu Leu Val Ser Ser Lys Val Tyr Ser Phe Phe Ser Met Asp
            565              570              575

Tyr Ile Lys Thr Ala Asn Lys Val Val Glu Ala Gly Leu Phe Ala Gly
            580              585              590

Trp Val Lys Gln Ile Val Asp Asp Phe Val Ile Glu Ala Asn Lys Ser
        595              600              605

Ser Thr Met Asp Lys Ile Ala Asp Ile Ser Leu Ile Val Pro Tyr Ile
        610              615              620

Gly Leu Ala Leu Asn Val Gly Asp Glu Thr Ala Lys Gly Asn Phe Glu
625              630              635              640

Ser Ala Phe Glu Ile Ala Gly Ser Ser Ile Leu Leu Glu Phe Ile Pro
            645              650              655

Glu Leu Leu Ile Pro Val Val Gly Val Phe Leu Leu Glu Ser Tyr Ile
            660              665              670

Asp Asn Lys Asn Lys Ile Ile Lys Thr Ile Asp Asn Ala Leu Thr Lys
        675              680              685

Arg Val Glu Lys Trp Ile Asp Met Tyr Gly Leu Ile Val Ala Gln Trp
        690              695              700

Leu Ser Thr Val Asn Thr Gln Phe Tyr Thr Ile Lys Glu Gly Met Tyr
705              710              715              720

Lys Ala Leu Asn Tyr Gln Ala Gln Ala Leu Glu Glu Ile Ile Lys Tyr
            725              730              735
```

```
Lys Tyr Asn Ile Tyr Ser Glu Glu Glu Lys Ser Asn Ile Asn Ile Asn
            740                 745                 750

Phe Asn Asp Ile Asn Ser Lys Leu Asn Asp Gly Ile Asn Gln Ala Met
            755                 760                 765

Asp Asn Ile Asn Asp Phe Ile Asn Glu Cys Ser Val Ser Tyr Leu Met
770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
            820                 825                 830

Lys Thr Ile Ile Pro Phe Asp Leu Ser Thr Tyr Thr Asn Asn Glu Ile
            835                 840                 845

Leu Ile Lys Ile Phe Asn Lys Tyr Asn Ser Glu Ile Leu Asn Asn Ile
            850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
            900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Arg Asn Asp Asp Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
            995                 1000                1005

Asn Asn  Leu Asp Asn Ala Lys  Ile Tyr Ile Asn Gly  Thr Leu Glu
    1010                1015                1020

Ser Asn  Met Asp Ile Lys Asp  Ile Gly Glu Val Ile  Val Asn Gly
    1025                1030                1035

Glu Ile  Thr Phe Lys Leu Asp  Gly Asp Val Asp Arg  Thr Gln Phe
    1040                1045                1050

Ile Trp  Met Lys Tyr Phe Ser  Ile Phe Asn Thr Gln  Leu Asn Gln
    1055                1060                1065

Ser Asn  Ile Lys Glu Ile Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Val
    1100                1105                1110

Lys Asp  Ser Ser Val Gly Glu  Ile Leu Ile Arg Ser  Lys Tyr Asn
    1115                1120                1125

Gln Asn  Ser Asn Tyr Ile Asn  Tyr Arg Asn Leu Tyr  Ile Gly Glu
    1130                1135                1140
```

-continued

```
Lys Phe  Ile Ile Arg Arg Lys  Ser Asn Ser Gln Ser  Ile Asn Asp
    1145              1150              1155

Asp Ile  Val Arg Lys Glu Asp  Tyr Ile His Leu Asp  Phe Val Asn
    1160              1165              1170

Ser Asn  Glu Glu Trp Arg Val  Tyr Ala Tyr Lys Asn  Phe Lys Glu
    1175              1180              1185

Gln Glu  Gln Lys Leu Phe Leu  Ser Ile Ile Tyr Asp  Ser Asn Glu
    1190              1195              1200

Phe Tyr  Lys Thr Ile Gln Ile  Lys Glu Tyr Asp Glu  Gln Pro Thr
    1205              1210              1215

Tyr Ser  Cys Gln Leu Leu Phe  Lys Lys Asp Glu Glu  Ser Thr Asp
    1220              1225              1230

Asp Ile  Gly Leu Ile Gly Ile  His Arg Phe Tyr Glu  Ser Gly Val
    1235              1240              1245

Leu Arg  Lys Lys Tyr Lys Asp  Tyr Phe Cys Ile Ser  Lys Trp Tyr
    1250              1255              1260

Leu Lys  Glu Val Lys Arg Lys  Pro Tyr Lys Ser Asn  Leu Gly Cys
    1265              1270              1275

Asn Trp  Gln Phe Ile Pro Lys  Asp Glu Gly Trp Thr  Glu
    1280              1285              1290

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic HA tag"

<400> SEQUENCE: 12

Tyr Pro Tyr Asp Val Pro Asp Tyr Ala
1               5

<210> SEQ ID NO 13
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 13

His His His His His His
1               5

<210> SEQ ID NO 14
<211> LENGTH: 22
<212> TYPE: PRT
<213> ORGANISM: Homo sapiens

<400> SEQUENCE: 14

Gly Glu Ser Gln Glu Asp Met Phe Ala Lys Leu Lys Glu Lys Leu Phe
1               5                   10                  15

Asn Glu Ile Asn Lys Ile
            20
```

ENGINEERED BOTULINUM NEUROTOXIN

RELATED APPLICATIONS

This Application is a divisional of U.S. application Ser. No. 15/561,355, filed Sep. 25, 2017, which is a National Stage of International Application No. PCT/US16/24211, filed Mar. 25, 2016, which claims the benefit under 35 U.S.C. § 119 (e) of U.S. Provisional Application Ser. No. 62/138,818, filed Mar. 26, 2015, the contents of each of which are incorporated herein by reference in their entirety.

GOVERNMENTAL SUPPORT

This invention was made with Government support under NIH NCRR RR000168 awarded by the National Institute of Health. The Government has certain rights in the invention.

SEQUENCE LISTING

In accordance with 37 CFR § 1.52 (e) (5), the present specification makes reference to a Sequence Listing (submitted electronically as a .txt file named "0342941_0811_SL.TXT"). The .txt file was generated on May 5, 2016, and is 95,818 bytes in size. The entire contents of the Sequence Listing are herein incorporated by reference.

FIELD OF THE INVENTION

The present invention relates to the field of modified neurotoxins and their use for treating medical and/or aesthetic disorders.

BACKGROUND OF THE INVENTION

Botulinum neurotoxins are a family of bacterial toxins, including seven major serotypes (BoNT/A-G)[1]. These toxins act by blocking neurotransmitter release from neurons, thus paralyzing animals and humans. In recent years, BoNTs have been widely used to treat a growing list of medical conditions: local injections of minute amount of toxins can attenuate neuronal activity in targeted regions, which can be beneficial in many medical conditions as well as for cosmetic purposes[2-4].

BoNT/A and BoNT/B are the only two BoNTs that are currently FDA-approved for use in humans[2-4]. These are toxins purified from bacteria without any sequence modifications (defined as wild type, WT). As the application of BoNTs grows, limitations and adverse effects have been reported. The major limitation is the generation of neutralizing antibodies in patients, which renders future treatment ineffective[5]. Termination of BoNT usage often leaves patients with no other effective ways to treat/relieve their disorders. The possibility of antibody responses is directly related to both toxin doses and the frequency of injection[5]. Therefore, this limitation mainly occurs in treating muscle spasms, which involves relatively high doses of toxins. Consistently, antibody responses have not been observed in cosmetic applications, which use extremely low toxin doses[5].

The major adverse effects are also often associated with treating muscle spasms, but not cosmetic applications. This is because the adverse effects are largely due to diffusion of toxins to other regions of the body and the possibility of toxin diffusion is directly related to injected doses. The adverse effects ranges from transient non-serious events such as ptosis and diplopia to life-threatening events even death[6,7]. In a petition letter filed in 2008 by Dr. Sidney Wolfe to FDA, a total of 180 serious adverse events, including 16 deaths have been documented. As a result, FDA now requires the "Black box warning" on all BoNT products, highlighting the risk of the spread of toxins, following similar warnings issued by the European Union.

Because both the generation of neutralizing antibodies and toxin diffusion are directly related to injected doses, lowering toxin doses (while maintaining the same levels of toxin activity) is highly desired, which means the efficacy of individual toxin molecules has to be enhanced. Such modified BoNTs with improved specificity for neurons will also reduce any potential off-target effects due to non-specific entry into other cell types.

BoNTs target and enter neurons by binding to their specific receptors through their receptor binding domains, which are well-defined in the literature (BoNT-H$_C$, FIG. 1A, B)[1]. Receptor binding dictates the efficacy and specificity of BoNTs to recognize neurons. Improving the receptor binding ability of BoNTs will enhance their efficacy and specificity to target neurons. The receptors for most BoNTs have been identified (FIG. 1C), BoNT/B, D-C, and G share two homologous synaptic vesicle proteins synaptotagmin I and II (Syt I/II) as their receptors[8-13], while BoNT/A, E, D, and F use another synaptic vesicle protein SV2[9,14-18]. In addition to protein receptors, all BoNTs require lipid co-receptor gangliosides (FIG. 1D), which are abundant on neuronal surfaces[19]. Among the two Syt isoforms Syt II has ~10-fold higher binding affinity for BoNT/B than Syt I and is also the dominant isoform expressed in motor nerve terminals, which are the targeted neurons for BoNTs (FIG. 2A)[20,21] Therefore, Syt II is considered the major toxin receptor for BoNT/B, D-C, and G, while Syt I is a minor toxin receptor at motor nerve terminals. This is the case in rodents and likely in the majority of mammals.

One may argue that BoNTs already have high specificity to neurons, and ask is it possible to further improve their binding to neurons? The answer is a "Yes" for humans, at least in part in light of the recent discovery that the human Syt II has greatly diminished binding and function as the receptor for BoNT/B due to a unique amino acid change from rodent (rat/mouse) Syt II within the toxin binding site[13,22]. This is a change from phenylalanine (F) to leucine (L) at position 54 (mouse Syt II sequence) (FIG. 2B). Sequence alignments have revealed that phenylalanine at this position is highly conserved in both Syt I and Syt II across vertebrates, including platypus, fish, rodents, and monkeys[23]. Only human and chimpanzee Syt II contains leucine at this position. As a result of this residue change, human and chimpanzee Syt II has greatly diminished binding to BoNT/B, D-C, and G (FIG. 2C) and is significantly less efficient in mediating the entry of BoNT/B (FIG. 2D), as compared to mouse Syt II. Since human and chimpanzee Syt I still contains phenylalanine at the same position and can bind BoNT/B, D-C, and G (FIG. 2E), the high affinity receptor for BoNT/B, D-C, and G in humans is restricted to the minor receptor Syt I. These findings provide an explanation for the clinical observations that a much higher dose of BoNT/B than BoNT/A (which binds a different receptor) is needed to achieve the same levels of therapeutic effects in patients[24,25] Previously these observations were attributed to other reasons, such as the percentage of active neurotoxin in the preparations used. The recent observations of such binding differences of BoNT/B to human Syt II versus Syt II of other species suggests that different residues of BoNT/B may be involved in binding to human Syt II. As such, sequence modification to BoNT/B that is expected to affect binding to rodent SytII may have unpredictable effects on BoNT/B binding to human Syt II.

Thus there is a great need to improve binding of BoNT/B to human receptor Syt II, as a way to increase its efficacy and specificity to target human neurons and decrease the toxin doses needed in therapeutic applications.

SUMMARY OF THE INVENTION

One aspect of the invention relates to a botulinum neurotoxin (BoNT) polypeptide comprising a protease domain, a protease cleavage site, a translocation domain, and a modified receptor binding domain of *Clostridial botulinum* serotype B (B-H$_c$), comprising one or more substitution mutations corresponding to substitution mutations in serotype B, strain 1, selected from the group consisting of E1191C, E1191V, E1191L, E1191Y, S1199W, S1199E, S1199H, W1178Y, W1178Q, W1178A, W1178S, Y1183C, Y1183P, and combinations thereof. In one embodiment, the modified (B-H$_c$) comprises one substitution mutation corresponding to a substitution mutation in serotype B, strain 1, selected from the group consisting of E1191C, E1191V, E1191L, E1191Y, S1199E, S1199H, W1178Y, W1178Q, W1178A, W1178S, Y1183C, and Y1183P. In one embodiment of the polypeptides described herein the modified (B-H$_c$) comprises the substitution mutation corresponding to E1191C in serotype B, strain 1. In one embodiment of the polypeptides described herein the modified (B-H$_c$) comprises the substitution mutation corresponding to E1191V in serotype B, strain 1. In one embodiment of the polypeptides described herein the modified (B-H$_c$) comprises two substitution mutations.

Another aspect of the invention relates to a botulinum neurotoxin (BoNT) polypeptide comprising a protease domain, a protease cleavage site, a translocation domain, and a modified receptor binding domain of *Clostridial botulinum* serotype B (B-H$_c$), comprising two or more substitution mutations corresponding to substitution mutations in serotype B, strain 1, wherein one of the substitution mutations is selected from the group consisting of E1191Q, E1191M, E1191C, E1191V, E1191L, and E1191Y. In one embodiment, one other of the substitution mutations corresponds to S1199W, S1199E, S1199H, S1199Y, W1178Y, W1178Q, W1178A, W1178S, Y1183C, Y1183P, S1199F or S1199L in serotype B, strain 1. In one embodiment of the polypeptides described herein the two substitution mutations correspond to E1191M and S1199W, E1191M and W1178Q, E1191C and S1199W; E1191C and S1199Y, E1191C and W1178Q, E1191Q and S1199W, E1191V and S1199W, E1191V and S1199Y, or E1191V and W1178Q, in serotype B, strain 1. In one embodiment of the polypeptides described herein the two substitution mutations correspond to E1191M and S1199W in serotype B, strain 1. In one embodiment of the polypeptides described herein the two substitution mutations correspond to E1191M and W1178Q in serotype B, strain 1. In one embodiment of the polypeptides described herein the two substitution mutations correspond to E1191C and S1199W in serotype B, strain 1. In one embodiment of the polypeptides described herein the two substitution mutations correspond to E1191C and S1199Y in serotype B, strain 1. In one embodiment of the polypeptides described herein the two substitution mutations correspond to E1191C and W1178Q in serotype B, strain 1. In one embodiment of the polypeptides described herein the two substitution mutations correspond to E1191Q and S1199W in serotype B, strain 1. In one embodiment of the polypeptides described herein the two substitution mutations correspond to E1191V and S1199W in serotype B, strain 1. In one embodiment of the polypeptides described herein the two substitution mutations correspond to E1191V and S1199Y in serotype B, strain 1. In one embodiment of the polypeptides described herein the two substitution mutations correspond to E1191V and W1178Q in serotype B, strain 1. In one embodiment of the polypeptides described herein the modified (B-H$_c$) comprises three substitution mutations. In one embodiment of the polypeptides described herein the three substitution mutations are at positions that correspond to E1191, Y1183 and S1199 or to E1191, S1199 and W1178 of serotype B, strain 1. In one embodiment of the polypeptides described herein the three substitution mutations correspond to E1191M, S1199W and W1178Q of serotype B, strain 1.

Another aspect of the invention relates to a botulinum neurotoxin (BoNT) polypeptide comprising a protease domain, a protease cleavage site, a translocation domain, and a modified receptor binding domain of *Clostridial botulinum* serotype B (B-H$_c$), comprising a substitution mutation at a position corresponding to S1199 or S1201 of serotype B, strain 1.

In one embodiment of any of the polypeptides described herein the modified B-H$_c$ is of strain 1. In one embodiment of any of the polypeptides described herein the protease domain, translocation domain, and protease cleavage site are from serotype selected from the group consisting of A, B, C, D, E, F, G, and combinations thereof. In one embodiment of any of the polypeptides described herein the protease domain, translocation domain, and protease cleavage site are from serotype B, strain 1. In one embodiment of any of the polypeptides described herein the protease domain, translocation domain, and protease cleavage site are from serotype A, strain 1. In one embodiment of any of the polypeptides described herein, the modified B-Hc is not of strain B4.

Another aspect of the invention relates to a polypeptide comprising a modified receptor binding domain of *Clostridial botulinum* serotype B (B-H$_c$) comprising one or more substitution mutations corresponding to substitution mutations in serotype B, strain 1, selected from the group consisting of E1191C, E1191V, E1191L, E1191Y, S1199W, S1199E, S1199H, W1178Y, W1178Q, W1178A, W1178S, Y1183C, Y1183P, and combinations thereof. In one embodiment, the modified (B-H$_c$) comprises two substitution mutations.

Another aspect of the invention relates to a polypeptide comprising a modified receptor binding domain of *Clostridial botulinum* serotype B (B-H$_c$) comprising two or more substitution mutations corresponding to substitution mutations in serotype B, strain 1, wherein one of the substitution mutations is selected from the group consisting of E1191Q, E1191M, E1191C, E1191V, E1191L, and E1191Y. In one embodiment of the polypeptides described herein one of the substitution mutations corresponds to S1199W, S1199E, S1199H, S1199Y, W1178Y, W1178Q, W1178A, W1178S, Y1183C, Y1183P, S1199F or S1199L in serotype B, strain 1. In one embodiment of the polypeptides described herein the two substitution mutations correspond to E1191M and S1199W, E1191M and W1178Q, E1191C and S1199W; E1191C and S1199Y, E1191C and W1178Q, E1191Q and S1199W, E1191V and S1199W, E1191V and S1199Y, or E1191V and W1178Q, in serotype B, strain 1. In one embodiment of the polypeptides described herein the two substitution mutations correspond to E1191M and S1199W in serotype B, strain 1. In one embodiment of the polypeptides described herein the two substitution mutations correspond to E1191M and W1178Q in serotype B, strain 1.

In one embodiment of the polypeptides described herein the two substitution mutations correspond to E1191C and S1199W in serotype B, strain 1. In one embodiment of the polypeptides described herein the two substitution mutations correspond to E1191C and S1199Y in serotype B, strain 1. In one embodiment of the polypeptides described herein the two substitution mutations correspond to E1191C and W1178Q in serotype B, strain. In one embodiment of the polypeptides described herein the two substitution mutations correspond to E1191Q and S1199W in serotype B, strain 1. In one embodiment of the polypeptides described herein the two substitution mutations correspond to E1191V and S1199W in serotype B, strain 1. In one embodiment of the polypeptides described herein the two substitution mutations correspond to E1191V and S1199Y in serotype B, strain 1. In one embodiment of the polypeptides described herein the two substitution mutations correspond to E1191V and W1178Q in serotype B, strain 1. In one embodiment of the polypeptides described herein the modified (B-H$_c$) comprises three substitution mutations. In one embodiment of the polypeptides described herein the three substitution mutations are at positions that correspond to E1191, Y1183 and S1199 or to E1191, S1199 and W1178 of serotype B, strain 1. In one embodiment of the polypeptides described herein the three substitution mutations correspond to E1191M, S1199W and W1178Q of serotype B, strain 1. In one embodiment of the polypeptides described herein the modified B-H$_c$ is of strain 1. In one embodiment of the polypeptides described herein the modified B-Hc is not of strain 4. In one embodiment, the modified B-Hc is not of strain 3, 7 or 8.

Another aspect of the invention relates to a chimeric molecule comprising a first portion that is a modified receptor binding domain of *Clostridial botulinum* serotype B (B-H$_c$) linked to a second portion, wherein the modified B-H$_c$ comprises one or more substitution mutations selected from the group consisting of E1191C, E1191V, E1191L, E1191Y, S1199W, S1199E, S1199H, W1178Y, W1178Q, W1178A, W1178S, Y1183C, Y1183P, and combinations thereof. In one embodiment the modified B-H$_c$ comprises two substitution mutations.

Another aspect of the invention relates to a chimeric molecule comprising a first portion that is a modified receptor binding domain of *Clostridial botulinum* serotype B (B-H$_c$) linked to a second portion, wherein the modified B-H$_c$ comprises two or more substitution mutations corresponding to substitution mutations in serotype B, strain 1, wherein one of the substitution mutations is selected from the group consisting of E1191Q, E1191M, E1191C, E1191V, E1191L, and E1191Y. In one embodiment of the chimeric molecules described herein one of the substitution mutations corresponds to S1199W, S1199E, S1199H, S1199Y, W1178Y, W1178Q, W1178A, W1178S, Y1183C, Y1183P, S1199F or S1199L in serotype B, strain 1. In one embodiment of the chimeric molecules described herein the two substitution mutations correspond to E1191M and S1199W, E1191M and W1178Q, E1191C and S1199W; E1191C and S1199Y, E1191C and W1178Q, E1191Q and S1199W, E1191V and S1199W, E1191V and S1199Y, or E1191V and W1178Q, in serotype B, strain 1. In one embodiment of the chimeric molecules described herein the two substitution mutations correspond to E1191M and S1199W in serotype B, strain 1. In one embodiment of the chimeric molecules described herein the two substitution mutations correspond to E1191M and W1178Q in serotype B, strain 1. In one embodiment of the chimeric molecules described herein the two substitution mutations correspond to E1191C and S1199W in serotype B, strain 1. In one embodiment of the chimeric molecules described herein the two substitution mutations correspond to E1191C and S1199Y in serotype B, strain 1. In one embodiment of the chimeric molecules described herein the two substitution mutations correspond to E1191C and W1178Q in serotype B, strain 1. In one embodiment of the chimeric molecules described herein the two substitution mutations correspond to E1191Q and S1199W in serotype B, strain 1. In one embodiment of the chimeric molecules described herein the two substitution mutations correspond to E1191V and S1199W in serotype B, strain 1. In one embodiment of the chimeric molecules described herein the two substitution mutations correspond to E1191V and S1199Y in serotype B, strain 1. In one embodiment of the chimeric molecules described herein the two substitution mutations correspond to E1191V and W1178Q in serotype B, strain 1. In one embodiment of the chimeric molecules described herein the modified (B-H$_c$) comprises three substitution mutations. In one embodiment of the chimeric molecules described herein the three substitution mutations are at positions that correspond to E1191, Y1183 and S1199 or to E1191, S1199 and W1178 of serotype B, strain 1. In one embodiment of the chimeric molecules described herein the three substitution mutations correspond to E1191M, S1199W and W1178Q of serotype B, strain 1.

In one embodiment of any of the chimeric molecules described herein the modified B-H$_c$ is of strain 1. In one embodiment of any of the chimeric molecules described herein, the modified B-Hc is not of strain 4. In one embodiment, the modified B-Hc is not of strain 3, 7 or 8.

In one embodiment of any of the chimeric molecules described herein the first portion and the second portion are linked covalently. In one embodiment of any of the chimeric molecules described herein the first portion and the second portion are linked non-covalently. In one embodiment of any of the chimeric molecules described herein the second portion is selected from the group consisting of a small molecule, a nucleic acid, a short polypeptide and a protein. In one embodiment of any of the chimeric molecules described herein the second portion is a bioactive molecule. In one embodiment of any of the chimeric molecules described herein the second portion is a therapeutic polypeptide or non-polypeptide drug.

Aspects of the invention further relate to any of the BoNT polypeptides, polypeptides or chimeric molecules described herein that exhibits significantly enhanced binding of the modified B-Hc to human SytII and/or significantly reduced binding of the modified B-Hc to human Syt I as compared to an identical molecule lacking the substitution mutation(s).

Aspects of the invention further relate to any of the BoNT polypeptides, polypeptides or chimeric molecules described herein wherein the substitution mutation produces significantly enhanced binding to human SytII and/or significantly enhanced binding to human Syt I as compared to an identical molecule lacking the substitution mutation(s).

Another aspect of the invention relates to a nucleic acid comprising a nucleotide sequence that encodes the BoNT polypeptide, polypeptide or chimeric molecule described herein. Another aspect of the invention relates to a nucleic acid vector comprising the nucleic acid comprising a nucleotide sequence that encodes the BoNT polypeptide, polypeptide or chimeric molecule described herein. Another aspect of the invention relates to a cell comprising the nucleic acid comprising a nucleotide sequence that encodes the BoNT polypeptide, polypeptide or chimeric molecule described herein, or the nucleic acid vector comprising the nucleic acid.

Another aspect of the invention relates to a cell expressing any of the BoNT polypeptides, polypeptides or chimeric molecules described herein.

Another aspect of the invention relates to a pharmaceutical composition comprising any of the botulinum neurotoxin (BoNT) polypeptides described herein.

Another aspect of the invention relates to a pharmaceutical composition comprising any of the polypeptides described herein.

Another aspect of the invention relates to a pharmaceutical composition comprising any of the chimeric molecules described herein.

Another aspect of the invention relates to a pharmaceutical composition comprising any of the nucleic acids or nucleic acid vectors described herein.

In one embodiment of any of the pharmaceutical compositions described herein the pharmaceutical composition further comprises a pharmaceutically acceptable excipient.

Another aspect of the invention relates to a kit comprising any of the pharmaceutical compositions described herein and directions for therapeutic administration of the pharmaceutical composition.

Another aspect of the invention relates to a method to produce any of the botulinum neurotoxin (BoNT) polypeptides described herein, the method comprising the steps of culturing the cell that expresses the BoNT polypeptide under conditions wherein said BoNT polypeptide is produced. In one embodiment, the method further comprises one or more of the steps of recovering the BoNT polypeptide from the culture, purifying the BoNT polypeptide, activating the BoNT polypeptide, and/or formulating the BoNT polypeptide.

Another aspect of the invention relates to a method for treating a condition associated with unwanted neuronal activity comprising administering a therapeutically effective amount of the BoNT polypeptide described herein to a subject to thereby contact one or more neurons' exhibiting unwanted neuronal activity, to thereby treat the condition. In one embodiment, the condition is selected from the group consisting of, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder (i.e. all diseases involving urinary incontinence, such as e.g. neurogenic detrusor overactivity or idiopathic overactive bladder), anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions, secretory disorders, pain from muscle spasms, neuropathic pain, inflammatory pain, headache pain (such as e.g., migraine), itch (pruritis), acne, and dermatological or aesthetic/cosmetic conditions.

Another aspect of the invention relates to any of the botulinum neurotoxin (BoNT) polypeptides or the pharmaceutical compositions, or the chimeric molecules, or the polypeptides described herein for use in medicine.

Another aspect of the invention relates to any of the botulinum neurotoxin (BoNT) polypeptides, or the pharmaceutical compositions, or the chimeric molecules, or the polypeptides described herein, for use in treating a condition associated with unwanted neuronal activity.

Another aspect of the invention relates to a method for identifying a modified receptor binding domain of botulinum neurotoxin for binding to a receptor comprising expressing the modified receptor binding domain as a first fusion protein with T18 subunit of bacterial adenylate cyclase in a 2-hybrid assay, and expressing the receptor as a second fusion protein with T25 subunit of bacterial adenylate cyclase in the 2-hybrid assay, analyzing a clonal *E. coli* colony that expresses both the first and second fusion protein for the presence of a positive indication above a negative control, and identifying the modified receptor binding domain expressed by the colony exhibiting the positive indication as binding to the receptor. In one embodiment, the positive indication is color development. In one embodiment of the methods described herein, the method further comprises the step of analyzing the colony for the positive indication against a weakly positive control, and further identifying the modified receptor binding domain expressed by the colony exhibiting the positive indication above the weakly positive control as binding to the receptor with high affinity. In one embodiment of the methods described herein, the method is performed with a library of modified receptor binding domains each expressed within respective colonies. In one embodiment of the methods described herein, the receptor is human. In one embodiment of the methods described herein, the modified receptor binding domain comprises one or more substitution mutations, wherein one of the substitution mutations corresponds to a mutation in serotype B, strain 1, selected from the group consisting of: E1191M, E1191Q, E1191C, E1191V, E1191L, E1191Y, S1199W, S1199E, S1199H, S1199F, S1199L W1178Y, W1178Q, W1178A, W1178S, Y1183C, Y1183P and S1199Y.

BRIEF DESCRIPTION OF THE DRAWINGS

Figure 1A:
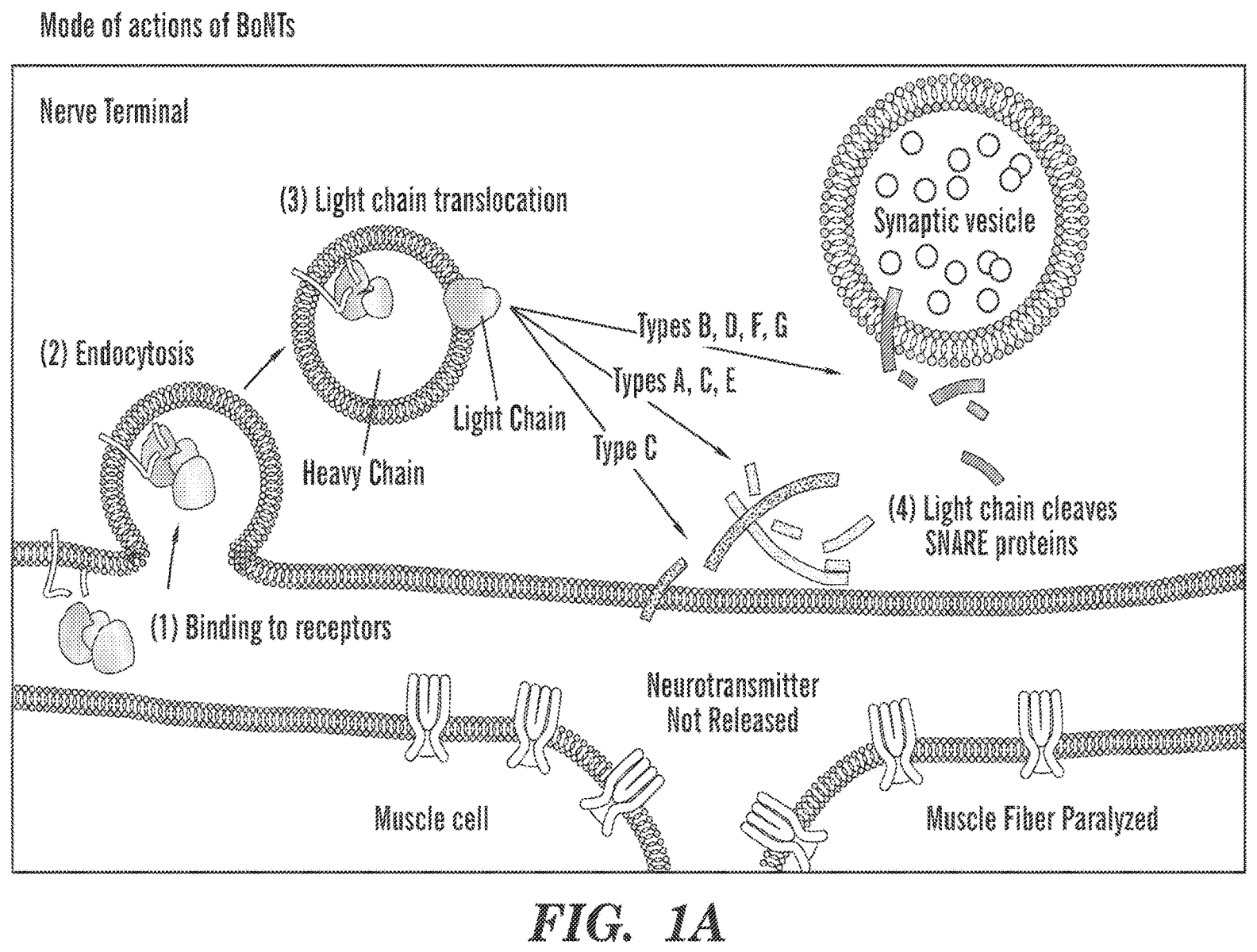

FIG. 1A-FIG. 1D (published data for background) shows schematic models for how BoNTs target neurons (FIG. 1A), their overall protein structure (FIG. 1B), a list of identified receptors (FIG. 1C), and the structural model for BoNT/B binding to its receptors Syt and gangliosides (FIG. 1D). (FIG. 1A) A schematic view of BoNT actions: BoNTs recognize neurons by binding to their specific receptors (step 1), enter neurons via receptor-mediated endocytosis (step 2), the light chains of BoNTs then translocate across endosomal membranes into the cytosol (step 3), where these light chains act as proteases to cleave target host proteins (step 4). FIG. 1A is adapted from Arnon, S. et al. *JAMA*, 285:1059, 2001[24]. (FIG. 1B) BoNTs are composed of a light chain and a heavy chain, connected via a disulfide bond. The heavy chain can be further divided into two domains: the translocation domain ($H_N$) and the receptor binding domain ($H_C$). These functional domains are switchable between different BoNTs. For instance, BoNT/B-$H_C$ can be used to replace BoNT/A-$H_C$ to generate chimeric toxins. (FIG. 1C) A list of identified toxins receptors. (FIG. 1D) A structural model showing binding of BoNT/B to its protein receptor, Syt (I/II), as well as its lipid co-receptor, gangliosides, on the cell surface. FIG. 1D is adapted from Chai et al. *Nature*, 444:1096, 2006[31].

(FIG. 2B) Glutathione S-transferase (GST) tagged recombinant mouse Syt II 1-87 (m-Syt II) and a mouse Syt II 1-87 mutant mimicking human Syt II (F54L, here and thereafter designed as h-Syt II to simplify the text) were immobilized on glutathione-sepharose beads, and were used to pull down BoNT/B, BoNT/D-C, or BoNT/G, with or without the presence of ganglioside (GangI). All three toxins bind to m-Syt II 1-87, but not h-Syt II in the pull-down assays. (FIG. 2C) Cultured rat hippocampal neurons only express Syt I but not Syt II[8]. Therefore, knocking down (KD) Syt I generates neurons with no endogenous toxin receptors. Full-length m-Syt II and h-Syt II were then expressed in Syt I KD hippocampal neurons, and these neurons were exposed to BoNT/B (20 nM, 5 min exposure, 24 hours incubation) or BoNT/D-C (0.3 nM, 5 min exposure, 6 hours incubation) or BoNT/G (40 nM, 5 min exposure, 24 hours incubation), h-Syt II was found significantly less efficient in mediating the entry of BoNT/B, BoNT/D-C, and BoNT/G into Syt I KD neurons as compared to wild type mouse Syt II, as evidenced by the degrees of cleavage of toxin substrate synaptobrevin (Syb). (FIG. 2D) Rat Syt I 1-83 and human Syt I 1-80 were used to pull down BoNT/B, BoNT/D-C, and BoNT/G, as described in panel C. Human Syt I mediated similar levels of toxin binding as rat Syt I did for all three toxins. This figure is adapted from our recent publication: Peng et al. *J. Cell Science,* 2012[13].

FIG. 3A-FIG. 3B shows residues located in the Syt II binding interface on BoNT/B-H$_C$, which are candidates for site-directed mutagenesis to modify the binding affinity. (FIG. 3A) A Close-up view of binding interface between BoNT/B-H$_C$ and mouse Syt II is shown here. Residues in BoNT/B-H$_C$ that contribute to the binding are marked in bold, whereas residues in Syt II are not bold. Residue F54 in Syt II, in the middle and shown in slightly larger font size, changes to residue L in human Syt II. (FIG. 3B) A list of 19 key residues in BoNT/B that form the binding pocket of the Syt II binding domain in BoNT/B. These residues are candidates for site-directed mutagenesis.

(FIG. 4A) A pool of BoNT/B-H$_C$ mutants that covers all 20 different amino acids at the selected position is generated by PCR amplification with primers containing random tri-nucleotides (NNN) at the selected site. A total of 19 distinct pools were generated for all 19 residues selected in FIG. 3B. (FIG. 4B) A schematic illustration of the BACTH system. Briefly, the bacterial adenylate cyclase is split to two domains, designated as T25 and T18. T25 is fused to human Syt II (residues 1-87) that contains the toxin binding site, whereas T18 is fused to BoNT/B-H$_C$ generated as described in FIG. 4A. These two fusion proteins are encoded on two separated plasmids and co-transformed into the same bacteria. Binding of mutated BoNT/B-H$_C$ to human Syt II brings together T25 and T18 domains in bacteria, which restores the activity of the bacterial adenylate cyclase. This leads to production of CAMP in bacteria, which activates CAP protein and triggers expression of the reporter gene lacZ that encodes β-galactosidase. The activity of β-galactosidase leads to blue colonies on X-gal plates that can be easily identified. Plasmids that encode BoNT/B-H$_C$ can be then extracted from blue colonies and sequenced to identify the specific mutations in BoNT/B-H$_C$.

FIG. 5A-FIG. 5B are tables that summarize the results from the BACTH screening of BoNT/B-H$_C$ mutants. (FIG. 5A) List of total colonies and the number of blue colonies for each pool of BoNT/B-H$_C$ mutants fused to T18, co-expressed in bacteria with human Syt II fused to T25. Based on Clark-Carbon Equation, the number of total colonies needs to be larger than 380 to achieve a 99.8% of possibility of covering all 20 possible amino acids at a single position. Four positions resulted in significant numbers of blue colonies (68 hours after plating). (FIG. 5B) Plasmids from blue colonies identified in FIG. 5A were extracted and sequenced to determine the specific residue introduced at the indicated position in BoNT/B-H$_C$. The identified residues are listed. Of note, the blue colonies were further divided to "deep blue colonies", which were found with the position 1191 of BoNT/B-H$_C$, and "light blue colonies", which were found with the positions 1183, 1199, and 1178. The term "deep blue colonies" versus "light blue colonies" were artificially judged by the experimenter based on the differences between the blue color of colonies.

(FIG. 6A) The β-galactosidase activity was measured from lysates of bacteria that express both human Syt II fused with T25 and indicated BoNT/B-H$_C$ mutants fused with T18. The activity of β-galactosidase presumably reflects the strength of interactions between human Syt II and BoNT/B-H$_C$, WT BoNT/B-H$_C$ served as a control. Exchanging residues E1191 to M, C, V, or Q gave the strongest expression of β-galactosidase. Exchanging residues E1191 to S/A/T/N, Y1183 to C/P, S1199 to W/E/Y/H, W1178 to Y/Q/S showed slight increases of interactions. N=6 samples/group. (FIG. 6B) Binding of indicated BoNT/B-H$_C$ mutants to either mouse Syt II (m-Syt II) or human Syt II (h-Syt II), the bindings sites of which are shown in FIG. 2A, was assayed by pull down assay. Exchanging residues E1191 to M, C. V, or Q also showed the strongest binding to h-Syt II.

(FIG. 7A) Double mutations were created by combining E1191M with all other ten residue changes identified in FIG. 5B at positions S1199/Y1183/W1178, respectively. These double mutations were assayed for their ability to bind h-Syt II by pull down assay. Mutants that show strong binding to h-Syt II are indicated with an * (FIG. 7B). Proposed mutations for combination that may enhance the affinity between BoNT/B and human Syt II are listed in the table.

FIG. 8A-FIG. 8B show the quantitative measurement of binding affinity between indicated BoNT/B-H$_C$ and h-Syt II. (FIG. 8A) Binding of GST tagged h-Syt II to His-tagged WT BoNT/B-H$_C$ and E1191M/S1199Y was measured by biolayer interferometry assay. Briefly, anti-GST biosensors were loaded with GST-h-Syt II. The loaded biosensors were incubated with 1 μM BoNT/B-H$_C$ proteins for measurement of association kinetics, followed by washing steps to measure dissociation kinetics. Representative association and dissociation curves are shown. (FIG. 8B) Binding affinities between indicated BoNT/B-H$_C$ and Syt II were measured by biolayer interferometry assay as described in panel A. Kinetic parameters ($k_{on}$ and $k_{off}$) and overall binding affinities ($K_D$) were calculated from a non-linear fit of association and dissociation curves. Binding of WT BoNT/B-H$_C$ to h-Syt II is too weak to be reliably determined, with estimated $K_D$ beyond the detection limit (>20 μM), whereas majority of double and triple mutants showed drastically increased binding affinity at the range of 0.59 to 4.30 μM.

FIG. 9A-FIG. 9C show experimental results that indicate selected BoNT/B-H$_C$ mutants have enhanced binding to human Syt I. (FIG. 9A) WT BoNT/B-H$_C$ and E1191M mutant were purified as His6-tagged recombinant proteins ("His6" disclosed as SEQ ID NO: 13) and incubated with immobilized GST-tagged h-Syt I (1-80), with or without the presence of co-receptor gangliosides (Gangl). Binding of WT BoNT/B-H$_C$ to h-Syt I requires the presence of the co-receptor gangliosides, indicating a relatively weak interactions between WT BoNT/B-H$_C$ and h-Syt. The E1191M mutant can bind to h-Syt I without gangliosides, showing improved binding affinity to h-Syt I. (FIG. 9B) Binding of WT and indicated mutant BoNT/B-H$_C$ to h-Syt I were measured by biolayer interferometry as described in FIG. 8A. (FIG. 9C) Kinetic parameters ($k_{on}$ and $k_{off}$) and overall affinities ($K_D$)) for WT BoNT/B-H$_C$, BoNT/B-H$_C$ (E1191M/ S1199Y) ("B H$_C$ MY"), and BoNT/B-H$_C$ (E1191V/S1199Y) ("B H$_C$ VY") to h-Syt I were measured and calculated as described in FIG. 8B. Binding of WT BoNT/B-H$_C$ (B H$_C$ wt) to h-Syt I cannot be reliably determined, with estimated KD over the detection limit (>20 μM). BoNT/B-H$_C$ (E1191M/ S1199Y, B H$_C$, MY) and BoNT/B-H$_C$ (E1191V/S1199Y, B H$_C$ VY) showed drastically increased binding affinity, with $K_D$ at 2.9 μM and 5.82 μM, respectively.

(FIG. 10A) Humanized neurons were created by knocking down endogenous Syt I and expressing full-length h-Syt II in cultured rat cortical neurons. Neurons that express full-length m-Syt II or m-Syt II (F54L) served as additional controls. These neurons were exposed to WT H$_C$B, followed by immunostaining analysis. Bound H$_C$B was detected via a HA tag fused to H$_C$B. Synapsin was labeled as a marker for presynaptic terminals, WT H$_C$B bound to synapses of WT neurons but not Syt I KD neurons. Expression of full-length m-Syt II via lentiviral transduction restored binding of H$_C$B, while expression of full-length m-Syt II (F54L) or full-length h-Syt II failed to rescue the binding. (FIG. 10B) Syt I KD also abolished binding of H$_C$B$_{MY}$ to neurons. The binding was rescued by expression of full length m-Syt II, m-Syt II (F54L), and h-Syt II.

(FIG. 11A) Humanized neurons were created as described in FIG. 11A. These neurons were exposed to a gradient of concentrations of full-length WT BoNT/B or BoNT/B$_{MY}$ for 24 hours. Cell lysates were harvested and subjected to immunoblotting analysis. β-tubulin served as an internal loading control. More VAMP2 was cleaved by BoNT/B$_{MY}$ than WT BoNT/B at the same concentrations, indicating that BoNT/B$_{MY}$ entered neurons more efficiently than WT BoNT/B. Humanized neurons were exposed to a gradient of concentrations of WT BoNT/B or BoNT/B$_{MY}$ for 24 hours and then the mIPSC activity was recorded by whole-cell patch-clamp approach. (FIG. 11B) shows representative mIPSC recordings at 30 pM toxins. (FIG. 11C) depicts the mIPSC activities versus toxin concentrations, normalized to neurons that were not exposed to any toxins. The half maximum inhibitory concentration ($IC_{50}$) is 89 pM for WT BoNT/B and 7.8 pM for BoNT/B$_{MY}$, demonstrating that enhanced binding to human receptors resulted in increased efficacy of toxin at functional levels in neurons.

FIG. 12 is the amino acid sequence of the BoNT/B-Hc (strain 1: BoNT/B1 Okra strain). Residues 857-1291 of BoNT/B, strain 1, GenBank®: AB232927.1. (SEQ ID NO: 2).

FIG. 13 is the nucleic acid sequence encoding BoNT/B-Hc (strain B1, Okra strain) residues 857-1291 of BoNT/B, strain 1, based on GenBank®: AB232927.1), which has been optimized for expression in *E. coli*. (SEQ ID NO: 3)

FIG. 14 shows the amino acid sequence of *C. botulinum* serotype A (1296 a.a.). (SEQ ID NO: 4)

FIG. 15 shows the amino acid sequence of *C. botulinum* serotype B (1291 a.a.). (SEQ ID NO: 5)

FIG. 16 shows the amino acid sequence of *C. botulinum* serotype C1 (1291 a.a.). (SEQ ID NO: 6)

FIG. 17 shows the amino acid sequence of *C. botulinum* serotype D (1276 a.a.). (SEQ ID NO: 7)

FIG. 18 shows the amino acid sequence of *C. botulinum* serotype E (1252 a.a.). (SEQ ID NO: 8)

FIG. 19 shows the amino acid sequence of *C. botulinum* serotype F (1274 a.a.). (SEQ ID NO: 9)

FIG. 20 shows the amino acid sequence of *C. botulinum* serotype G (1297 a.a.). (SEQ ID NO: 10)

FIG. 21 shows the amino acid sequence of *C. botulinum* serotype B, Strain Eklund 17B (BoNT/B4) (SEQ ID NO: 11) Genbank® Ref: EF051570.1.

DETAILED DESCRIPTION OF THE INVENTION

Figures 1B, 1C:
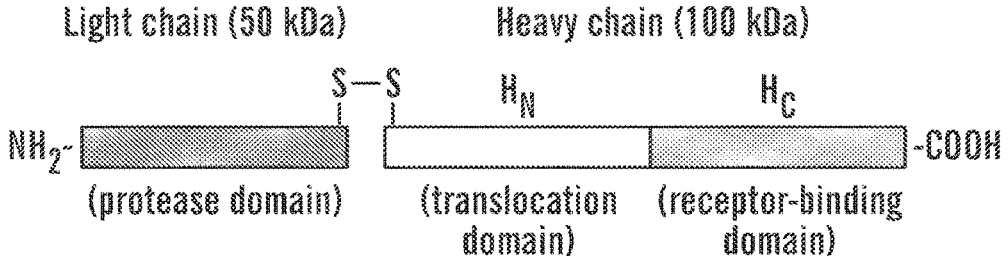
Figure 1D:
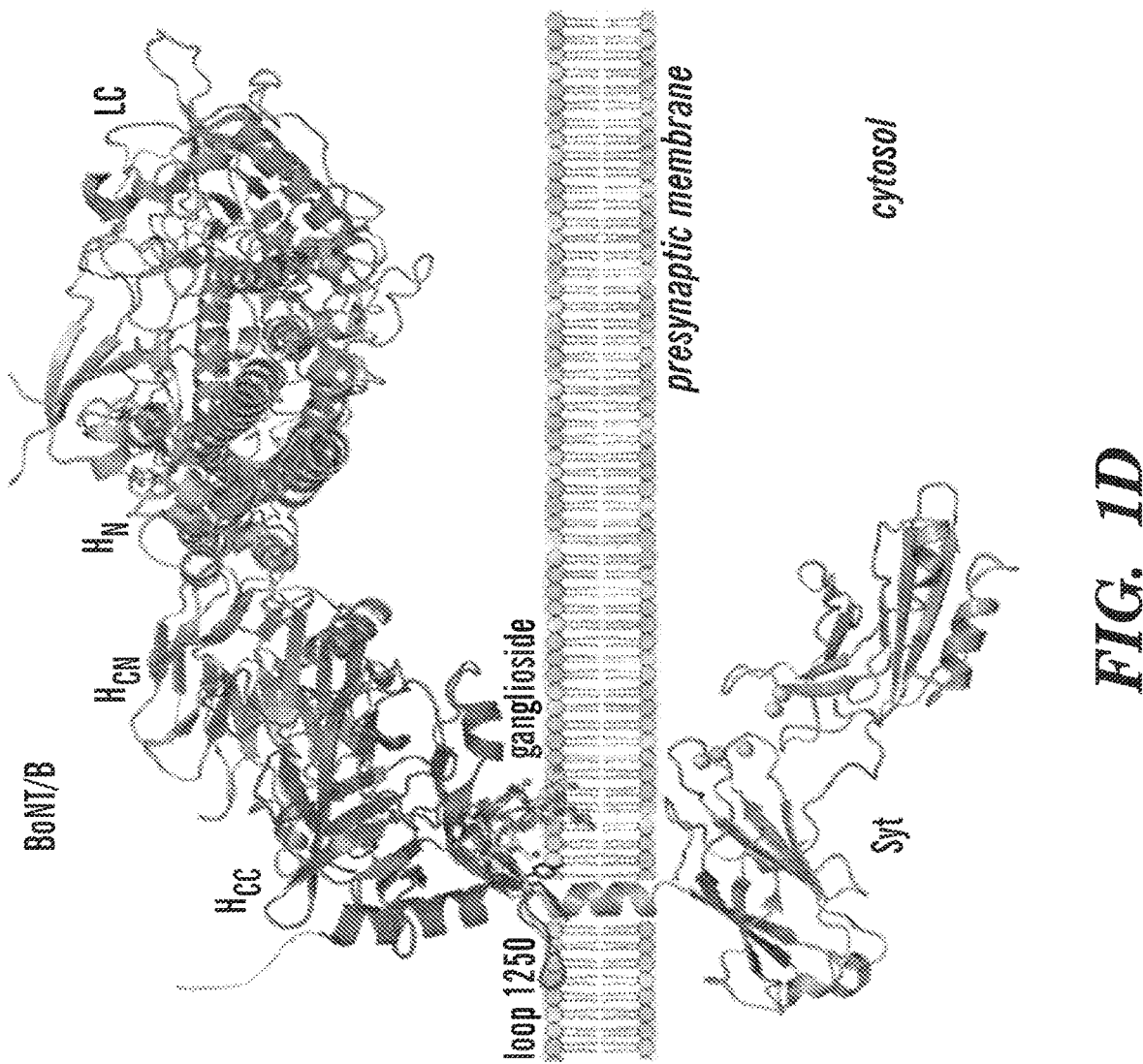
Figures 2A, 2B, 2C, 2D:
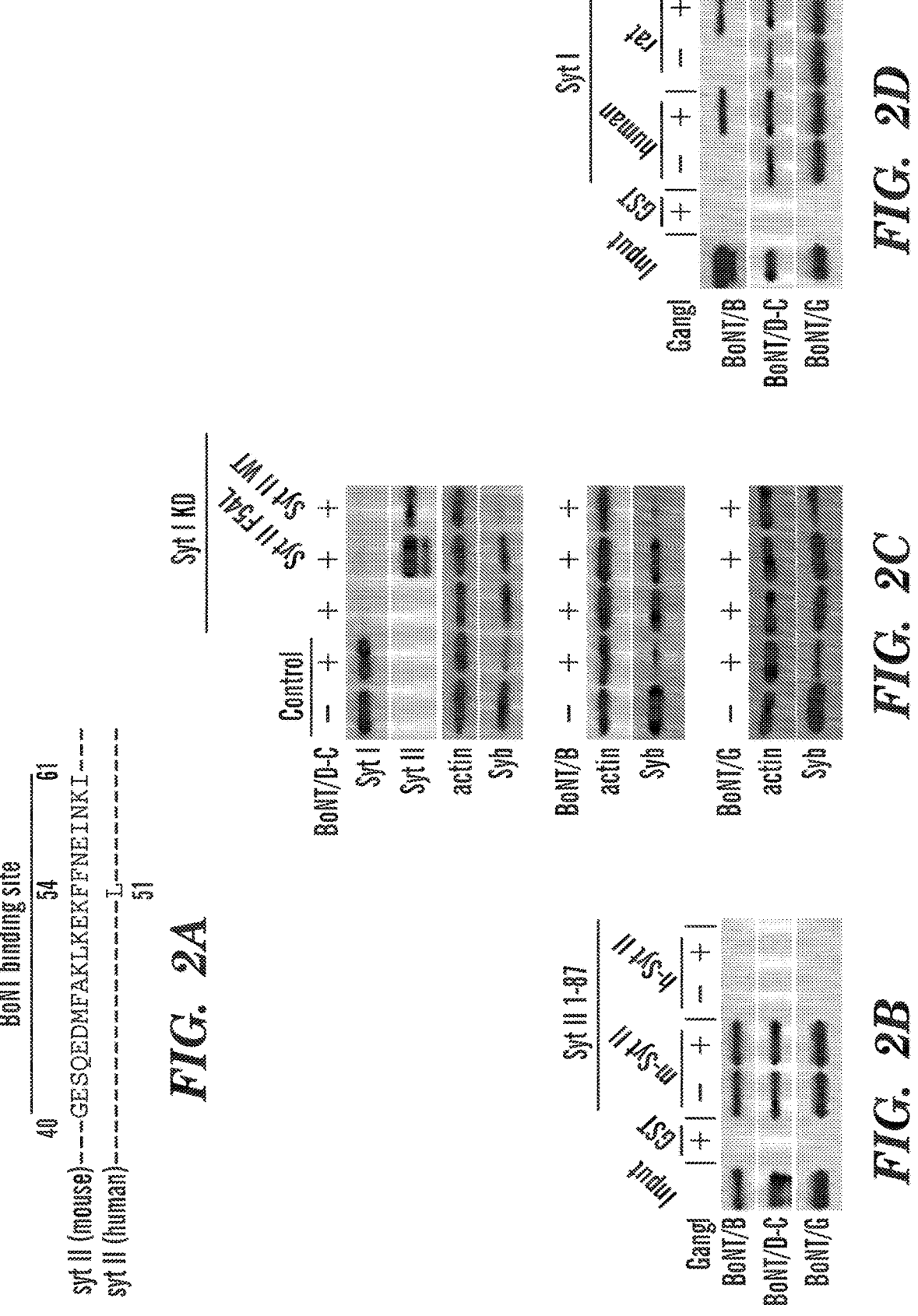
FIG. 2A-FIG. 2D show prior data adapted from published literatures showing indicating that human Syt II is not an effective receptor for BoNT/B, D-C, and G. (A) Human Syt II differs from mouse/rat Syt II by a single residue within the toxin binding site (residue 54 in mouse Syt II, 51 in human Syt II). (SytII (mouse) shown is SEQ ID NO: 1 and Syt II (human) shown is SEQ ID NO: 14).

Aspects of the invention relate to the generation of polypeptides, and nucleic acids encoding the polypeptides, comprising a modified receptor binding domain of *Clostridial botulinum* (e.g., serotype B (B-H$_c$)), and more particularly to *C. botulinum* neurotoxin (BoNT) polypeptide which has improved binding to its human receptors through the incorporation of a modified receptor binding domain, and nucleic acids encoding the polypeptide. From these findings, a new generation of therapeutic BoNTs can be created by utilizing the modified receptor binding domain identified herein, with improved efficacy and specificity to target human neurons than the currently utilized WT BoNTs.

Definitions

As used herein, the term "binding affinity" means how strong a molecule's binding activity is for a particular receptor system. In general, high binding affinity results from greater intermolecular force between a binding domain and its receptor system while low binding affinity involves less intermolecular force between the ligand and its receptor. High binding affinity involves a longer residence time for the binding domain at its receptor binding site than is the case for low binding affinity. As such, a molecule with a high binding affinity means a lower concentration of that molecule is required to maximally occupy the binding sites of a receptor system and trigger a physiological response. Conversely, low binding affinity means a relatively high concentration of a molecule is required before the receptor binding sites of a receptor system is maximally occupied and the maximum physiological response is achieved. Thus, a botulinum neurotoxin of the present invention with increased binding activity due to high binding affinity will allow administration of reduced doses of the toxin, thereby reducing or preventing unwanted side-effects associated with toxin dispersal into non-targeted areas.

One parameter that is often used to measure the binding affinity is defined as binding $K_D$. Because $K_D$ is defined as the ratio between dissociation constant ($K_{off}$) and association constant ($K_{on}$), the lower the $K_D$ value, the higher the binding affinity.

As the term is used herein, "significantly enhanced binding" when used to describe the binding affinity of a *C. botulinum* neurotoxin molecule or BoNT/B-Hc binding fragment thereof, of the present invention to a specific receptor (e.g., human Syt II or human Syt I), refers to an increase in binding affinity for a specific receptor that is substantially increased (e.g., by 10%, 20%, 30%, 40%, 50%, 60%, 70%, 80%, or 90% of the binding affinity of the wild type molecule) as compared to the non-substituted version of the molecule. In one embodiment, the enhanced binding of the substituted molecule is demonstrated by a binding affinity that is an order of magnitude or more than the binding affinity of the non-substituted molecule (e.g., the neurotoxin with a naturally occurring BoNT $H_C$ molecule). Put another way, the $K_D$ of the substituted molecule is an order of magnitude or more lower than the $K_D$ of the non-substituted molecule In one embodiment, the enhanced binding is demonstrated by a binding affinity that is significantly higher (e.g., 1.5×, 2.0×, 2.5×, 3.0×, etc.) than the binding affinity of the non-substituted molecule. Put another way, the $K_D$ of the substituted molecule is significantly lower (e.g., 1.5×, 2.0×, 2.5×, 3.0×, etc.) than the $K_D$ of the non-substituted molecule. In one embodiment, the enhanced binding demonstrated is in the range of about 0.59 µM to 5.82 µM $K_D$. In one embodiment, the enhanced binding demonstrated is in the range of about 0.59 µM to 4.3 µM $K_D$. In one embodiment, the enhanced binding is demonstrated by a $K_D$≤5.82 µM. In one embodiment, the enhanced binding is demonstrated by a $K_D$≤4.30 µM. In one embodiment, the enhanced binding is demonstrated by a $K_D$≤2.9 µM. In one embodiment, the enhanced binding is demonstrated by a $K_D$ of about 0.59 µM.

In one embodiment, the $K_D$ of the substituted molecule for human Syt II is ≤10 µM, preferably ≤9, 8, 7, 6, 5, 4, 3 or 2 µM, more preferably ≤1 or 0.6 µM. In one embodiment, the $K_D$ of the substituted molecule for human Syt I is ≤10 µM, preferably ≤9, 8, 7, 6, 5, 4 µM, more preferably ≤3 µM. In one embodiment, the $K_D$ of the substituted molecule for human Syt II is ≤7 µM and the $K_D$ of the substituted molecule for human Syt I is ≤6 µM. In a preferred embodiment, the $K_D$ of the substituted molecule for human Syt II is ≤1 µM and the $K_D$ of the substituted molecule for human Syt I is ≤3 µM.

In one embodiment, enhanced binding results in detectable binding to human Syt I in the absence of co-receptor gangliosides, such as exemplified by the experiments described herein.

The term "significantly enhanced binding" or "significantly reduced binding" when used to describe the binding affinity of a BoNT/B-$H_C$ binding fragment produced by the point mutations described herein refers to an increase or decrease, respectively, in binding affinity of the modified binding domain (e.g., expressed as an isolated fragment or in the context of the larger polypeptide) to a specific receptor (e.g., human Syt II or human Syt I) as discussed directly above.

As the term is used herein. "significantly reduced binding" when used to describe the binding affinity of botulinum neurotoxin molecule or binding fragment thereof (e.g., BoNT/B-Hc), of the present invention to a specific receptor (e.g., human Syt I or human Syt II), refers to a decrease in binding affinity for the specific receptor that is substantially decreased (e.g., by 10%, 20%, 30%, 40%, 50%, 60%, 70%, 80%, or 90% of the binding affinity of the wild type molecule) as compared to the non-substituted version of the molecule. In one embodiment, the decreased binding of the substituted molecule results in a binding affinity that is an order of magnitude or more less than the binding affinity of the non-substituted neurotoxin (e.g., the neurotoxin with a naturally occurring BoNT $H_C$ molecule). Put another way, the $K_D$ of the substituted molecule is an order of magnitude or more higher than the $K_D$ of the non-substituted neurotoxin. In one embodiment, the reduced binding of the substituted molecule results in a binding affinity that is significantly lower (e.g., 1.5×, 2.0×, 2.5×, 3.0×, etc.) than the binding affinity of the non-substituted molecule. Put another way, the $K_D$ of the substituted molecule is significantly higher (e.g., 1.5×, 2.0×, 2.5×, 3.0×, etc.) than the $K_D$ of the non-substituted molecule. In one embodiment, significantly reduced binding results in loss of detectable binding to human Syt I in the absence of co-receptor gangliosides.

As used herein, the term "botulinum neurotoxin" means any polypeptide that can execute the overall cellular mechanism whereby a (botulinum toxin enters a neuron and inhibits neurotransmitter release. This mechanism encompasses the binding of a *C. botulinum* toxin to a low or high affinity receptor complex, the internalization of the toxin, the translocation of the toxin light chain into the cytoplasm and the enzymatic modification of a *C. botulinum* toxin substrate. The term "polypeptide" and "protein" are used interchangeably herein, in reference to the *C. botulinum* neurotoxin molecule and fragments thereof.

A "modified receptor binding domain" or "modified $H_C$", as the term is used herein, facilitates the binding of the *C. botulinum* neurotoxin molecule in which it is comprised, to a receptor for *C. botulinum* neurotoxin located on the surface of a target cell. Such a molecule is typically generated through genetic recombination technology. The modified $H_C$ has a binding activity for the receptor for *C. botulinum* neurotoxin located on the surface of a target cell. As used herein, the term "binding activity" means that one molecule is directly or indirectly contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. "Bound" and "bind" are considered terms for binding.

As used herein, the term "*C. botulinum* toxin protease domain" means a *C. botulinum* toxin domain that can execute the enzymatic target modification step of the intoxication process. Thus, a *C. botulinum* toxin protease domain specifically targets a *C. botulinum* toxin substrate and encompasses the proteolytic cleavage of a *C. botulinum* toxin substrate, such as, e.g., SNARE proteins like a SNAP-25 substrate, a VAMP substrate and a Syntaxin substrate. Non-limiting examples of *C. botulinum* toxin protease domains are provided in Tables 1 and 2.

As used herein, the term "*C. botulinum* toxin translocation domain" or "$H_N$" means a *C. botulinum* toxin domain that can execute the translocation step of the intoxication process that mediates *C. botulinum* toxin light chain translocation. Thus, a $H_N$ facilitates the movement of a *C. botulinum* toxin light chain across a membrane and encompasses the movement of a *C. botulinum* toxin light chain through the membrane an intracellular vesicle into the cytoplasm of a cell. Non-limiting examples of a $H_N$ include a BoNT/A $H_N$, a BoNT/B $H_N$, a BoNT/C1 $H_N$, a BoNT/D $H_N$, a BoNT/E $H_N$, a BoNT/F $H_N$, and a BoNT/G $H_N$, the amino acid sequences of which are provided in Table 1 and FIGS. 12, 14-20.

As used herein, the term "*C. botulinum* receptor-binding domain" is synonymous with "H$_C$ domain" and means any naturally occurring *C. botulinum* receptor binding domain that can execute the cell binding step of the intoxication process, including, e.g., the binding of the *C. botulinum* toxin to a *C. botulinum* toxin-specific receptor system located on the plasma membrane surface of a target cell. It is envisioned that replacement of the binding activity can be achieved by, e.g., replacing the entire *C. botulinum* H$_C$ domain with a modified (e.g., enhanced) H$_C$ domain.

As used herein, the term "*C. botulinum* toxin target cell" means a cell that is a naturally occurring cell that a naturally occurring *C. botulinum* toxin is capable of intoxicating, including, without limitation, motor neurons; sensory neurons; autonomic neurons; such as, e.g., sympathetic neurons and parasympathetic neurons; non-peptidergic neurons, such as, e.g., cholinergic neurons, adrenergic neurons, noradrenergic neurons, serotonergic neurons, GABAergic neurons; and peptidergic neurons, such as, e.g., Substance P neurons, Calcitonin Gene Related Peptide neurons, vasoactive intestinal peptide neurons, Neuropeptide Y neurons, cholecystokinin neurons.

By "isolated" is meant a material that is free to varying degrees from components which normally accompany it as found in its native state. "Isolate" denotes a degree of separation from original source or surroundings, e.g. from flanking DNA or from the natural source of the DNA, or from flanking amino acids.

The term "purified" is used to refer to a substance such as a polypeptide that is "substantially pure", with respect to other components of a preparation (e.g., other polypeptides). It can refer to a polypeptide that is at least about 50%, 60%, 70%, or 75%, preferably at least about 85%, more preferably at least about 90%, and most preferably at least about 95% pure, with respect to other components. Recast, the terms "substantially pure" or "essentially purified", with regard to a polypeptide, refers to a preparation that contains fewer than about 20%, more preferably fewer than about 15%, 10%, 8%, 7%, most preferably fewer than about 5%, 4%, 3%, 2%, 1%, or less than 1%, of one or more other components (e.g., other polypeptides or cellular components).

The term "conservative" or "conservative substitution mutation" as used herein refers to a mutation where an amino acid is substituted for another amino acid that has similar properties, such that one skilled in the art of peptide chemistry would expect the secondary structure, chemical properties, and/or hydropathic nature of the polypeptide to be substantially unchanged. The following groups of amino acids have been historically substituted for one another as conservative changes: (1) ala, pro, gly, glu, asp, gln, asn, ser, thr; (2) cys, ser, try, thr; (3) val, ile, leu, met, ala, phe; (4) lys, arg, his; and (5) phe, tyr, trp, his. Other commonly accepted conservative substitutions are listed below:

| Residue | Conservative Substitutions |
| --- | --- |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |

-continued

| Residue | Conservative Substitutions |
| --- | --- |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

The term "substitution mutation" without the reference to a specific amino acid, may include any amino acid other than the wild type residue normally found at that position. Such substitutions may be replacement with non-polar (hydrophobic) amino acids, such as glycine, alanine, valine, leucine, isoleucine, methionine, phenylalanine, tryptophan, and proline. Substitutions may be replacement with polar (hydrophilic) amino acids such as serine, threonine, cysteine, tyrosine, asparagine, and glutamine. Substitutions may be replacement with electrically charged amino acids e.g., negatively electrically charged amino acids such as aspartic acid and glutamic acid and positively electrically charged amino acids such as lysine, arginine, and histidine.

The substitution mutations described herein will typically be replacement with a different naturally occurring amino acid residue, but in some cases non-naturally occurring amino acid residues may also be substituted. Non-natural amino acids, as the term is used herein, are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. In some embodiments, the amino acid can be substituted or unsubstituted. The substituted amino acid or substituent can be a halogenated aromatic or aliphatic amino acid, a halogenated aliphatic or aromatic modification on the hydrophobic side chain, or an aliphatic or aromatic modification.

The term "therapeutically effective amount" refers to an amount that is sufficient to effect a therapeutically significant reduction in one or more symptoms of the condition when administered to a typical subject who has the condition. A therapeutically significant reduction in a symptom is, e.g. about 10%, about 20%, about 30%, about 40%, about 50%, about 60%, about 70%, about 80%, about 90%, about 100%, or more as compared to a control or non-treated subject.

The term "treat" or "treatment" refers to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

As used herein, a "subject" refers to a human or animal. Usually the animal is a vertebrate such as a primate, rodent, domestic animal or game animal. Primates include chimpanzees, cynomologous monkeys, spider monkeys, and macaques, e.g., Rhesus, Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms. "patient" and "subject" are used interchangeably herein. A subject can be male or female. A subject can be a fully developed subject (e.g., an adult) or a subject undergoing the developmental process (e.g., a child, infant or fetus).

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted neuronal activity. In addition, the methods and compositions described herein can be used to treat domesticated animals and/or pets.

EMBODIMENTS

The observation that BoNT/B is less specific and potent in humans due to its inability to bind human Syt II, may explain why comparatively higher doses are required than BoNT/A. Higher BoNT/B doses correspond to increased chances for triggering antibody responses and for serious side-effects to occur. Therefore, improved binding of BoNT/B to the human receptor Syt II, to increase its efficacy and specificity to target human neurons should allow a reduced amount of the toxin doses used in therapeutic applications.

Aspects of the invention arise from the finding that modifying the protein sequence of BoNT/B-$H_C$ modifies binding of the fragment containing the receptor binding domain, to the human Syt II receptor. Specific modifications have been identified that enhance binding, thereby generating a domain that binds human Syt II with high-affinity. The modified BoNT/B-$H_C$, when in the context of a full length BoNT protein, retains these binding properties. Incorporation of a modified receptor binding domain with enhanced binding, into a molecule comprising the other BoNT domains, thereby generates a full length BoNT molecule with similarly enhanced receptor binding. As such, new versions of BoNT with high-affinity binding to human Syt II are generated. BoNT with significantly enhanced binding can be used in similar therapies, albeit at lower doses than presently available BoNT molecules, thus providing safer methods of treatment.

The BoNT polypeptides, including full-length BoNT polypeptides and BoNT polypeptide fragments or domains described herein (e.g., the modified BoNT/$H_C$), and nucleic acid molecules which encode them, are explicitly encompassed in the invention. These polypeptides and nucleic acid molecules can be generated by recombinant DNA procedures known in the art. Such polypeptides are typically referred to as "recombinant polypeptides" or "recombinant nucleic acids".

Botulinum Neurotoxin Protein

One aspect of the invention relates to a botulinum neurotoxin (BoNT) protein comprising a modified receptor binding domain (e.g., of *Clostridial botulinum* serotype B), as described herein. The BoNT protein further comprises a protease domain, a translocation domain, and a protease cleavage site. Typically these are arranged in a linear amino-to-carboxyl single polypeptide order of the protease domain, the protease cleavage site, the translocation domain and the modified receptor binding domain. However, different arrangements of the various domains are expected to function adequately. In one embodiment, the modified receptor binding domain comprises one or more substitution mutations which lead to significantly enhanced binding to the human Syt I receptor and/or the human Syt II receptor.

The BoNT protein may further comprise a domain that is useful for purification of the molecule such as a hexahistidine tag (His6) (SEQ ID NO: 13), or an epitope tag such as a hemaglutinin (HA) tag (YPYDVPDYA (SEQ ID NO: 12)). Various such domains are known and used in the art for such purposes.

BoNT has the overall structure shown in FIG. 1B. BoNT is comprised of three domains, each domain having a specific and independent function: a protease domain (also referred to as the light chain), a translocation domain ($H_N$), and a receptor-binding domain ($H_C$). Domains of the various strains of *C. botulinum* neurotoxin have been shown to be largely interchangeable (as demonstrated by naturally occurred chimeric toxins such as BoNT/CD, which is composed of the light chain and $H_N$ of BoNT/C, with the $H_C$ of BoNT/D[34], in U.S. Pat. No. 8,052,979, incorporated herein by reference). The protein can be in single chain form or di-chain form. The di-chain form results from the naturally occurring protease processing of a protease cleavage site located between the protease domain and the translocation domain. The protein is maintained in the di-chain form following protease processing by the presence of a di-sulfide bond.

Strains of Clostridia botulinum produce seven antigenically-distinct types of botulinum toxins, which have been identified by investigating botulism outbreaks in man (BoNT/A, /B, /E and /F), animals (BoNT/C1 and/D), or isolated from soil (BoNT/G). While all seven BoNT serotypes have similar structure and pharmacological properties, each also displays heterogeneous bacteriological characteristics. The genetic diversity of the *C. botulinum* strains is described in detail in Hill et al. (Journal of Bacteriology, Vol. 189, No. 3, p. 818-832 (2007)) 35, the contents of which are incorporated herein by reference. In one embodiment, the BoNT of the invention has domains which are all of the same serotype (A, B, C, D, E, F or G). In one embodiment, one or more of those domains of the same serotype differ as to their strain and/or subtype.

Toxins from the various *C. botulinum* serotypes/strains share the same functional domain organization and overall structural architecture. *C. botulinum* toxins are each translated as a single chain polypeptide of approximately 150 kDa that is subsequently cleaved by proteolytic scission within a disulfide loop by a naturally-occurring protease, such as, e.g., an endogenous *C. botulinum* toxin protease or a naturally-occurring proteases produced in the environment. This posttranslational processing yields a di-chain molecule comprising an approximately 50 kDa light chain (LC) and an approximately 100 kDa heavy chain (HC) held together by a single disulfide bond and noncovalent interactions. Each mature di-chain molecule comprises three functionally distinct domains: 1) a proteolytic domain located in the LC that includes a metalloprotease region containing a zinc-dependent endopeptidase activity which specifically targets core components of the neurotransmitter release apparatus: 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC that determines the binding activity and binding specificity of the toxin to the receptor complex located at the surface of the target cell. The locations of the specific domains within the toxin of various serotypes/strains are provided in Table 1:

TABLE 1

| C. botulinum toxin domains from various serotypes/strains | | | |
|---|---|---|---|
| Toxin | LC | $H_N$ | $H_C$ |
| BoNT/A | M1-K448 | A449-K871 | N872-L1296 |
| BoNT/B | M1-K441 | A442-S858 | E859-E1291 |
| BoNT/C1 | M1-K449 | T450-N866 | N867-E1291 |
| BoNT/D | M1-R445 | D446-N862 | S863-E1276 |
| BoNT/E | M1-R422 | K423-K845 | R846-K1252 |
| BoNT/F | M1-K439 | A440-K864 | K865-E1274 |
| BoNT/G | M1-K446 | S447-S863 | N864-E1297 |

Complete amino acid sequences of the toxins are provided in FIGS. 14-21.

The binding, translocation and protease activity of these three functional domains are all necessary for toxicity. The overall cellular intoxication mechanism whereby *C. botulinum* toxins enter a neuron and inhibit neurotransmitter release is similar, regardless of serotype or subtype. Without wishing to be bound by theory, the intoxication mechanism involves at least four steps: 1) receptor binding, 2) complex internalization, 3) light chain translocation, and 4) protease target modification. The process is initiated when the $H_C$ domain of a *C. botulinum* toxin binds to a toxin-specific receptor located on the plasma membrane surface of a target cell. The binding specificity of a receptor complex is thought to be achieved, in part, by specific combinations of gangliosides and protein receptors. Once bound, the toxin/receptor complexes are internalized by endocytosis and the internalized vesicles are sorted to specific intracellular routes. The translocation step is triggered by the acidification of the vesicle compartment. Once translocated, light chain endopeptidase of the toxin is released from the intracellular vesicle into the cytosol where it specifically targets one of three proteins known as the core components of the neurotransmitter release apparatus (vesicle-associated membrane protein (VAMP)/synaptobrevin, synaptosomal-associated protein of 25 kDa (SNAP-25) and Syntaxin). These core components are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic plasma membrane surface. The selective proteolysis of synaptic SNAREs accounts for the block of neurotransmitter release caused by *C. botulinum* toxins in vivo. The SNARE protein targets of *C. botulinum* toxins are common to exocytosis in a variety of nonneuronal types: in these cells, as in neurons, light chain peptidase activity inhibits exocytosis, see, e.g., Yann Humeau et al., How Botulinum and Tetanus Neurotoxins Block Neurotransmitter Release, 82 (5) Biochimie. 427-446 (2000); Kathryn Turton et al., Botulinum and Tetanus Neurotoxins: Structure, Function and Therapeutic Utility, 27 (11) Trends Biochem. Sci. 552-558. (2002); Giovanna Lalli et al., The Journey of Tetanus and Botulinum Neurotoxins in Neurons, 11 (9) Trends Microbiol. 431-437. (2003).

Domains and Chimeric Neurotoxins

The botulinum neurotoxin of the present invention comprises a modified receptor binding domain ($H_C$). The modified receptor binding domain exhibits significantly enhanced binding to one or more human receptors typically bound and utilized by one or more *C. botulinum* toxin strains (e.g., SytII, SytI). The modified receptor binding domain can be of any serotype (A, B, C, D, E, F or G), strain or subtype (as described herein). This may be the same or different serotype, strain/subtype as one or more other domains within the BoNT. Examples of specific modified receptor binding domains are provided herein. The isolated modified receptor binding domain polypeptide described herein is also encompassed by the present invention, as is the isolated nucleic acid molecule by which it is encoded. In one embodiment, the $H_C$ is serotype B. In one embodiment, the $H_C$ is serotype A.

The botulinum neurotoxin of the present invention also comprises a protease domain, also referred to in the art as a light chain variant. The light chain variant may be a naturally occurring light chain variant, such as, e.g., *C. botulinum* toxin light chain isoforms and *C. botulinum* toxin light chain subtypes: or a non-naturally occurring *C. botulinum* toxin light chain variant, such as, e.g., conservative substitution *C. botulinum* toxin light chain variants. The protease domain can be of any serotype (A, B, C, D, E, F or G), strain or subtype (as described herein). This may be the same or different serotype, strain/subtype as one or more other domains within the BoNT. In one embodiment, the protease domain is serotype B. In one embodiment, the protease domain is serotype A.

The botulinum neurotoxin of the present invention also comprises a toxin translocation domain ($H_N$). The toxin translocation domain can be of any serotype (A, B, C, D, E, F or G), strain or subtype (as described herein). This may be the same or different serotype, strain/subtype as one or more other domains within the BoNT. In one embodiment, the $H_N$ is serotype B. In one embodiment, the $H_N$ is serotype A.

The various domains described herein (e.g., $H_N$, $H_C$, or protease domain) include, without limitation, naturally occurring variants, such as, e.g., isoforms and subtypes; non-naturally occurring variants, such as, e.g., conservative substitution mutations. Non-naturally-occurring variants, refers to a domain that has at least one amino acid change from the corresponding region of the reference sequences (e.g., from Table 1 or FIGS. 14, 16-23) and can be described in percent identity to the corresponding region of that reference sequence.

It is recognized by those of skill in the art that within each serotype of *C. botulinum* toxin there can be naturally occurring *C. botulinum* domain variants that differ somewhat in their amino acid sequence, and also in the nucleic acids encoding these proteins. A naturally occurring *C. botulinum* toxin domain (e.g., light chain, $H_N$ or $H_C$) variant envisioned for use in the generation of the BoNT of the present invention can function in substantially the same manner as the reference *C. botulinum* toxin domain on which the naturally occurring *C. botulinum* botulinum domain variant is based, and can be substituted for the reference *C. botulinum* toxin domain in any aspect of the present invention.

A non-limiting example of a naturally occurring *C. botulinum* toxin domain variant is a *C. botulinum* toxin domain isoform such as, e.g., a BoNT/A domain isoform, a BoNT/B domain isoform, a BoNT/C1 domain isoform, a BoNT/D domain isoform, a BoNT/E domain isoform, a BoNT/F domain isoform, and a BoNT/G domain isoform. A (botulinum toxin domain isoform can function in substantially the same manner as the reference *C. botulinum* toxin domain on which the *C. botulinum* toxin domain isoform is based, and can be substituted for the reference *C. botulinum* toxin domain in any aspect of the present invention.

Another non-limiting example of a naturally occurring *C. botulinum* toxin domain variant is a *C. botulinum* toxin domain subtype such as, e.g., a domain from subtype BoNT/A1, BoNT/A2, BoNT/A3, BoNT/A4, BoNT/A5; a domain from subtype BoNT/B1. BoNT/B2, BoNT/B3, BoNT/B4, BoNT/B5, BoNT/B6, BoNT/B7; a domain from subtype BoNT/C1-1, BoNT/C1-2, BoNT/D-C; a domain from subtype BoNT/E1, BoNT/E2, BoNT/E3, BoNT/E4, BoNT/E5, BoNT/E6, BoNT/E7, BoNT/E8; and a domain from subtype BoNT/F1, BoNT/F2, BoNT/F3, BoNT/F4, BoNT/F5, BoNT/F6, BoNT/F7. A *C. botulinum* toxin domain subtype can function in substantially the same manner as the reference *C. botulinum* toxin domain on which the *C. botulinum* toxin domain subtype is based, and can be substituted for the reference *C. botulinum* toxin domain in any aspect of the present invention.

As used herein, the term "non-naturally occurring variant" (e.g., *C. botulinum* toxin light chain variant, $H_C$ and $H_N$) means a *C. botulinum* domain produced with the aid of human manipulation, including, without limitation, domains produced by genetic engineering using random mutagenesis or rational design and *C. botulinum* domains produced by chemical synthesis. Non-limiting examples of non-naturally occurring *C. botulinum* domain variants include, e.g., conservative *C. botulinum* domain variants. As used herein, the term "conservative *C. botulinum* domain variant" means a *C. botulinum* domain that has at least one amino acid substituted by another amino acid or an amino acid analog that has at least one property similar to that of the original amino acid from the reference *C. botulinum* domain sequence (e.g., Table 1 and FIGS. 12, 14-21). The variant may have one, two, three, four, five or more conservative amino acid substitutions compared to the reference domain sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative *C. botulinum* domain variant can function in substantially the same manner as the reference *C. botulinum* toxin domain on which the conservative *C. botulinum* toxin domain variant is based, and can be substituted for the reference *C. botulinum* domain in any aspect of the present invention.

A non-naturally occurring *C. botulinum* toxin domain variant may substitute one or more amino acids (e.g., 1, 2, 3, 4, 5, 6, 7, 8, 9, or more) from the reference *C. botulinum* toxin domain on which the naturally occurring *C. botulinum* toxin domain is based. A non-naturally occurring *C. botulinum* toxin domain variant can also possess 95% or more (e.g., 96%, 97%, 98% or 99%) amino acid identity to the reference *C. botulinum* toxin domain on which the naturally occurring *C. botulinum* domain variant is based.

Various non-naturally occurring *C. botulinum* neurotoxins or specific domains thereof, are described in International Patent Publications WO95/32738, WO96/33273, WO98/07864 and WO99/17806, each of which is incorporated herein by reference. The *C. botulinum* neurotoxin or specific domain thereof described herein will typically contain naturally occurring amino acid residues, but in some cases non-naturally occurring amino acid residues may also be present. Therefore, so-called "peptide mimetics" and "peptide analogues", which may include non-amino acid chemical structures that mimic the structure of a particular amino acid or peptide, may also be used within the context of the invention. Such mimetics or analogues are characterized generally as exhibiting similar physical characteristics such as size, charge or hydrophobicity, and the appropriate spatial orientation that is found in their natural peptide counterparts. A specific example of a peptide mimetic compound is a compound in which the amide bond between one or more of the amino acids is replaced by, for example, a carbon-carbon bond or other non-amide bond, as is well known in the art (see, for example Sawyer, in Peptide Based Drug Design, pp. 378-422, ACS, Washington D.C. 1995).

In one aspect of the invention, the botulinum neurotoxin (BoNT) of the present invention comprises a modified receptor binding domain of *C. botulinum* serotype B (BoNT/B-$H_C$). The modified BoNT/B-$H_C$ comprises one or more substitution mutations which lead to significantly enhanced binding to the human Syt I receptor and/or the human Syt II receptor. In one embodiment, the BoNT/B-$H_c$ is from BoNT/B1 (GenBank®; access No.: AB232927.1). The amino acid sequence of BoNT/B1-$H_C$ Okra strain, used as the reference template in the present invention is shown in FIG. 12. The generation of B-$H_c$ from other strains and subtypes by substitution of the amino acids that correspond to the specified position(s) in B1 described herein is also envisioned, as is the generation of longer molecules that incorporate the B-$H_c$ such as complete BoNT or a polypeptide comprising the modified B-$H_c$. Such molecules are also encompassed in the invention. In one embodiment, the BoNT or the polypeptide of the present invention comprises a modified receptor binding domain which is not a BoNT/B4 strain known as the Eklund strain (NCBI® Reference Sequence: YP_001893661.1, Genbank® Ref: EF051570.1), shown in FIG. 21. In one embodiment, the modified B-Hc is not of strain 3, 7 or 8.

Toxin diffusion and generation of neutralization antibodies is a problem associated with but not limited to BoNT/B, as they are also observed with BoNT/A. Improvement of the binding affinity of BoNT/A to its receptor SV2 would relieve these problems. Because BoNT/B binding to Syt I/II has much higher affinity than BoNT/A binding to SV2[14,20,26,27], a modified BoNT/B receptor binding domain (BoNT/B-$H_C$) with the ability to bind human Syt II can also be used to replace BoNT/A-$H_C$ to generate a modified chimeric BoNT/A which may have greater efficacy and specificity for human neurons than WT BoNT/A.[28 29 30]

It is further envisioned that the modified $H_C$ described above (e.g., BoNT/B-$H_C$) can be utilized to replace the $H_C$ of all other BoNT serotypes/strains. As such, another aspect of the invention is a BoNT polypeptide comprising a modified receptor biding domain ($H_C$) of serotype (A, B, C, D, E, F or G), joined with one or more domains of a different serotype (A, B, C, D, E, F or G), strain or subtype to thereby produce a chimeric neurotoxin. The $H_C$ region of each BoNTs is well defined and respective $H_C$ regions can be exchanged in the BoNT molecule (e.g., via genetic engineering). Such manipulation is routinely performed by the skilled practitioner via standard PCR fusion of DNA encoding BoNT/B-$H_C$ with the light chain (LC) and translocation domain ($H_N$), or $H_N$-LC, of other BoNTs, which has been well-established in the art. In addition, the replacement may also be performed using the C-terminal part of BoNT/B-$H_C$ (designated as $H_{CC}$), which is the region containing the binding site for protein receptors and gangliosides in each BoNT. The resulting chimeric toxins will have the ability to target human neurons via binding to human Syt I/II. As a non-limiting example, modified BoNT/B-$H_C$ (or BoNT/B-$H_{CC}$) can be used to replace the $H_C$ (or $H_{CC}$) of BoNT/A. The resulting polypeptides are encompassed by the instant invention. These chimeric toxins may have a higher efficacy and specificity targeting human neurons than WT BoNT/A. Such a chimeric BoNT/A toxin can be used for therapeutic applications in humans and offers significant improvements over WT BoNT/A.

One aspect of the invention relates to an isolated, purified modified receptor binding domain polypeptide as described herein. In one embodiment, the modified receptor binding domain is BoNT/B-$H_C$ (e.g., from BoNT/B1). In one embodiment, the B-$H_c$ is generated from a different strain and/or subtype of BoNT by substitution of the amino acids that correspond to the specified position(s) in B1 described herein. In one embodiment, the $H_C$ is subtype B2, B3, B4, B5, B6 or B7. In one embodiment, the modified receptor binding domain is not from BoNT/B4 (the Eklund strain). In one embodiment, the modified B-Hc is not of strain 3, 7 or 8.

The present invention encompasses mutant full-length BoNT that contains a modified $H_C$ (e.g., B-$H_C$) with amino acid substitutions as described herein, for therapeutic applications in humans. In one embodiment, the full-length BoNT contains a modified $H_C$ (e.g., B-$H_C$) with an amino acid substitution at one or combinations of the amino acid residues corresponding to position E1191, S1199, Y1183, and W1178 of B1 (e.g., selected from those listed in Table 2). In one embodiment, the BoNT contains a modified $H_C$ (e.g., B-$H_C$) with a single amino acid substitution as described herein. In one embodiment, the BoNT contains a modified $H_C$ (e.g., B-$H_C$) with two amino acid substitutions as described herein. In one embodiment, the BoNT contains a modified $H_C$ (e.g., B-$H_C$) with three amino acid substitutions as described herein. The mutations can be made in the same manner as disclosed herein for BoNT/$H_C$, (e.g., using any one of BoNT/B subtypes or any serotype as template). In one embodiment, the mutant full-length BoNT contains a modified Hc that is not from BoNT/B4 (the Eklund strain). In one embodiment, the modified B-Hc is not of strain 3, 7 or 8.

The resulting BoNT toxin can have significantly enhanced binding to human Syt II, and therefore will achieve higher efficacy and specificity to target human neurons than WT BoNT. The resulting mutant may further maintain similar binding to human SytI, have significantly enhanced binding to human SytI, or have significantly reduced binding to human SytI.

Polypeptides and Chimeric Polypeptides

Another aspect of the invention relates to a polypeptide comprising the modified receptor binding domain (e.g., of serotype A, B, C, D, E, F or G). In one embodiment, the modified Hc, in the context of the polypeptide, has significantly enhanced binding to human Syt II and/or Syt I, as compared to the analogous polypeptide with WT amino acids at the specific positions modified in the Hc (the wild type counterpart). In one embodiment, the modified receptor binding domain is BoNT/B-$H_C$ (e.g., from BoNT/B1). In one embodiment, the modified $H_c$ is generated from a different serotype, strain and/or subtype of BoNT by substitution of the amino acids that correspond to the specified position(s) in B1 described herein. In one embodiment, the modified Hc is not from BoNT/B4 (the Eklund strain). In one embodiment, the modified B-Hc is not of strain 3, 7 or 8. In one embodiment, the modified receptor binding domain has one or more modifications (amino acid substitutions) in the C-terminal part of BoNT/B-$H_C$ (designated as $H_{CC}$), which is the region containing the binding site for protein receptors and gangliosides in each BoNT. In one embodiment, the resulting polypeptide has the ability to target human neurons via binding to human SytI/II.

The polypeptide comprising the modified receptor binding domain may be a fusion protein of the receptor binding domain and another functional polypeptide (e.g., a functional polypeptide utilized in a 2-hybrid system (bait or prey such as T18 or T25, or glutathione S transferase (GST)). This can also be referred to as a chimeric polypeptide molecule. Alternatively, it may be a fusion of the modified receptor binding domain and a polypeptide tag for identification purposes and/or purification purposes (e.g., a hexa-histidine tag (His6) (SEQ ID NO: 13), or an epitope tag such as a hemaglutinin (HA) tag (YPYDVPDYA (SEQ ID NO: 12)), or GST), many of which are known and commonly used in the art. The fusion may have a stretch of amino acids between the respective functional domains that facilitates linkage, serves as a cleavage site, or to preserve independent conformation and/or function. In one embodiment, the linkage preserves the function of the modified receptor binding domain. In one embodiment, the linkage masks the function of the modified receptor binding domain. Another aspect of the invention relates to a nucleic acid molecule which encodes any one of such polypeptides.

The modified BoNT/$H_C$ (e.g., B-$H_C$) can be linked to other agents (e.g., proteins, small molecules, short polypeptides, nucleic acids) covalently (e.g., as a fusion protein) or non-covalently. As such, another aspect of the invention relates to a chimeric molecule comprising a first portion that is a modified receptor binding domain of *C. botulinum* (e.g., serotype B), as described herein, linked to a second portion. The second portion of the molecule can be a bioactive (or "biologically active") molecule such as a therapeutic agent (e.g., a polypeptide or non-polypeptide drug such as a small molecule or nucleic acid). Linkage of the first and second portions of the molecule can be covalent (e.g., in the form of a fusion protein) or non-covalent. Methods of such linkage are known in the art and can readily be applied by the skilled practitioner. One such use of a chimeric molecule of the invention is as a delivery tool to target neurons in humans. For example, the modified BoNT/$H_C$ can be linked to other therapeutic agents, to serve as the targeting vehicle to deliver the therapeutic agents to neurons in humans by binding to human Syt I and/or Syt II.

Modifications of the Receptor Binding Domain (Hc)

As discussed herein, the invention relates to a modified Hc and polypeptides comprising the modified Hc (e.g., BoNT or a fusion or chimeric polypeptide). The modification of the $H_C$ amino acid sequence used to generate these various polypeptides of the invention can be performed by various methods known to the skilled practitioner. Examples include, without limitation, targeted mutagenesis (site-directed mutagenesis) or random mutagenesis of each amino acid residue within the region known for binding Syt I/II. These Syt binding regions are well defined by previous studies relating to mouse or rat Syt receptors[1,29,36,31,32] but have not been clearly determined for interactions between BoNT/B-$H_c$ and human Syt receptors. Different subtypes of BoNT/B, or other serotypes which bind to Syt I/II (D-C or G), can be used as the template to create the same or similar mutations by generating corresponding mutations described herein for B1-$H_C$. The corresponding position for selected residues to be mutated can be readily identified by sequence alignment with the B1 subtype. The resulting polypeptide products are encompasses by the instant invention, as are polypeptides comprising said products and nucleic acid molecules encoding said polypeptides and products.

Amino acid sequence modifications of $H_C$ to produce the modified receptor binding domain can be mutation of a single residue to a different amino acid (single site substitution), mutation of multiple residues at the same time (multiple sites substitution), deletion of one or more residues (deletion), and insertion of one or more residues (insertion), as well as combinations thereof. Methods for mutating proteins are well-known in the art (e.g., targeted single site and multiple sites substitutions on the DNA encoding the BoNT/$H_C$ sequence).

In one embodiment, one or more residues in $H_C$ that either contact rodent Syt II or the surrounding regions, based on previous literatures on BoNT/B receptor binding domain[29] and reported BoNT/B-Syt II structure (PDB ID: 2NM1)[31,32], are modified. These include, without limitation those positions that correspond to position Y1181, P1197, A1196, F1204, F1194, P1117, W1178, Y1183, V1118, S1116, K1113, K1192, S1199, S1201, E1191, E1245, Y1256, D1115, E1203 of BoNT/B-B1. In one embodiment, one or more of these residues is systemically replaced with other amino acids. Combinations of various modifications are also envisioned, including, without limitation, mutations of two or more recited positions, to any variety of amino acids, such as those recited herein.

Multiple site substitutions (e.g., 2 or 3) can be generated by combining mutations in these identified key residues. Such multiple site substitution mutants may have even further enhanced binding to h-Syt II and may further maintain or have enhanced binding to human Syt I. In one embodiment, the modified $H_C$ has a first amino acid substitution that corresponds to E1191 of serotype B, strain 1, substituted with either Q, M, C, V, L, or Y. In one embodiment, the modified $H_C$ has a second site substitution that corresponds to either S1199W, S1199E, S1199H, S1199Y, W1178Y, W1178Q, W1178A, W1178S, Y1183C, Y1183P, S1199F or S1199L of serotype B, strain 1. In one embodiment, the modified $H_C$ has a multiple site substitution that corresponds to either E1191M and S1199W, E1191M and W1178Q, E1191C and S1199W, E1191C and S1199Y, E1191C and W1178Q, E1191Q and S1199W, E1191V and S1199W, E1191V and S1199Y, or E1191V and W1178Q, of serotype B, strain 1.

In one embodiment, the modified receptor binding domain comprises a substitution mutation at a position corresponding to Y1181, P1197, A1196, F1204, F1194, P1117, W1178, Y1183, V1118, S1116, K1113, K1192, S1199, S1201, E1191, E1245, D1115, E1203 or Y1256 of serotype B, strain 1. In one embodiment, the substitution mutation is A, R, N, D, C, Q, E, G, H, I, L, K, M, F, P, T, W, Y or V substituted for S. In one embodiment, the position corresponds to S1199 or S1201 of serotype B, strain 1. In one embodiment, the substitution mutation is W, E or H. In one embodiment, the substitution mutation is at S1199, and is W, E or H. In one embodiment, the substitution mutation is at S1201 and is V. In one embodiment, the positions corresponds to W1178, Y1183, or E1191. In one embodiment, the position corresponds to W1178 and the substitution mutation is Y, Q, A or S. In one embodiment, the position correspond to Y1183 and the substitution mutation is C or P. In one embodiment, the position corresponds to E1191 and the substitution mutation is C, V, L, or Y.

A modified $H_C$ with a single amino acid substitution mutation shown below in Table 2 is also environed, as is its incorporation in the various polypeptides described herein.

TABLE 2

| E1191M | Y1183C | S1199E | | |
|--------|--------|--------|--------|--------|
| E1191Q | Y1183P | S1199H | | |
| E1191C | Y1183M | S1199Y | P1117S | A1196Y |
| E1191V | | S1199W | P1117M | |
| E1191L | W1178Q | S1199F | P1117Y | Y1181M |
| E1191Y | W1178Y | S1199L | | |
| E1191T | W1178A | | V1118M | |
| E1191I | W1178S | S1201V | | |

Figure 3A:
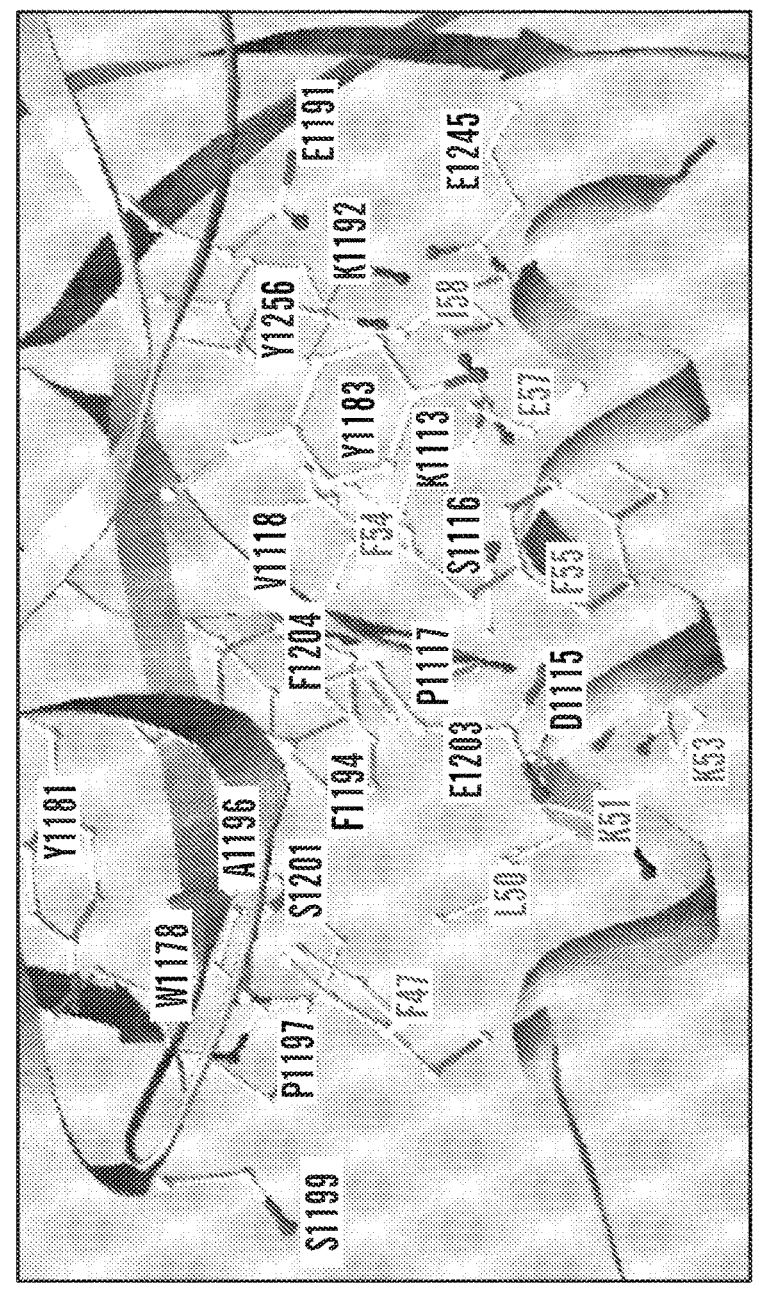

In one embodiment, the $H_C$ comprises one or more mutations that correspond to E1191C/V/L/Y (E1191C, E1191V, E1191L, or E1191Y), S1199W/E/H (S1199W, S1199E, or S1199H), W1178Y/Q/A/S (W1178Y, W1178Q, W1178A, or W1178S), and/or Y1183C/P (Y1183C or Y1183P) of serotype B, strain 1 (FIGS. 3A, B).

Figure 4A:
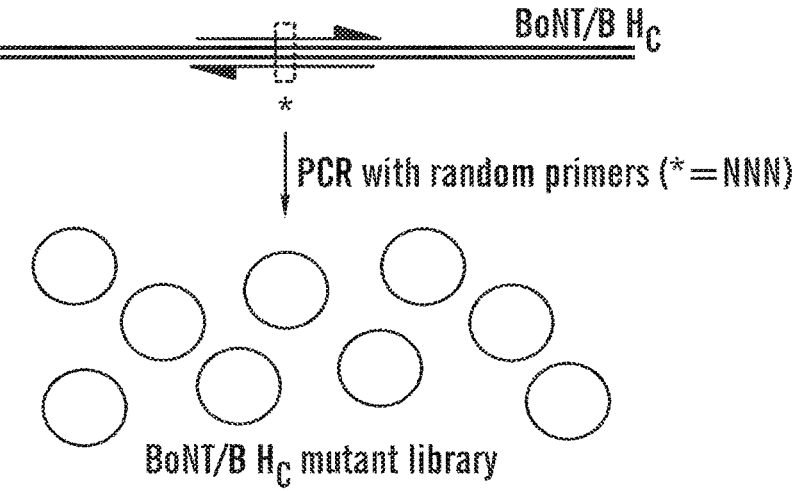
FIG. 4A-FIG. 4B are illustrations of the bacterial adenylate cyclase two hybrids (BACTH) system that is used to screen BoNT/B-H$_C$ mutants for their ability to bind human Syt II.

In one embodiment, the $H_C$ has two substitution mutations wherein one is a substitution mutation corresponding to position 1191 selected from Table 2. In one embodiment, the $H_C$ has enhanced binding to h-Syt II compared to the analogous polypeptide having WT amino acids at the specified positions (also referred to herein as the wild type counterpart). In one embodiment, the generated mutant also maintains or has significantly enhanced binding to human Syt I as compared to the wild type counterpart. In particular, the mutation is E1191C, E1191V, E1191L, or E1191Y. More particularly, the mutation that corresponds to position E1191C, E1191V, E1191L, or E1191Y is combined with a second mutation (e.g., such as those described herein) to generate a modified $H_C$ that has enhanced binding to h-Syt II compared to the analogous polypeptide having WT amino acids at the specified positions (also referred to herein as the wild type counterpart). In one embodiment, the generated mutant also maintains or has significantly enhanced binding to human Syt I as compared to the wild type counterpart (FIG. 4A). In one embodiment, the second mutation is a substitution mutation corresponding to a substitution shown for position 1183, 1199, 1201, 1178, 1117, or 1181 in Table 2. In one embodiment, the second mutation is S1199W, S1199E, S1199H, S1199Y, W1178Y, W1178Q, W1178A, W1178S, Y1183C, Y1183P, S1199F or S1199L. In one embodiment the $H_C$ has two substitution mutations that correspond to those shown for serotype B, strain 1, in Table 3:

TABLE 3

| E1191M and S1199Y | E1191Q and S1199Y | E1191C and S1199Y |
|-------------------|-------------------|-------------------|
| E1191M and S1199W | E1191Q and S1199W | E1191C and S1199W |
| E1191M and S1199L | E1191Q and S1199L | E1191V and S1199Y |
| E1191M and S1199Y | E1191Q and S1199Y | E1191V and S1199W |
| E1191M and S1199F | E1191Q and S1199F | E1191M and W1178Q |
| | | E1191Q and W1178Q |
| | | E1191C and W1178Q |
| | | E1191V and W1178Q |

In one embodiment, the $H_C$ has three substitution mutations, also referred to herein as a triple mutation. In one embodiment of the triple mutation, the first mutation corresponds to E1191Q, E1191M, E1191C, E1191V, E1191L, E1191Y, S1199W, S1199E, S1199H, S1199Y, S1199F, S1199L, Y1183C, Y1183P, W1178Y, W1178Q, W1178A or W1178S of serotype B, strain 1. In one embodiment, the second mutation corresponds to E1191Q, E1191M, E1191C, E1191V, E1191L, E1191Y, S1199W, S1199E, S1199H, S1199Y, S1199F, S1199L, Y1183C, Y1183P, W1178Y, W1178Q, W1178A or W1178S of serotype B, strain 1 (exclusive of the position serving as the first mutation). In one embodiment, the third substitution corresponds to E1191Q, E1191M, E1191C, E1191V, E1191L, E1191Y, S1199W, S1199E, S1199H, S1199Y, S1199F, S1199L, Y1183C, Y1183P, W1178Y, W1178Q, W1178A or W1178S of serotype B, strain 1 (exclusive of the positions serving as the first and second mutations). In one embodiment of the invention, the double or triple mutation does not contain a Q substituted at both positions corresponding to E1191 and W1178.

In one embodiment of the triple mutation, one mutation is a substitution mutation that corresponds to a substitution shown for E1191 in Table 2 (e.g., E1191Q/M/C/V/L or Y). The second mutation may be a substitution mutation corresponding to a substitution shown for S1199 in Table 2 (e.g., S1199W/E/H/Y/F or L). The third mutation may be a substitution mutation corresponding to a substitution shown for W1178 in Table 2 (e.g., W1178Y/Q/A or S). Alternatively, the third mutation may be a substitution mutation corresponding to a substitution shown for Y1183 in Table 2. (e.g., Y1183C, Y1183P). In one embodiment, the triple mutation corresponds to E1191M/S1199W/W1178Q.

Nucleic Acid Molecules

Another aspect of the invention relates to an isolated nucleic acid molecule comprising a nucleotide sequence that encodes the polypeptides described herein (e.g., modified receptor binding domain, or a polypeptide comprising the modified receptor binding domain, or the botulinum neurotoxin comprising the modified receptor binding domain, described herein). In one embodiment, the nucleic acid molecule comprises the nucleic acid sequence shown in FIG. 13. Such nucleic acid molecules can be produced by the skilled practitioner, for example by recombinant DNA techniques. The desired amino acid substitution mutation is made, for example, by modification of the encoding DNA. For example, nucleic acid sequences coding for the polypeptides described herein are generated by mutating the nucleic acid codon encoding the specified amino acid to the desired amino acid using the genetic code shown below:

| TTT | Phe | TCT | Ser | TAT | Tyr | TGT | Cys |
|-----|-----|-----|-----|-----|-----|-----|-----|
| TTC | Phe | TCC | Ser | TAC | Tyr | TGC | Cys |
| TTA | Leu | TCA | Ser |     |     | TGA |     |
| TTG | Leu | TCG | Ser |     |     | TGG | Trp |
| CTT | Leu | CCT | Pro | CAT | His | CGT | Arg |
| CTC | Leu | CCC | Pro | CAC | His | CGC | Arg |
| CTA | Leu | CCA | Pro | CAA | Gln | CGA | Arg |
| CTG | Leu | CCG | Pro | CAG | Gln | CGG | Arg |
| ATT | Ile | ACT | Thr | AAT | Asn | AGT | Ser |
| ATC | Ile | ACC | Thr | AAC | Asn | AGC | Ser |
| ATA | Ile | ACA | Thr | AAA | Lys | AGA | Arg |
| ATG | Met* | ACG | Thr | AAG | Lys | AGG | Arg |
| GTT | Val | GCT | Ala | GAT | Asp | GGT | Gly |
| GTC | Val | GCC | Ala | GAC | Asp | GGC | Gly |
| GTA | Val | GCA | Ala | GAA | Glu | GGA | Gly |
| GTG | Val | GCG | Ala | GAG | Glu | GGG | Gly |

In one embodiment, the nucleic acid sequence is optimized for expression in *E. coli* (e.g., the nucleic acid sequence based on GenBank® AB232927.1, the relevant portion of which is shown in FIG. 13).

Another aspect of the invention relates to a nucleic acid vector comprising the nucleic acid molecule described herein. In one embodiment the vector is an expression vector. Such an expression vector is referred to herein as an expression construct, and comprises a nucleic acid molecule disclosed herein operably-linked to the expression vector useful for expressing the nucleic acid molecule in a cell or cell-free extract. A wide variety of expression vectors can be employed for expressing a nucleic acid molecule encoding a *C. botulinum* neurotoxin of the present invention including, without limitation, a viral expression vector; a prokaryotic expression vector: eukaryotic expression vectors, such as, e.g., a yeast expression vector, an insect expression vector and a mammalian expression vector; and a cell-free extract expression vector. It is further understood that expression vectors useful to practice aspects of these methods may include those which express the *C. botulinum* neurotoxin under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.: BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Cells

Another aspect of the invention relates to a cell comprising the nucleic acid molecule or expression construct described herein. The cell can be for propagation of the nucleic acid or for expression of the nucleic acid, or both. Such cells include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus lichenifor-mis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*: insect cells and cell lines derived from insects, such as, e.g., those derived from *Spodoptera frugiperda. Trichoplusia ni, Drosophila melanogaster* and Manduca sexta; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, 4.sup.th ed. 2000); ANIMAL CELL CULTURE: A PRACTICAL APPROACH (John R. W. Masters ed., Oxford University Press, 3.sup.rd ed. 2000); MOLECULAR CLONING A LABORATORY MANUAL, supra. (2001); BASIC CELL CULTURE: A PRACTICAL APPROACH (John M. Davis. Oxford Press, 2.sup.nd ed. 2002); and CURRENT PROTOCOLS IN MOLECULAR BIOLOGY, supra. (2004). These protocols are routine procedures within the scope of one skilled in the art and from the teaching herein.

The cell can be for expression of the nucleic acid to thereby generate the encoded polypeptide. As such, another aspect of the invention is a method for producing a botulinum neurotoxin protein, an isolated HC, or a polypeptide comprising a modified HC, described herein. Such polypeptides are produced by culturing the host cell that has within it a nucleic acid that encodes the polypeptide, in the context of an expression construct. Culturing is performed under condition suitable for production of the BoNT polypeptide. The expressed polypeptide can be recovered from the culture, purified and formulated by methods known in the art. The expressed polypeptide can also be activated as necessary by methods known in the art. One method of activating the expressed polypeptide is through cleavage (or nicking) by proteases into an active dichain form. Such methods can be adapted from those known in the art, for example as disclosed by Peter F. Bonventre and Lloyd L. KLempe (J. Bacteriol 1960, 79 (1): 23 and Michaeal L. Dekleva and Bibhuti R. DasGupta (Biochemical and Biophysical Research Communicaitons 1989, 162:767-772).

Pharmaceutical Compositions

Another aspect of the present invention relates to a pharmaceutical composition comprising the *C. botulinum* neurotoxin, or chimeric molecule described herein. In one embodiment, the polypeptide described herein is an active ingredient in a composition comprising a pharmaceutically acceptable carrier (referred to herein as a pharmaceutical composition). A "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the composition and is compatible with administration to a subject, for example a human. Such compositions can be specifically formulated for administration via one or more of a number of routes, such as the routes of administration described herein. Supplementary active ingredients also can be incorporated into the compositions. When an agent, formulation or pharmaceutical composition described herein, is administered to a subject, preferably, a therapeutically effective amount is administered. As used herein, the term "therapeutically effective amount" refers to an amount that results in an improvement or remediation of the condition. In one embodiment, the pharmaceutical composition is formulated for administration by injection. In one embodiment, the pharmaceutical composition involves the botulinum neurotoxin encapsulated in microspheres. In one embodiment, the pharmaceutical composition involves the botulinum neurotoxin formulated for transepithelial delivery. In one embodiment, the pharmaceutical composition involves the botulinum neurotoxin formulated for slow release.

In one embodiment, the botulinum neurotoxin, polypeptide, or chimeric molecule of the present invention is in the form of a controlled release formula. Such compositions and methods for administration are provides in U.S. Patent publication No. 2007/0020295, the contents of which are herein incorporated by reference.

Botulinum neurotoxin can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. The proteolytic strains that produce, for example, the botulinum toxin type B serotype may only cleave a portion of the toxin produced. The exact proportion of nicked to unnicked molecules depends on the length of incubation and the temperature of the culture. Therefore, a certain percentage of a preparation of, for example, the botulinum toxin type B toxin may be inactive. In one embodiment, the neurotoxin of the present invention is in an active state. In one embodiment, the neurotoxin is in an inactive state. In one embodiment, a combination of active and inactive neurotoxin is envisioned.

Kits

Also encompassed in the present invention is a kit comprising the BoNT or polypeptide disclosed herein (e.g., in the form of a pharmaceutical composition). The kit may comprise one or more of the compositions described herein packaged in a vial. The kit may further comprise a delivery tool or device for the therapeutic administration of the composition, and/or instructions for therapeutic administration. The kit may have all components therein packaged into a formed container.

Another aspect of the invention relates to a delivery tool or device for administration of the pharmaceutical compositions described herein, pre-loaded with the pharmaceutical composition (e.g., for single use). Such devices may be a syringe or a microneedle device for delivery of the compositions. The syringe may be a single use syringe pre-loaded with an effective amount of the composition. The microneedle device may comprise one or more microneedles coated with the composition described herein, such as is described in U.S. Patent Publication 2010/0196445, the contents of which are incorporated herein in their entirety.

Methods of Treatment

The present invention also includes methods for treating a condition typically treated with a neurotoxin (e.g. skeletal muscle conditions, smooth muscle conditions, glandular conditions, a neuromuscular disorder, an autonomic disorder, pain, or an aesthetic/cosmetic condition). Such conditions are associated with unwanted neuronal activity, as determined by the skilled practitioner. The method comprises the step of administering a therapeutically effective amount of a BoNT or polypeptide/chimeric molecule described herein (e.g. as a pharmaceutical composition) to the appropriate location in the mammal to reduce the unwanted neuronal activity, to thereby treat the condition. Administration is by a route that contacts an effective amount of the composition to neurons exhibiting the unwanted activity.

Specific conditions envisioned for treatment by the methods discussed herein include, without limitation, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder (i.e. all diseases involving urinary incontinence, such as e.g., neurogenic detrusor overactivity or idiopathic overactive bladder), prostate cancer and other cancer forms, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions as well as other secretory disorders, pain from muscle spasms, neuropathic pain, inflammatory pain, heachache pain, such as e.g. migraine, itch (pruritis), acne. In addition, the present invention can be used to treat dermatological or aesthetic/cosmetic conditions, for example, reduction of brow furrows, reduction of skin wrinkles. The present invention can also be used in the treatment of sports injuries.

In addition, the modified neurotoxin can be administered to treat other neuromuscular disorders using well known techniques that are commonly performed with botulinum type A. For example, the present invention can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using botulinum toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. in U.S. Pat. No. 5,766,605 disclose methods for treating the autonomic nervous system; for example, treating autonomic nervous system disorders such as excessive sweating, excessive salivation, asthma, etc., using naturally existing botulinum toxins. The disclosure of Sander et al. is incorporated in its entirety by reference herein. In one embodiment, substantially similar methods to that of Sanders et al. can be employed, but using a modified neurotoxin, to treat autonomic nervous system disorders such as the ones discussed above. For example, a modified neurotoxin can be locally applied to the nasal cavity of the mammal in an amount sufficient to degenerate cholinergic neurons of the autonomic nervous system that control the mucous secretion in the nasal cavity.

Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring botulinum toxin, for example Botulinum type A. The disclosures of Binder are incorporated in its entirety herein by reference. In one embodiment, substantially similar methods to that of Binder can be employed, but using a modified neurotoxin, to treat headache, especially the ones caused by vascular disturbances, muscular tension, neuralgia and neuropathy. Pain caused by muscle spasm can also be treated by an administration of a modified neurotoxin. For example, WO2006001676 (Kang Ahn) discloses methods of using a botulinum neurotoxin for treating knee joint pain caused by saphenous nerve entrapment, WO2008059126 (Christine Favre et al.) discloses methods of using a botulinum neurotoxin for treating pain induced by chemotherapy, WO2008090287 (Christine Favre et al.) discloses methods of using a botulinum neurotoxin for treating pain induced by anti-HIV treatment, WO2009130600 (Christine Favre et al.) discloses methods of using a botulinum neurotoxin for treating pain associated with diabetic neuropathy, and WO2007144493 (Michel Auguet et al.) discloses methods of using a botulinum neurotoxin in combination with an opiate derivative for treating pain. The disclosures of WO2006001676, WO2008059126, WO2008090287, WO2009130600, WO2007144493 are incorporated in its entirety herein by reference. Furthermore, a modified neurotoxin can be administered to a mammal to treat pain that is not associated with a muscular disorder, such as spasm. In one broad embodiment, methods of the present invention to treat non-spasm related pain include central administration or peripheral administration of the modified neurotoxin.

An acute or chronic pain that is not associated with a muscle spasm can also be alleviated with a local, peripheral administration of the modified neurotoxin to an actual or a perceived pain location on the mammal. In one embodiment, the modified neurotoxin is administered subcutaneously at or near the location of pain, for example, at or near a cut. In some embodiments, the modified neurotoxin is administered intramuscularly at or near the location of pain, for example, at or near a bruise location on the mammal. In some embodiments, the modified neurotoxin is injected directly into a joint of a mammal, for treating or alleviating pain caused by arthritic conditions. Also, frequent repeated injection or infusion of the modified neurotoxin to a peripheral pain location is within the scope of the present invention Routes of administration for such methods are known in the art and easily adapted to the methods described herein by the skilled practitioner (e.g., see for example, Harrison's Principles of Internal Medicine (1998), edited by Anthony Fauci et al., 14th edition, published by McGraw Hill). By way of non-limiting example, the treatment of a neuromuscular disorder can comprise a step of locally administering an effective amount of the molecule to a muscle or a group of muscles, the treatment of an autonomic disorder can comprise a step of locally administering an effective of the molecule to a gland or glands, and the treatment of pain can comprise a step of administering an effective amount of the molecule the site of the pain. In addition, the treatment of pain can comprise a step of administering an effective amount of a modified neurotoxin to the spinal cord.

It is also envisioned that the modified $H_C$ (e.g., B-$H_C$) described herein can be utilized as a delivery tool to target neurons and other cell types that express human synaptotagmin II in humans. For example, the modified $H_C$ linked to another bioactive molecule (e.g., therapeutic agent) covalently or non-covalently to thereby form a chimeric molecule described herein, can serve as the targeting vehicle to deliver the bioactive molecule to neurons and other cell types that express human synaptotagmin II in humans by binding to human Syt I and/or Syt II. As such, another aspect of the invention relates to the use of a chimeric polypeptide molecule described herein to deliver the bioactive molecule to a neuron in a human subject. The second portion of the molecule can be a bioactive molecule such as a therapeutic agent (e.g., a polypeptide or drug). Linkage of the first and second portions of the molecule can be covalent (e.g., in the form of a fusion protein) or non-covalent. Methods of such linkage are known in the art and can readily be applied by the skilled practitioner. The chimeric polypeptide molecule would be administered by a route that resulted in contacting of the polypeptide to the neurons expressing the receptor to which the modified B-H$_C$ specifically binds (the target neuron), as described herein.

Identifying Receptor Binding Activity

Another aspect of the invention relates to a method for identifying a modified BoNT receptor binding domain for its ability to bind to a receptor (e.g. a human Syt I or human Syt II, or human SV2). The method utilizes the 2-hybrid assay system and utilizes fusions proteins made of the receptor and of the modified Hc respectively fused (expressed as fusions proteins) to the respective "bait" and "prey" subunits used in the 2-hybrid assay (e.g., Gal 4 transcription activation system utilizing an activation domain and a DNA binding domain). The 2-hybrid assay is typically performed in yeast (*S. cerevisiae*), but similar assay systems have been developed for use in other single celled organisms as well such as in *E. coli*. Those systems are equally comparable. In one embodiment, the bacterial adenylate cyclase 2-hybrid assay is used (Karimova et al., Proc Natl Acad Sci USA. May 12, 1998; 95 (10): 5752-5756, the contents of which are incorporated herein by reference). The system uses T18 and T25 as bait and prey, and can utilize *E. coli* BTH101 cells.

The modified Hc is expressed as a fusion protein with T18 (referred to as a first fusion protein) in the *E. coli* of the 2-hybrid assay. In the method, the receptor (or a binding fragment thereof such as h-Syt II a.a. 1-87) is co-expressed as a fusion protein with T25 (referred to as a second fusion protein) in the *E. coli* of the 2-hybrid assay. The assay utilizes a positive indicator of interaction between the respective molecules via their respective fusions. One possible positive indicator is color development. Clonal *E. coli* colonies expressing both the first and second fusion proteins are grown on solid media containing the appropriate selective and reporting media (e.g., ampicillin, kanamycin, X-gal, and IPTG) for an amount of time to allow for generation of a positive indication (e.g., color generation) from positive colonies. Binding of the modified binding domain to the receptor fragment will lead to the positive indication (e.g., expression of LacZ gene and result in generation of a blue color in colonies grown on X-gal plates).

The colonies are analyzed for such positive indication (e.g., color development) when compared to appropriate controls (positive and negative). The analyzing can be visually or by a non-human machine. An appropriate negative control that fails to produce appreciable positive indication (e.g., LacZ expression) is used (e.g. a clonal colony lacking a key component of the assay system such as having bait and prey that are expressed without a fusion). An appropriate strong positive control can also be used. One example of a strong positive control for the human Syt II receptor in the assay is a B1-Hc with a substitution mutation at E1191 (M/C/V or Q). A weakly positive control can also be used to identify the strength of the binding. One example of a weakly positive control for human Syt II receptor in the assay is a B1-Hc with a substitution mutation at W1178

(Q/Y/A or S). Identification of the positive indication (e.g., color development) indicates that the modified Hc binds the receptor. Identification of strong positive indication such as strong color development (e.g. above a weakly positive control) indicates the Hc binds the receptor with high affinity.

The modified Hc used in the assay can be any modified Hc disclosed herein. By way of non-limiting example, the modified Hc may contain one, two or three substitution mutations such as those disclosed herein. The modified Hc may be of any serotype/strain or subtype as disclosed herein.

The embodiments described here and in the following examples are for illustrative purposes only, and various modifications or changes apparent to those skilled in the art are included within the scope of the invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to describe the present invention, in connection with percentages means±1%.

In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES FOR BACKGROUND AND DETAILED DESCRIPTION

1. Schiavo, G., Matteoli, M. & Montecucco, C. Neurotoxins affecting neuroexocytosis. *Physiol Rev* 80, 717-766 (2000).

2. Johnson, E. A. Clostridial toxins as therapeutic agents: benefits of nature's most toxic proteins. *Annu Rev Microbiol* 53, 551-575 (1999).

3. Aoki, K. R. Botulinum toxin: a successful therapeutic protein. *Curr Med Chem* 11, 3085-3092 (2004).

4. Montecucco, C. & Molgo, J. Botulinal neurotoxins: revival of an old killer. *Curr Opin Pharmacol* 5, 274-279 (2005).

5. Lange, O., et al. Neutralizing antibodies and secondary therapy failure after treatment with botulinum toxin type A: much ado about nothing? *Clin Neuropharmacol* 32, 213-218 (2009).

6. Chapman, M. A., Barron, R., Tanis, D. C., Gill, C. E. & Charles, P. D. Comparison of botulinum neurotoxin preparations for the treatment of cervical dystonia. *Clin Ther* 29, 1325-1337 (2007).

7. Cote, T. R., Mohan, A. K., Polder, J. A., Walton, M. K. & Braun, M. M. Botulinum toxin type A injections: adverse events reported to the US Food and Drug Administration in therapeutic and cosmetic cases. *J Am Acad Dermatol* 53, 407-415 (2005).

8. Dong, M., Tepp, W. H., Liu, H., Johnson, E. A. & Chapman, E. R. Mechanism of botulinum neurotoxin B and G entry into hippocampal neurons. J Cell Biol 179, 1511-1522 (2007).

9. Peng, L., Tepp, W. H., Johnson, E. A. & Dong, M. Botulinum neurotoxin D uses synaptic vesicle protein SV2 and gangliosides as receptors. PLOS Pathog 7, e1002008 (2011).

10. Dong, M., et al. Synaptotagmins I and II mediate entry of botulinum neurotoxin B into cells. *J Cell Biol* 162, 1293-1303 (2003).

11. Nishiki, T., et al. Identification of protein receptor for *Clostridium botulinum* type B neurotoxin in rat brain synaptosomes. *J Biol Chem* 269, 10498-10503 (1994).

12. Rummel, A., Karnath, T., Henke, T., Bigalke, H. & Binz, T. Synaptotagmins I and II act as nerve cell receptors for botulinum neurotoxin G. *J Biol Chem* 279, 30865-30870 (2004).

13. Peng, L., et al. Botulinum neurotoxin D-C uses synaptotagmin I/II as receptors and human synaptotagmin II is not an effective receptor for type B, D-C, and G toxins. *J Cell Sci* (2012).

14. Dong, M., et al. SV2 is the protein receptor for botulinum neurotoxin A. *Science* 312, 592-596 (2006).

15. Dong, M., et al. Glycosylated SV2A and SV2B mediate the entry of botulinum neurotoxin E into neurons. *Mol Biol Cell* 19, 5226-5237 (2008).

16. Mahrhold, S., Rummel, A., Bigalke, H., Davletov, B. & Binz, T. The synaptic vesicle protein 2C mediates the uptake of botulinum neurotoxin A into phrenic nerves. *FEBS Lett* 580, 2011-2014 (2006).

17. Rummel, A., et al. Botulinum neurotoxins C, E and F bind gangliosides via a conserved binding site prior to stimulation-dependent uptake with botulinum neurotoxin F utilising the three isoforms of SV2 as second receptor. *J Neurochem* 110, 1942-1954 (2009).

18. Fu, Z., Chen, C., Barbieri, J. T., Kim, J. J. & Baldwin, M. R. Glycosylated SV2 and gangliosides as dual receptors for botulinum neurotoxin serotype F. *Biochemistry* 48, 5631-5641 (2009).

19. Montecucco, C. How do tetanus and botulinum toxins bind to neuronal membranes? *TIBS,* 314-317 (1986).

20. Nishiki, T., et al. The high-affinity binding of *Clostridium botulinum* type B neurotoxin to synaptotagmin II associated with gangliosides GT1b/GD1a. *FEBS Lett* 378, 253-257 (1996).

21. Pang, Z. P., et al. Synaptotagmin-2 is essential for survival and contributes to Ca2+ triggering of neurotransmitter release in central and neuromuscular synapses. *J Neurosci* 26, 13493-13504 (2006).

22. Strotmeier, J., Willjes, G., Binz, T. & Rummel, A. Human synaptotagmin-II is not a high affinity receptor for botulinum neurotoxin B and G: increased therapeutic dosage and immunogenicity. *FEBS Lett* 586, 310-313 (2012).

23. Craxton, M. A manual collection of Syt, Esyt, Rph3a, Rph3al, Doc2, and Dblc2 genes from 46 metazoan genomes—an open access resource for neuroscience and evolutionary biology. *BMC Genomics* 11, 37 (2010).

24. Brin, M. F., et al. Safety and efficacy of NeuroBloc (botulinum toxin type B) in type A-resistant cervical dystonia. *Neurology* 53, 1431-1438 (1999).

25. Pappert, E. J. & Germanson, T. Botulinum toxin type B vs. type A in toxin-naive patients with cervical dystonia: Randomized, double-blind, noninferiority trial. *Mov Disord* 23, 510-517 (2008).

26. Wang, J., et al. Longer-acting and highly potent chimaeric inhibitors of excessive exocytosis created with domains from botulinum neurotoxin A and B. *Biochem J* 444, 59-67 (2012).

27. Rummel, A., Mahrhold, S., Bigalke, H. & Binz, T. Exchange of the H(CC) domain mediating double receptor recognition improves the pharmacodynamic properties of botulinum neurotoxin. *FEBS J* 278, 4506-4515 (2011).

28. Kozaki, S., et al. Characterization of *Clostridium botulinum* type B neurotoxin associated with infant botulism in japan. *Infect Immun* 66, 4811-4816 (1998).

29. Ihara, H., et al. Sequence of the gene for *Clostridium botulinum* type B neurotoxin associated with infant botulism, expression of the C-terminal half of heavy chain and its binding activity. *Biochim Biophys Acta* 1625, 19-26 (2003).

30. Rummel, A., Mahrhold, S., Bigalke, H. & Binz, T. The HCC-domain of botulinum neurotoxins A and B exhibits a singular ganglioside binding site displaying serotype specific carbohydrate interaction. *Mol Microbiol* 51, 631-643 (2004).

31. Chai, Q., et al. Structural basis of cell surface receptor recognition by botulinum neurotoxin B. *Nature* 444, 1096-1100 (2006).

32. Jin, R., Rummel, A., Binz, T. & Brunger, A. T. Botulinum neurotoxin B recognizes its protein receptor with high affinity and specificity. *Nature* 444, 1092-1095 (2006).

33. Arnon, S. S., et al. Botulinum toxin as a biological weapon: medical and public health management. *Jama* 285, 1059-1070 (2001).

34. Moriishi, K., et al. Mosaic structures of neurotoxins produced from *Clostridium botulinum* types C and D organisms. *Biochim Biophys Acta* 1307, 123-126 (1996).

35. Hill, K. K., et al. Genetic diversity among Botulinum Neurotoxin-producing clostridial strains. *J Bacteriol* 189, 818-832 (2007).

36. Lalli, G., et al. Functional characterisation of tetanus and botulinum neurotoxins binding domains. *J Cell Sci* 112 (Pt 16), 2715-2724 (1999).

The present invention may be as defined in any one of the following numbered paragraphs.

1. A botulinum neurotoxin (BoNT) polypeptide comprising:
   a) a protease domain;
   b) a protease cleavage site;
   c) a translocation domain; and d) a modified receptor binding domain of *Clostridial botulinum* serotype B (B-H_c), comprising one or more substitution mutations corresponding to substitution mutations in serotype B, strain 1, selected from the group consisting of:

E1191C, E1191V, E1191L, E1191Y, S1199W, S1199E, S1199H, W1178Y, W1178Q, W1178A, W1178S, Y1183C, Y1183P and combinations thereof.

2. The BoNT polypeptide of paragraph 1, wherein the modified (B-H_c) comprises one substitution mutation corresponding to a substitution mutation in serotype B, strain 1, selected from the group consisting of E1191C, E1191V, E1191L, E1191Y, S1199E, S1199H, W1178Y, W1178Q, W1178A, W1178S, Y1183C, and Y1183P.

3. The BoNT polypeptide of paragraph 2, wherein the modified (B-H_c) comprises the substitution mutation corresponding to E1191C in serotype B, strain 1.

4. The BoNT polypeptide of paragraph 2, wherein the modified (B-H_c) comprises the substitution mutation corresponding to E1191V in serotype B, strain 1.

5. The BoNT polypeptide of paragraph 1, wherein the modified (B-H_c) comprises two substitution mutations.

6. A botulinum neurotoxin (BoNT) polypeptide comprising:

a) a protease domain;
 b) a protease cleavage site;
 c) a translocation domain; and
 d) a modified receptor binding domain of *Clostridial botulinum* serotype B (B-H_c), comprising two or more substitution mutations corresponding to substitution mutations in serotype B, strain 1, wherein one of the substitution mutations is selected from the group consisting of:

E1191Q, E1191M, E1191C, E1191V, E1191L, and E1191Y.

7. The BoNT polypeptide of paragraph 6, wherein one other of the substitution mutations corresponds to S1199W, S1199E, S1199H, S1199Y, W1178Y, W1178Q, W1178A, W1178S, Y1183C, Y1183P, S1199F or S1199L in serotype B, strain 1.

8. The BoNT polypeptide of any one of paragraphs 5-7, wherein the two substitution mutations correspond to E1191M and S1199W, E1191M and W1178Q, E1191C and S1199W; E1191C and S1199Y, E1191C and W1178Q, E1191Q and S1199W, E1191V and S1199W, E1191V and S1199Y, or E1191V and W1178Q, in serotype B, strain 1.

9. The BoNT polypeptide of any one of paragraphs 5-8, wherein the two substitution mutations correspond to E1191M and S1199W in serotype B, strain 1.

10. The BoNT polypeptide of one of paragraphs 5-8, wherein the two substitution mutations correspond to E1191M and W1178Q in serotype B, strain 1.

11. The BoNT polypeptide of one of paragraphs 5-8, wherein the two substitution mutations correspond to E1191C and S1199W in serotype B, strain 1.

12. The BoNT polypeptide of one of paragraphs 5-8, wherein the two substitution mutations correspond to E1191C and S1199Y in serotype B, strain 1.

13. The BoNT polypeptide of one of paragraphs 5-8, wherein the two substitution mutations correspond to E1191C and W1178Q in serotype B, strain 1.

14. The BoNT polypeptide of one of paragraphs 5-8, wherein the two substitution mutations correspond to E1191Q and S1199W in serotype B, strain 1.

15. The BoNT polypeptide of one of paragraphs 5-8, wherein the two substitution mutations correspond to E1191V and S1199W in serotype B, strain 1.

16. The BoNT polypeptide of one of paragraphs 5-8, wherein the two substitution mutations correspond to E1191V and S1199Y in serotype B, strain 1.

17. The BoNT polypeptide of one of paragraphs 5-8, wherein the two substitution mutations correspond to E1191V and W1178Q in serotype B, strain 1.

18. The BoNT polypeptide of paragraph 6, wherein the modified (B-H_c) comprises three substitution mutations.

19. The BoNT polypeptide of paragraph 18, wherein the three substitution mutations are at positions that correspond to E1191, Y1183 and S1199 or to E1191, S1199 and W1178 of serotype B, strain 1.

20. The BoNT polypeptide of paragraph 19, wherein the three substitution mutations correspond to E1191M, S1199W and W1178Q of serotype B, strain 1.

21. A botulinum neurotoxin (BoNT) polypeptide comprising:

a) a protease domain;
 b) a protease cleavage site;
 c) a translocation domain; and
 d) a modified receptor binding domain of *Clostridial botulinum* serotype B (B-H_c), comprising a substitution mutation at a position corresponding to S1199 or S1201 of serotype B, strain 1.

22. The BoNT polypeptide of any one of paragraphs 1-21, wherein the modified B-H_c is of strain 1.

23. The BoNT polypeptide of any one of paragraphs 1-22 wherein the protease domain, translocation domain, and protease cleavage site are from serotype selected from the group consisting of A, B, C, D, E, F, G, and combinations thereof.

24. The BoNT polypeptide of paragraph 23, wherein the protease domain, translocation domain, and protease cleavage site are from serotype B, strain 1.

25. The BoNT polypeptide of paragraph 23, wherein the protease domain, translocation domain, and protease cleavage site are from serotype A, strain 1.

26. A polypeptide comprising a modified receptor binding domain of *Clostridial botulinum* serotype B (B-H_c) comprising one or more substitution mutations corresponding to substitution mutations in serotype B, strain 1, selected from the group consisting of:

E1191C, E1191V, E1191L, E1191Y, S1199W, S1199E, S1199H, W1178Y, W1178Q, W1178A, W1178S, Y1183C, Y1183P and combinations thereof.

27. The polypeptide of paragraph 26, wherein the modified (B-H_c) comprises two substitution mutations.

28. A polypeptide comprising a modified receptor binding domain of *Clostridial botulinum* serotype B (B-H_c) comprising two or more substitution mutations corresponding to substitution mutations in serotype B, strain 1, wherein one of the substitution mutations is selected from the group consisting of E1191Q, E1191M, E1191C, E1191V, E1191L, and E1191Y.

29. The polypeptide of paragraph 26, wherein one of the substitution mutations corresponds to S1199W, S1199E, S1199H, S1199Y, W1178Y, W1178Q, W1178A, W1178S, Y1183C, Y1183P, S1199F or S1199L in serotype B, strain 1.

30. The polypeptide of any one of paragraphs 27-29, wherein the two substitution mutations correspond to E1191M and S1199W, E1191M and W1178Q, E1191C and S1199W; E1191C and S1199Y, E1191C and W1178Q, E1191Q and S1199W, E1191V and S1199W, E1191V and S1199Y, or E1191V and W1178Q, in serotype B, strain 1.

31. The polypeptide of any one of paragraphs 27-30, wherein the two substitution mutations correspond to E1191M and S1199W in serotype B, strain 1.

32. The polypeptide of one of paragraphs 27-30, wherein the two substitution mutations correspond to E1191M and W1178Q in serotype B, strain 1.

33. The polypeptide of one of paragraphs 27-30, wherein the two substitution mutations correspond to E1191C and S1199W in serotype B, strain 1.

34. The polypeptide of one of paragraphs 27-30, wherein the two substitution mutations correspond to E1191C and S1199Y in serotype B, strain 1.

35. The polypeptide of one of paragraphs 27-30, wherein the two substitution mutations correspond to E1191C and W1178Q in serotype B, strain 1.

36. The polypeptide of one of paragraphs 27-30, wherein the two substitution mutations correspond to E1191Q and S1199W in serotype B, strain 1.

37. The polypeptide of one of paragraphs 27-30, wherein the two substitution mutations correspond to E1191V and S1199W in serotype B, strain 1.

38. The polypeptide of one of paragraphs 27-30, wherein the two substitution mutations correspond to E1191V and S1199Y in serotype B, strain 1.

39. The polypeptide of one of paragraphs 27-30, wherein the two substitution mutations correspond to E1191V and W1178Q in serotype B, strain 1.

40. The polypeptide of paragraph 30, wherein the modified (B-H$_c$) comprises three substitution mutations.

41. The polypeptide of paragraph 40, wherein the three substitution mutations are at positions that correspond to E1191, Y1183 and S1199 or to E1191, S1199 and W1178 of serotype B, strain 1.

42. The polypeptide of paragraph 41, wherein the three substitution mutations correspond to E1191M, S1199W and W1178Q of serotype B, strain 1.

43. The polypeptide of any one of paragraphs 26-42, wherein the modified B-H$_c$ is of strain 1.

44. A chimeric molecule comprising a first portion that is a modified receptor binding domain of *Clostridial botulinum* serotype B (B-H$_c$) linked to a second portion, wherein the modified B-H$_c$ comprises one or more substitution mutations selected from the group consisting of:

E1191C, E1191V, E1191L, E1191Y, S1199W, S1199E, S1199H, W1178Y, W1178Q, W1178A, W1178S, Y1183C, Y1183P and combinations thereof.

45. The chimeric molecule of paragraph 44, wherein the modified B-H$_c$ comprises two substitution mutations.

46. A chimeric molecule comprising a first portion that is a modified receptor binding domain of *Clostridial botulinum* serotype B (B-H$_c$) linked to a second portion, wherein the modified B-H$_c$ comprises two or more substitution mutations corresponding to substitution mutations in serotype B, strain 1, wherein one of the substitution mutations is selected from the group consisting of:

E1191Q, E1191M, E1191C, E1191V, E1191L, and E1191Y.

47. The chimeric molecule of paragraph 46, wherein one of the substitution mutations corresponds to S1199W, S1199E, S1199H, S1199Y, W1178Y, W1178Q, W1178A, W1178S, Y1183C, Y1183P, S1199F or S1199L in serotype B, strain 1.

48. The chimeric molecule of any one of paragraphs 45-47, wherein the two substitution mutations correspond to E1191M and S1199W, E1191M and W1178Q, E1191C and S1199W; E1191C and S1199Y, E1191C and W1178Q, E1191Q and S1199W, E1191V and S1199W, E1191V and S1199Y, or E1191V and W1178Q, in serotype B, strain 1.

49. The chimeric molecule of any one of paragraphs 45-47, wherein the two substitution mutations correspond to E1191M and S1199W in serotype B, strain 1.

50. The chimeric molecule of any one of paragraphs 45-47, wherein the two substitution mutations correspond to E1191M and W1178Q in serotype B, strain 1.

51. The chimeric molecule of any one of paragraphs 45-47, wherein the two substitution mutations correspond to E1191C and S1199W in serotype B, strain 1.

52. The chimeric molecule of any one of paragraphs 45-47, wherein the two substitution mutations correspond to E1191C and S1199Y in serotype B, strain 1.

53. The chimeric molecule of any one of paragraphs 45-47, wherein the two substitution mutations correspond to E1191C and W1178Q in serotype B, strain 1.

54. The chimeric molecule of any one of paragraphs 45-47, wherein the two substitution mutations correspond to E1191Q and S1199W in serotype B, strain 1.

55. The chimeric molecule of any one of paragraphs 45-47, wherein the two substitution mutations correspond to E1191V and S1199W in serotype B, strain 1.

56. The chimeric molecule of any one of paragraphs 45-47, wherein the two substitution mutations correspond to E1191V and S1199Y in serotype B, strain 1.

57. The chimeric molecule of any one of paragraphs 45-47, wherein the two substitution mutations correspond to E1191V and W1178Q in serotype B, strain 1.

58. The chimeric molecule of one of paragraph 45 or 46, wherein the modified (B-H$_c$) comprises three substitution mutations.

59. The chimeric molecule of paragraph 58, wherein the three substitution mutations are at positions that correspond to E1191, Y1183 and S1199 or to E1191, S1199 and W1178 of serotype B, strain 1.

60. The chimeric molecule of paragraph 59, wherein the three substitution mutations correspond to E1191M, S1199W and W1178Q of serotype B, strain 1.

61. The chimeric molecule of any one of paragraphs 44-60, wherein the modified B-H$_c$ is of strain 1.

62. The chimeric molecule of any one of paragraphs 44-61, wherein the first portion and the second portion are linked covalently.

63. The chimeric molecule of any one of paragraphs 46-61, wherein the first portion and the second portion are linked non-covalently.

64. The chimeric molecule of any one of paragraphs 44-61 wherein the second portion is selected from the group consisting of a small molecule, a nucleic acid, a short polypeptide and a protein.

65. The chimeric molecule of paragraph 64, wherein the second portion is a bioactive molecule.

66. The chimeric molecule of paragraph 64 or 65, wherein the second portion is a therapeutic polypeptide or non-polypeptide drug.

67. The BoNT polypeptide, polypeptide or chimeric molecule of any one of paragraphs 1-66 that exhibits significantly enhanced binding of the modified B-H$_c$ to human SytII and/or significantly reduced binding of the modified B-H$_c$ to human Syt I as compared to an identical molecule lacking the substitution mutation(s).

68. The BoNT polypeptide, polypeptide or chimeric molecule of any one of paragraphs 1-66 wherein the substitution mutation produces significantly enhanced binding to human SytII and/or significantly enhanced binding to human Syt I as compared to an identical molecule lacking the substitution mutation(s).

69. A nucleic acid comprising a nucleotide sequence that encodes the polypeptide or chimeric molecule of any one of paragraphs 1-68.

70. A nucleic acid vector comprising the nucleic acid of paragraph 69.

71. A cell comprising the nucleic acid vector of paragraph 70 or the nucleic acid of paragraph 69.

72. A cell expressing the polypeptide or chimeric molecule of any one of paragraphs 1-68

73. A pharmaceutical composition comprising the botulinum neurotoxin (BoNT) polypeptide of any one of paragraphs 1-25, 67 or 68, or the chimeric molecule of any one of paragraphs 44-66, or the nucleic acid vector of paragraph 70 or the nucleic acid of paragraph 69.

74. The pharmaceutical composition of paragraph 73, further comprising a pharmaceutically acceptable excipient.

75. A kit comprising a pharmaceutical composition of paragraph 73 or 74 and directions for therapeutic administration of the pharmaceutical composition.

76. A method to produce a botulinum neurotoxin (BoNT) polypeptide, the method comprising the steps of culturing the cell of paragraph 72 under conditions wherein said BoNT polypeptide is produced.

77. The method of paragraph 76 further comprising one or more of the following steps:

recovering the BoNT polypeptide from the culture, purifying the BoNT polypeptide, activating the BoNT polypeptide, and/or formulating the BoNT polypeptide.

78. A method for treating a condition associated with unwanted neuronal activity comprising administering a therapeutically effective amount of the BoNT polypeptide of any one of paragraphs 1-25, 67 or 68 to a subject to thereby contact one or more neurons exhibiting unwanted neuronal activity, to thereby treat the condition.

79. The method of paragraph 78, wherein the condition is selected from the group consisting of, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions, secretory disorders, pain from muscle spasms, headache pain, migraine, and dermatological or aesthetic/cosmetic conditions.

80. The botulinum neurotoxin (BoNT) polypeptide of any one of paragraphs 1-25, 67 or 68, the pharmaceutical composition of one of paragraphs 73 or 74 or the chimeric molecule of any one of paragraphs 44-66, or the polypeptide of any one of paragraphs 26-43, for use in medicine.

81. The botulinum neurotoxin (BoNT) polypeptide of any one of paragraphs 1-25, 67 or 68, the pharmaceutical composition of one of paragraphs 73 or 74, or the chimeric molecule of any one of paragraphs 44-66, or the polypeptide of any one of paragraphs 67-43, for use in treating a condition associated with unwanted neuronal activity.

82. A method for identifying a modified receptor binding domain of botulinum neurotoxin for binding to a receptor comprising:

a) expressing the modified receptor binding domain as a first fusion protein with T18 subunit of bacterial adenylate cyclase in a 2-hybrid assay, and expressing the receptor as a second fusion protein with T25 subunit of bacterial adenylate cyclase in the 2-hybrid assay;

b) analyzing a clonal *E. coli* colony that expresses both the first and second fusion protein for the presence of a positive indication above a negative control; and c) identifying the modified receptor binding domain expressed by the colony exhibiting the positive indication as binding to the receptor.

83. The method of paragraph 82 wherein the positive indication is color development.

84. The method of any one of paragraphs 82-83, further comprising the step of analyzing the colony for the positive indication against a weakly positive control, and further identifying the modified receptor binding domain expressed by the colony exhibiting above the weakly positive control as binding to the receptor with high affinity.

85. The method of paragraph 82-84 that is performed with a library of modified receptor binding domains each expressed within respective colonies.

86. The method of any one of paragraphs 82-85 wherein the receptor is human.

87. The method of any one of paragraphs 82-86 wherein the modified receptor binding domain comprises one or more substitution mutations, wherein one of the substitution mutations corresponds to a mutation in serotype B, strain 1, selected from the group consisting of: E1191M, E1191Q, E1191C, E1191V, E1191L, E1191Y, S1199W, S1199E, S1199H, S1199F, S1199L W1178Y, W1178Q, W1178A, W1178S, Y1183C, Y1183P and S1199Y.

The invention is further illustrated by the following examples, which should not be construed as further limiting.

EXAMPLES

Identification of Single Mutations that Enhance BoNT/B Binding to h-Syt II

The co-crystal structure of BoNT/B bound to rat Syt II luminal domain has been solved by two studies in 2006[25,26]. The structural information provided a sound basis for us to focus on limited numbers of residues within the binding interface for rational design mutagenesis studies. The conserved phenylalanine at position 54 forms multiple hydrophobic contacts with BoNT/B. Because leucine (in humans) is also hydrophobic, disruption of BoNT/B binding is likely due to size/shape differences between phenylalanine and leucine. The key was to identify possible changes in BoNT/B $H_C$ region that may accommodate the change from phenylalanine to leucine.

All residues in BoNT/B that contribute to interactions between BoNT/B and Syt II were examined. These residues were well-defined by the BoNT/B-Syt II co-crystal structure, including K1113, D1115, S1116, P1117, V1118, W1178, Y1181, Y1183, E1191, K1192, F1194, A1196, P1197, S1199, S1201, E1203, F1204, E1245, and Y1256 (FIG. 3), a total of 19 positions. The strategy was to first systematically replace the residues at each of these 19 positions with all other 19 possible amino acids and then test binding of these mutated BoNT/B-$H_C$ to h-Syt II. Therefore, a total of 19×19=361 single point mutations needed to be generated and tested.

Figure 4B:
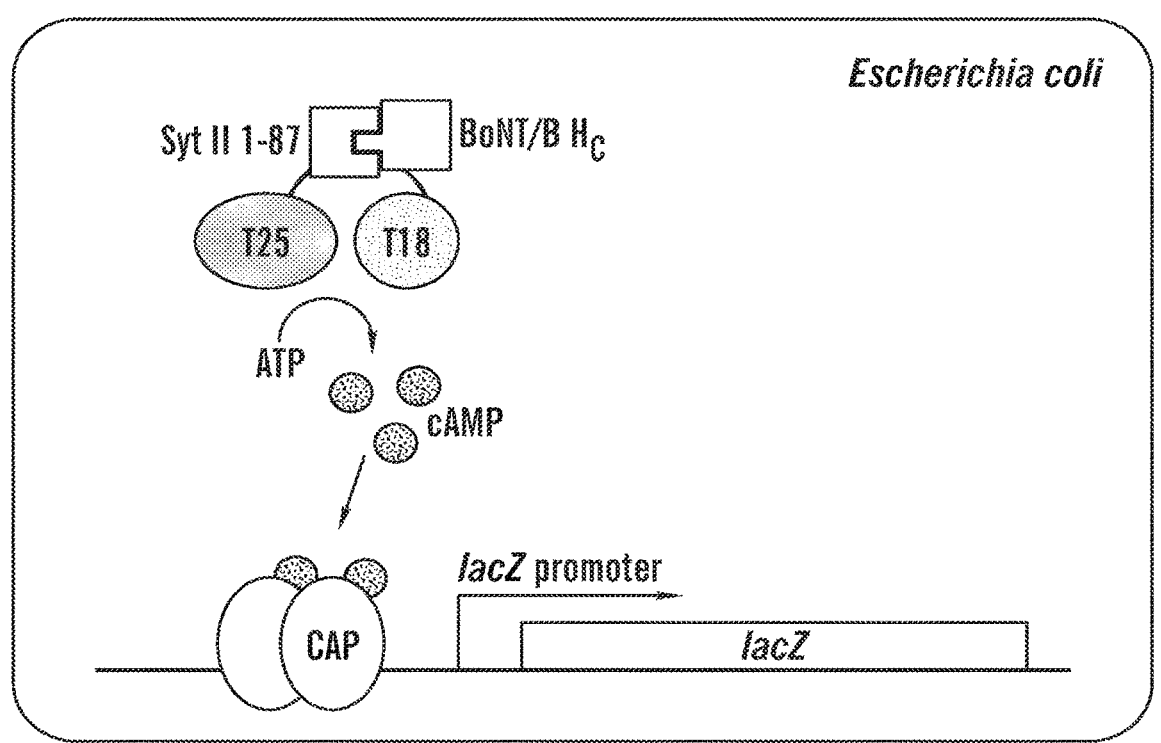

A bacterial adenylate cyclase two hybrid system (BACTH) was used to generate these 361 mutations and test their binding to h-Syt II as described in FIG. 4. Briefly, wild type (WT) BoNT/B-$H_C$ was subcloned into a vector in frame with the split fragment (T18) of the bacterial adenylate cyclase. This T18-BoNT/B-$H_C$ fusion construct was amplified by PCR with primers harboring random tri-nucleotides (NNN) at the selected position in BoNT/B-H$_C$ (FIG. 4A). This generated a pool of constructs that encode all 20 different amino acids at the select site. This pool of constructs were then co-transformed into bacteria (*E. coli* strain BTH101), together with a construct that expresses h-Syt II (1-87) fused with the other half of the split bacterial adenylate cyclase (T25). Binding of a mutant BoNT/B-H$_C$ to h-Syt II brought T18 and T25 together and recovered the activity of adenylate cyclase, which lead to expression of lacZ gene and results in blue colonies on X-gal plates (FIG. 4B). The specific mutations introduced into BoNT/B-H$_C$ were identified by extracting and sequencing the constructs from these blue colonies.

Using this BACTH method, all 19 selected sites were screened in BoNT/B-H$_C$. The numbers of total colonies and blue colonies for each site are listed in FIG. 5A. Greater than 380 total colonies were counted for each position. The total colony number determined the possibility of covering all 20 amino acids at the selected mutation site. This was calculated by Clark-Carbon equation: $P=1-(1-f)^N$, where f reflects the number of possible residues (f=1/20) here as there are 20 different amino acids), and N is the total number of colonies. With a minimal number of 380) colonies, the probability of covering all 20 amino acids at a position is 99.8%. Therefore, it is likely that all 20 possible residues were covered once the number of colonies on the plates was over 380.

As shown in FIG. 5A, four positions were found to result in blue colonies, including E1191 (22.7%), W11178 (7.8%), Y1183 (4.0%), and S1199 (5.1%). Among these four positions, E1191 had the highest levels of blue colonies. In addition, the blue colonies from E1191 also showed deeper blue color as compared to the other three sites, which suggested that the interaction between BoNT/B-H$_C$ and h-Syt II could be stronger with E1191 mutations. Plasmids were extracted and sequenced from these blue colonies. The identified residues at each site are listed in FIG. 5B: E1191M/C/V/Q/L/Y, Y1183/C/P, S1199W/E/Y/H, W1178Y/Q/A/S.

The interactions between human Syt II and those identified mutants were further verified by measuring the levels of β-galactosidase produced in bacteria, which was proportional to the total level of adenylate cyclase activity reconstituted by interactions between T18-BoNT/B-H$_C$ and T25-h-Syt II. Four mutations at E1191 sites, E1191M/C/V/Q, showed the strongest β-galactosidase activity among all mutations tested (FIG. 6A), suggesting that replacing E1191 with one of these four residues significantly enhanced binding of T18-BoNT/B-H$_C$ to T25-h-Syt II.

Figure 6A:
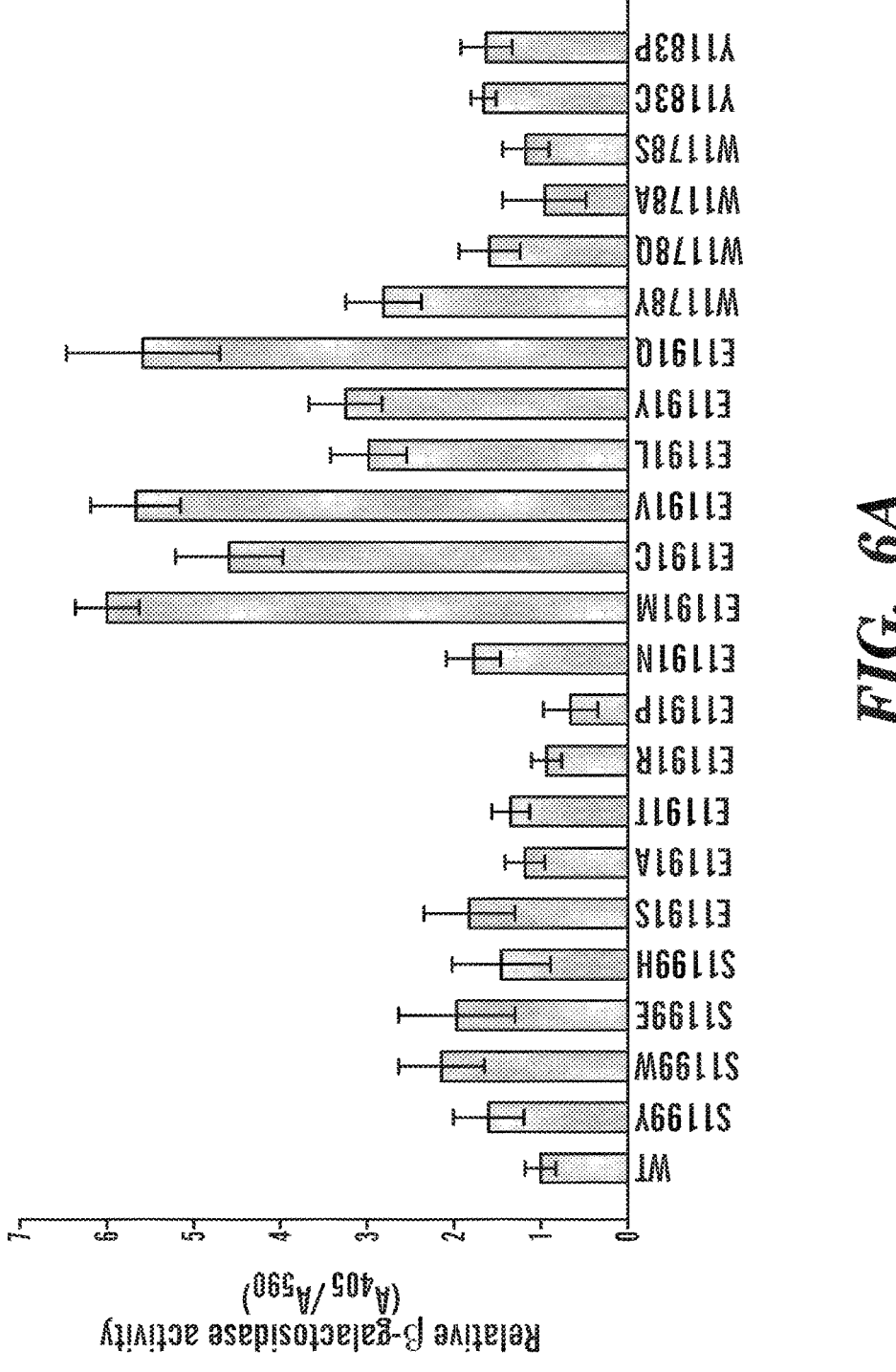
FIG. 6A-FIG. 6B shows experimental results that indicate the semi-quantitative measurement of the interactions between indicated BoNT/B-H$_C$ mutants with human Syt II in BACTH assay.
Figure 6B:
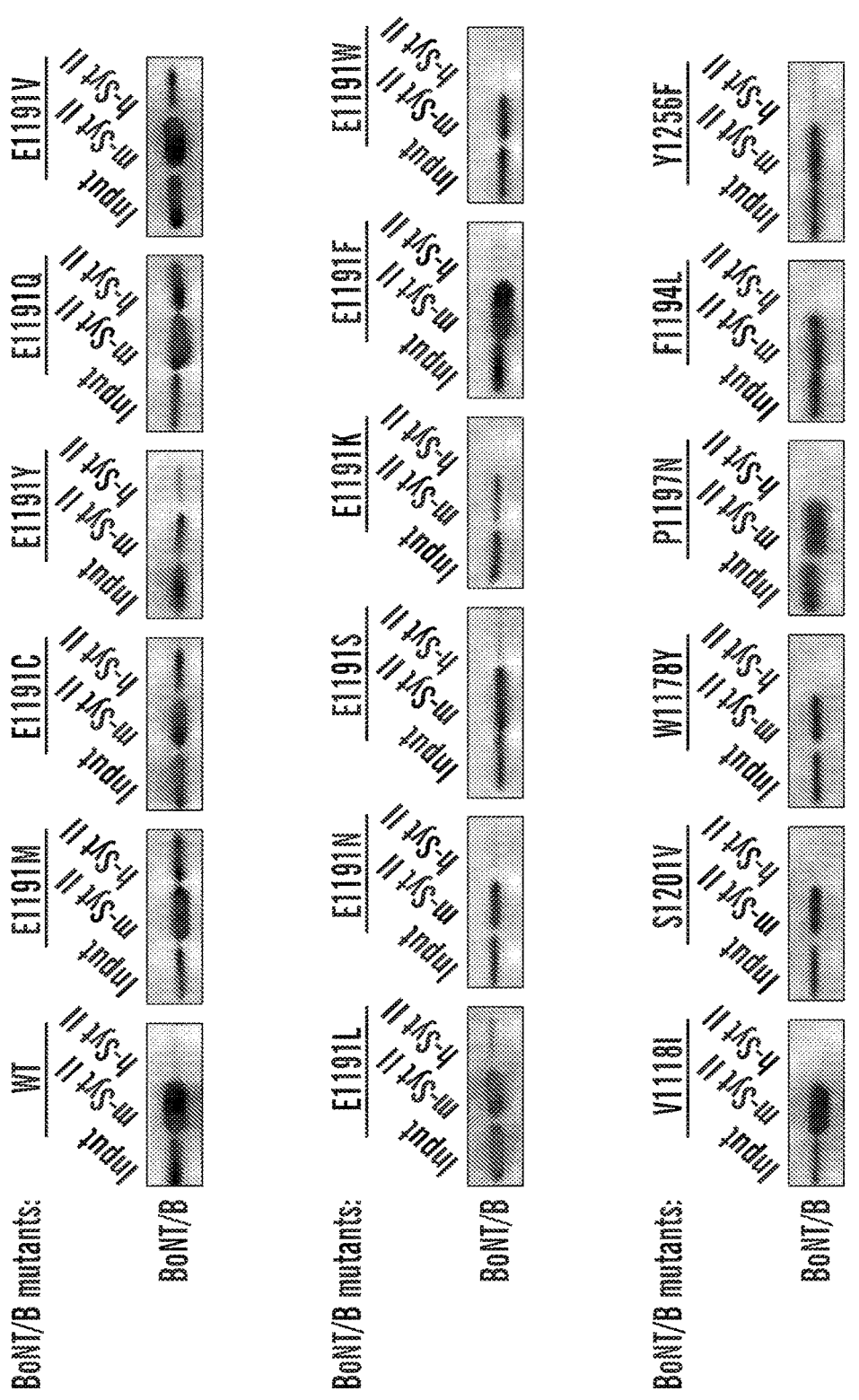

Binding of mutant BoNT/B-H$_C$ to h-Syt II was further analyzed using pull-down assay as an alternative approach (FIG. 6B). Briefly, GST-tagged mouse Syt II luminal domain (m-Syt II) and human Syt II luminal domain (h-Syt II) were immobilized on GST beads and were used to pull down mutant BoNT/B-H$_C$ expressed in bacteria. Binding of BoNT/B-H$_C$ to GST-tagged Syt II was detected via immunoblot analysis, detecting the HA tag fused to BoNT/B-H$_C$. As shown in FIG. 6B, E1191M/C/V/Q resulted in significant levels of binding to h-Syt II, which was consistent with the finding that these four mutations also displayed the strongest β-galactosidase activity (FIG. 6A). Together, these results indicated that E1191M/C/V/Q are four primary mutations that gain the ability to bind h-Syt II robustly.

Combinational Mutations in HCB Further Enhanced its Binding to h-Syt II

Figures 7A, 7B:
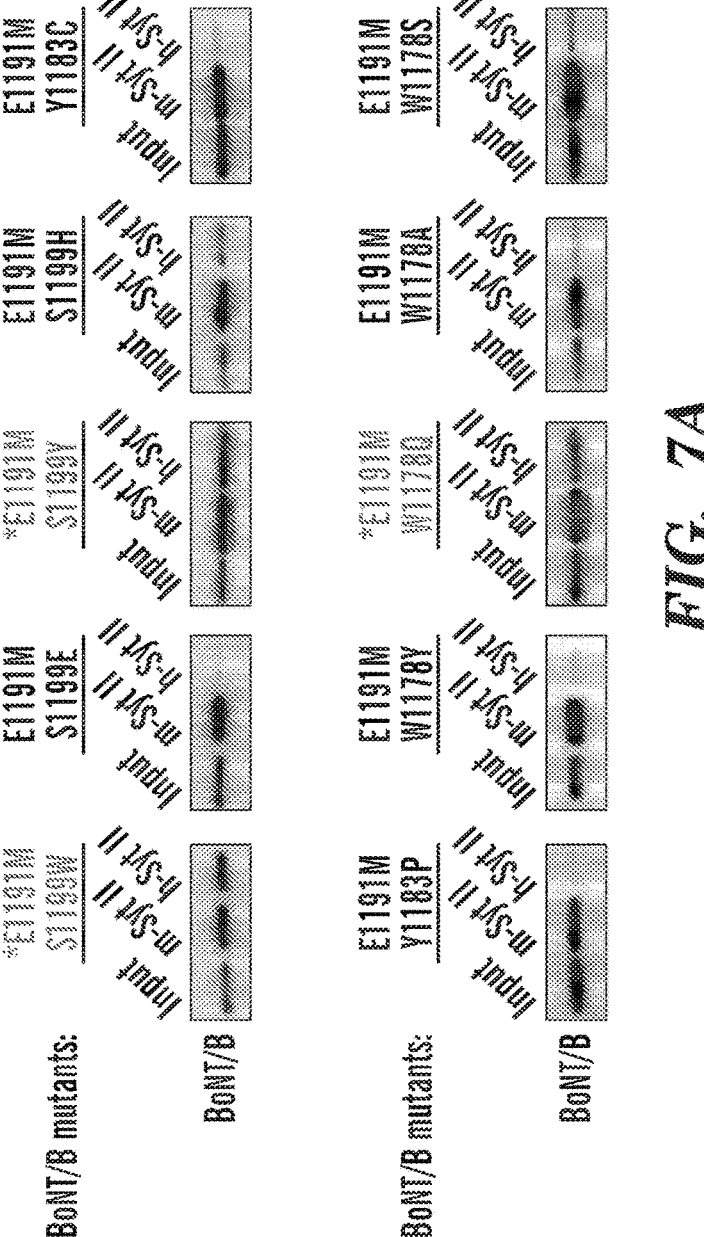
FIG. 7A-FIG. 7B shows experimental results of the screening for secondary mutations in addition to position E1191 that can enhance binding to h-Syt II.

Whether binding of BoNT/B-H$_C$ E1191M/C/V/Q to h-Syt II can be further enhanced by including a secondary mutation at a different site was then explored. The 1183, 1199, and 1178 sites were focused on as the candidates for the secondary mutation sites, as these are the only three sites that also resulted in blue colonies (FIG. 5). Using E1191M as the primary mutations, double mutations were generated combining E1191M with all other 10 residue changes identified in BACTH screening at 1183, 1199, and 1178 sites as indicated in FIG. 5B. These 10 double mutations were analyzed for their ability to bind h-Syt II in pull-down assays as indicated in FIG. 7A. Three of them, E1191M/S1199W, E1191M/S1199Y, and E1191M/W1178Q, resulted in significant binding to h-Syt II (FIG. 7A). These results suggested that including S1199W/Y and W1178Q as the secondary mutation site would further enhance binding of BoNT/B-H$_C$ E1191M/C/V/Q to h-Syt II. Together, these data indicated that there are four choices of primary mutation at E1191 site (M/C/V/Q) and three choice of secondary mutation sites (S1199W/Y and W1178Q) (FIG. 7B), and a combination of a primary mutation with a secondary mutation can further enhance binding to h-Syt II.

Combining E1191M with Y1183C/P actually reduced binding to h-Syt II (FIG. 7A). The Syt II binding interface of BoNT/B is composed of two hydrophobic pouches as previously reported, E1191 and Y1183 are located in the same pouch, while S1199 and W1178 are located in another. Because E1191 is spatially close to Y1183, a potential structural conflict may occur when mutating both of them, which may explain why double mutations at these two positions reduced binding to h-Syt II.

Determination and comparison of binding affinities between mutated BoNT/B-H$_C$ to h-Syt II quantitatively was pursued, aiming to select the double mutations with the best binding affinity. The binding affinity (K$_D$) was determined using a well-established bio-layer interferometry assay (FIG. 8A). Briefly, GST tagged Syt proteins were immobilized onto a probe. The probe was first exposed to purified BoNT/B-H$_C$ at different concentrations (association phase, FIG. 8A), followed by washing steps (dissociation phase, FIG. 8A). Binding of BoNT/B-H$_C$ to GST tagged Syt increases the total molecular weight/size on the probe, which results in a shift in light reflection at the probe that can be detected and analyzed. Binding parameters such as association constant (K$_{on}$), dissociation constant (K$_{off}$), and apparent binding affinity (K$_D$) can be calculated from the association and dissociation curve detected as indicated in FIG. 8A.

Using this assay, all combinations of four primary mutations (E1191M/C/Q/V) were systematically characterized with three secondary mutations (S1199W/Y, W1178Q). In addition, a triple mutation, E1191M/S1199W/W1178Q, was also generated and analyzed. Binding of WT BoNT/B-H$_C$ to mouse Syt II (m-Syt II) was measured as a positive control, which showed a binding K$_D$ at 0.13 μM (FIG. 8B). As expected, binding of WT BoNT/B-H$_C$ to h-Syt II was too weak to be reliably determined, with an estimated K$_D$ over the detection limit (>20 μM). A single primary mutation E1191M yielded a binding K$_D$ at 6.7 μM, a significant improvement over WT BoNT/B-H$_C$. Double mutations that combined a primary mutation site with a secondary mutation sites further improved the binding affinity to as high as 0.59 μM (E1191V/S1199Y). As expected, the majority of double mutations improved the binding affinity to h-Syt II, with K$_D$ between 0.59 μM to 4.3 μM, E1191Q/W1178Q was the only one that did not bind to h-Syt II. The reason is not known, but it is possible that this double mutation may have induced unexpected conformational changes of the protein. The triple mutation E1191M/S1199W/W1178Q showed almost the same binding affinity as the double mutation E1191M/S1199W, suggesting that adding the third mutation site may not further improve the binding affinity. Together, these data confirmed that all double mutations between E1191M/C/Q/V and S1199W/Y, W1178Q, with the exception of E11191Q/W1178Q, resulted in mutant BoNT/B-$H_C$ that can bind to h-Syt II robustly.

HCB Mutants Showed Enhanced Binding to h-Syt I

In addition to Syt II, Syt I also functions as a receptor for BoNT/B. In order to achieve the highest possible binding to human neurons, the modified BoNT/B mutants should not affect binding to human Syt I. Ideally, they may even increase binding to Syt I. Indeed, it was found that E1191M significantly enhanced binding of BoNT/B-$H_C$ to h-Syt I, as robust binding could be detected without the presence of the lipid co-receptor gangliosides (FIG. 9A). The binding affinity between selected double mutations and h-Syt I was measured using bio-layer interferometry assay. As shown in FIG. 9B, C, double mutations E1191M/S1199Y (B-$H_C$ MY) and E1191V/S1199Y (B-$H_C$ VY) displayed $K_D$ at 2.9µ M and 5.82 µM, respectively, whereas the WT BoNT/B-$H_C$ binding to h-Syt I was too weak to be reliably determined, with estimated $K_D$ over the detection limit (>20 µM).

$H_C B_{MY}$ Binds to h-Syt II on Neuronal Surfaces

Figure 10A:
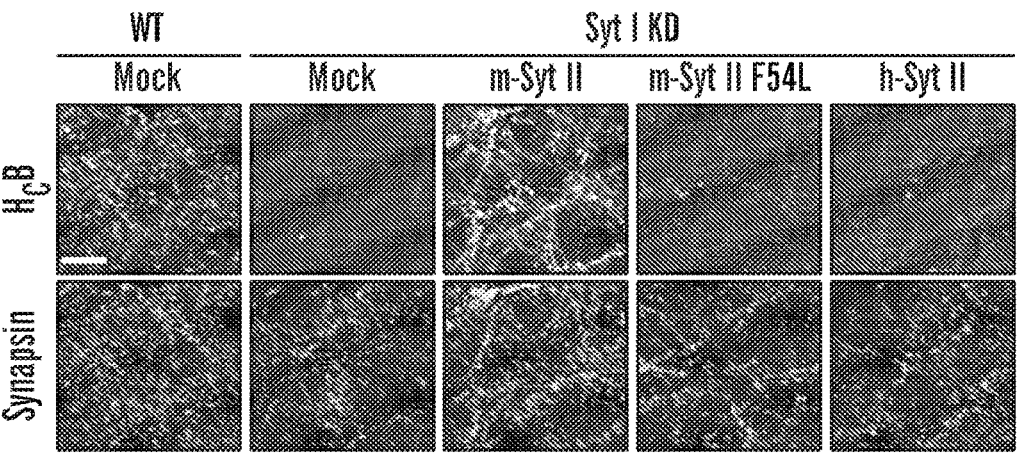
FIG. 10A-FIG. 10B are photographs of in situ immunostaining analysis indicating H$_C$B$_{MY}$ showed a robust binding to humanized neurons that express h-Syt II.
Figure 10B:
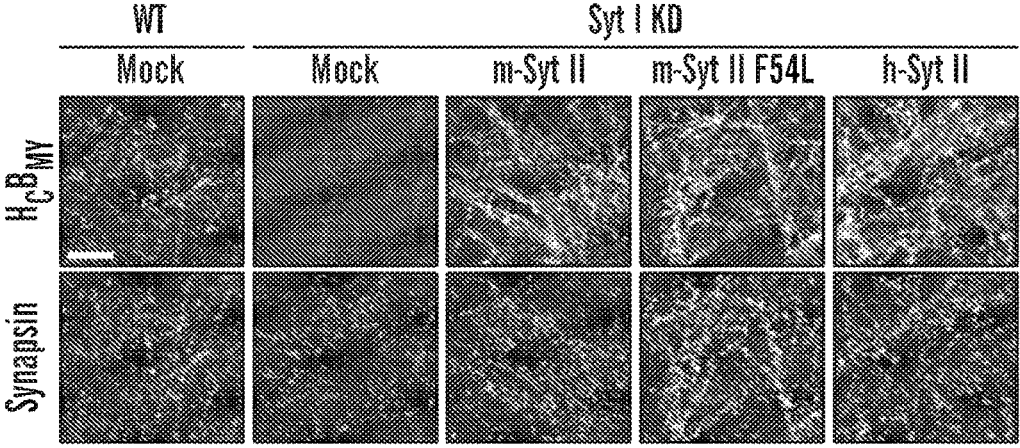

We next examined whether $H_C B_{MY}$ mutant may bind to h-Syt II on physiologically relevant neuronal surfaces. To this end, we utilized cultured rat cortical neurons as a neuron model, which expresses Syt I but not Syt II (Dong et al. The Journal of cell biology 179 (7): 1511-1522 (2007)). Thus, knocking down Syt I generated neurons with no endogenous receptors. Expressing full-length h-Syt II in these Syt I KD neurons created "humanized" neurons with only h-Syt II as the toxin receptor as we previously described (Peng et al., J Cell Sci. 125:3233-42 (2012)). As expected, WT HEB bound strongly to rat neurons and the binding was abolished after knocking down endogenous Syt I. Expression of full-length m-Syt II, but not h-Syt II nor a m-Syt II containing F54L mutation, restored binding of WT $H_C B$ (FIG. 10A). In contrast. $H_C B_{MY}$ showed robust binding to neurons that express m-Syt II, h-Syt II, or m-Syt II (F54L), demonstrating that $H_C B_{MY}$ gain the enhanced ability to bind h-Syt II on neuronal surfaces (FIG. 10B).

Figures 11A, 11B, 11C:
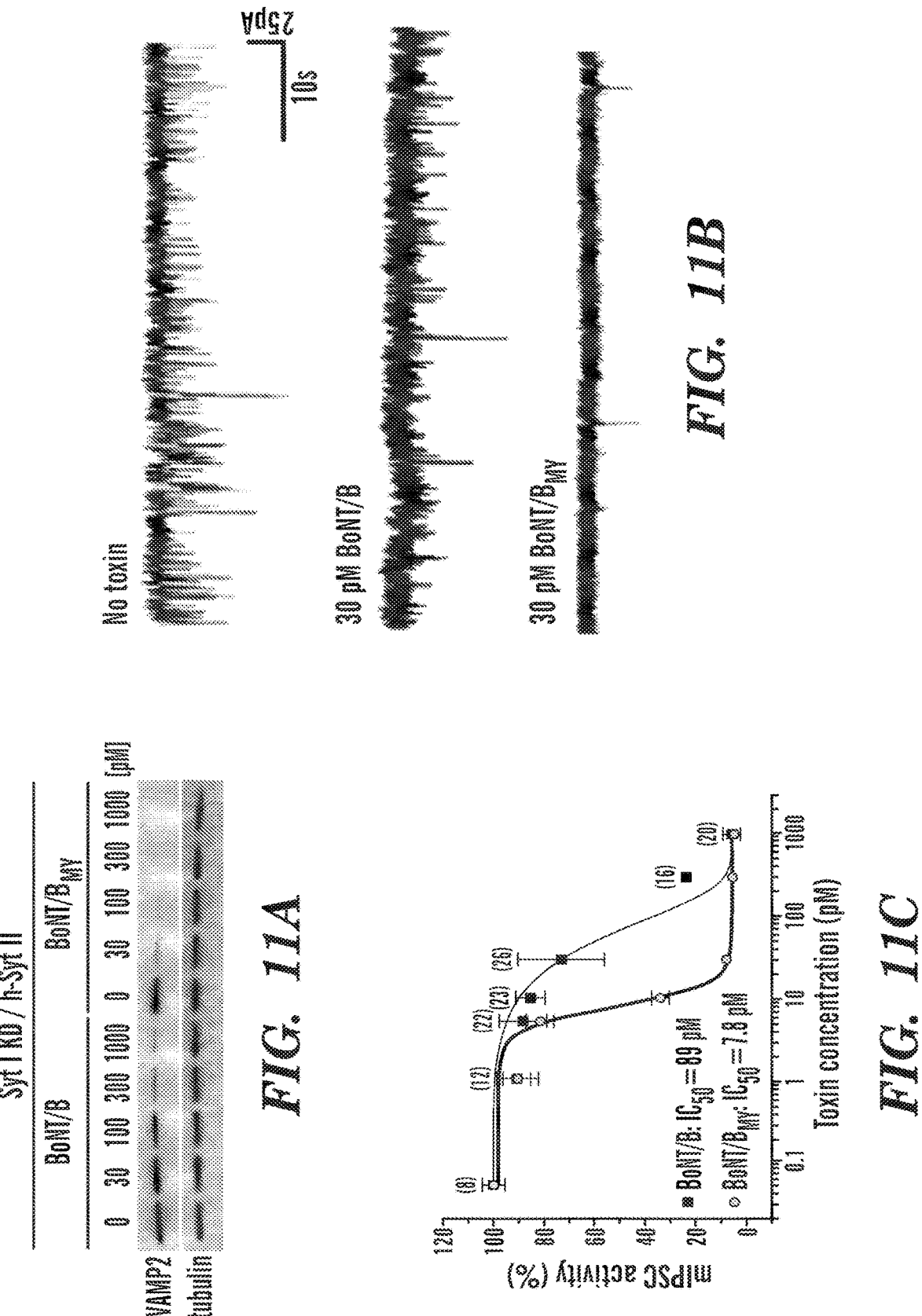
FIG. 11A-FIG. 11C are experimental results that indicate BoNT/B$_{MY}$ displayed enhanced efficacy on blocking neurotransmission in humanized neurons.

BoNT/B Mutant Displayed Enhanced Efficacy to Block Neurotransmission in Humanized Neurons To address key question whether enhanced binding to h-Syt II translates to improved efficacy at functional levels in neurons, we produced full-length WT BoNT/B and the mutant toxin containing E1191M/S1199Y point mutations (BoNT/$B_{MY}$) recombinantly in E. coli. Humanized neurons were exposed to a gradient of WT or BoNT/$B_{MY}$ toxins. Cleavage of VAMP2 was examined by immunoblotting analysis. As shown in FIG. 11A, more VAMP2 was cleaved in neurons exposed to BoNT/$B_{MY}$ compared to neurons exposed to WT BoNT/B at each toxin concentration tested, indicating that BoNT/$B_{MY}$ targeted and entered neurons more efficiently than WT toxin.

We next monitored neurotransmitter release by recording miniature inhibitory postsynaptic currents (mIPSCs) using whole-cell patch-clamp recording. The frequency of mIP-SCs reflects the activity of neurotransmitter release in a population of neurons. Entry of BoNT/B into presynaptic terminals blocks release of neurotransmitter, thus reducing frequency of mIPSCs (FIG. 11B). Humanized neurons were exposed to a gradient of WT BoNT/B or BoNT/$B_{MY}$. As shown in FIG. 11C, BoNT/$B_{MY}$ showed a greatly enhanced potency, with a half maximum inhibitory concentration ($IC_{50}$) ~11-fold lower than WT toxin: BoNT/$B_{MY}$ can achieve the same level of blockage on neurotransmitter release with 11-fold lower toxin concentrations compared to WT toxin. These data demonstrated that enhanced binding to human receptors resulted in increased efficacy of toxin at functional levels in neurons.

The BACTH method was used to screen all possible single mutations at all 19 key residues in BoNT/B-$H_C$ that form the binding pocket for Syt II. Four positions were identified that can be mutated to increase the binding affinity to h-Syt II, with E1191 site as the primary site, and S1199, W1178, and Y1183 as the secondary mutation sites. Double mutations combining the primary and secondary mutation sites, were created and tested, and showed that combining E1191M/C/V/Q with S1199Y/W or W1178Q yield double mutations with strong binding affinity to h-Syt II and h-Syt I.

DISCUSSION

By combining rationale design based on available co-crystal structure of the BoNT/B-Syt II complex with the BACTH method that saturates all possible single point mutations at each of the selected target residues, a series of point mutations in BoNT/B was identified that can bind to h-Syt II. These point mutations were further examined in combinations, revealing double mutants that gained high-affinity binding to h-Syt II. Importantly, full-length BoNT/B containing the designed mutation showed ~11-fold higher potency than WT BoNT/B on humanized neurons, demonstrating that enhanced binding to toxin receptors translates to higher potency at functional levels in neurons.

Materials and Methods

Materials and constructs. The following antibodies were purchased from indicated vendors: Synapsin I (Clone 46.1, Synaptic Systems), VAMP2 (Clone 69.1, Synaptic Systems), HA (16B12, Covance®, and β-tubulin III (ab18207, Abcam®). Bovine mixed brain gangliosides were purchased from Matreya LLC (Pleasant Gap, PA) and were reconstituted in Tris-buffered saline (TBS: 20 mM Tris, 150 mM NaCl) as previously described (Peng et al., PLOS pathogens 7 (3): e1002008 (2011)). The cDNA encoding $H_C B$ (residue 857-1291, Genbank®: ACA46990.1) was codon optimized for E. coli expression and synthesized by Genscript® Inc. (New Brunswick, NJ). The following cDNAs were generously provided by indicated groups: rat Syt I (T. C. Sudhof, Palo Alto, CA), mouse Syt II (M. Fukuda, Ibaraki, Japan), human Syt I (R. B. Sutton, Lubbock, TX). DNA encoding $H_C B$ was subcloned into pET28a vector, with both a His6 tag (SEQ ID NO: 13) and a HA tag (YPYDVPDYA (SEQ ID NO: 12)) fused to its N-terminus. Mutations in $H_C B$ were generated via PCR using Site-directed Mutagenesis Kit (Agilent Technologies®, CA), GST tagged Syt I/II fragments and Syt II F54L mutant were described previously (Dong M, et al. The Journal of cell biology 162 (7): 1293-1303 (2003); Peng et al., J Cell Sci. 125:3233-42 (2012); Dong M, et al. Science 312 (5773): 592-596 (2006)).

BACTH (bacterial adenylate cyclase two-hybrid assay): The BACTH assay was performed according to the manufacturer's instruction (Euromedex). Two compatible plasmids, pUT18C and pKT25 were selected for the screen. H-Syt II luminal domain (residues 1-80) was cloned into pKT25 to generate pKT25-h-Syt II. HCB was cloned in pUT18C for producing T18-HCB. HCB mutant libraries were created with primers containing random nucleotide triplets (NNN) at designated positions. Each library was co-transformed with the pKT25-h-Syt II plasmid into *E. coli* indicator strain BTH101 by electroporation and screened on LB agar plates containing 100 µg/ml Ampicillin, 50 µg/ml Kanamycin, 0.5 mM IPTG, and 40 µg/ml X-Gal. The plates were incubated at 30° C. for 64 hours. Plasmids were extracted from blue colonies and sequenced. The total colony number determined the possibility of covering all 20 amino acids at the selected mutation site. This was calculated by Clark-Carbon equation: P=1-(1-f) \, where f reflects the number of possible residues (f=1/20 here as there are 20 different amino acids), and N is the total number of colonies. With a minimal number of 380 colonies in the assays, the probability of covering all 20) amino acids at each position is >99.8%.

β-Galactosidase assay; *E. coli* BTH101 cells with expressed proteins of interest were inoculated into liquid LB medium containing ampicillin, kanamycin, and IPTG (0.5 mM). The culture was grown overnight at 37° C. to reach the stationary phase. The $OD_{600}$ of the culture grown overnight was recorded before harvesting. One milliliter of the culture grown overnight was centrifuged, and cell pellets were washed twice with PBS and suspended in an equal volume of Z buffer (60) mM Na2HPO4, 40 mM $Na_2HPO_4$, 10 mM KCl, 1 mM $MgSO_4$, and 20 mM dithiothreitol [DTT]). One hundred microliters of resuspended bacterial cells was diluted in 1 ml of Z buffer (dilution factor [DF]=10). Afterwards, 100 ml of chloroform and 50 ml of 0.1% SDS were added and mixed well to permeabilize the cells. Two hundred fifty microliters of the mixture was then transferred into a new Microfuge tube and brought to 28° C. 50 ml of pre-warmed o-nitrophenyl-β-galactoside (4 mg/ml in Z buffer) was added, and the mixture was incubated at 28° C. until a yellow color developed. The reaction was stopped by addition of 200 ml of 1 M $Na_2CO_3$. The A420 and the precise time period of the reaction in minutes (T) were recorded. β-galactosidase activity was defined as (1000× $A_{420}$×DF)/(T×$OD_{600}$) in Miller units.

Protein expression and purification: WT and mutants of BoNT/B-$H_C$ were expressed as His6 tagged recombinant proteins ("His6" disclosed as SEQ ID NO: 13) in *E. coli*. Syt I/II fragments and mutants were expressed as GST tagged recombinant proteins in *E. coli*. Both GST-fusion and $His_6$-fusion proteins ("$His_6$" disclosed as SEQ ID NO: 13) were purified as previously described[9], with the induction temperature at 20° C. overnight with 0.25 mM IPTG.

GST pull-down assays: Two types of pull-down assays were carried out. The first series were used to screen binding of mutant BoNT/B-$H_C$ to GST-tagged mouse Syt II (m-Syt II) and a mutant mouse Syt II (F54L) that mimicking human Syt II sequence (designated as h-Syt II). Briefly, 6 ml of *E. coli* expressing BoNT/B $H_C$ were spin down, re-suspended in 800 µl TBS, sonicated, and then incubated with 2% Triton X-100 for 1 hr at 4° C. Samples were then spun down at maximal speed for 15 min in a microcentrifuge at 4° C. The supernatants were collected and were used for pull-down assays by incubating with 10 µg of Syt proteins immobilized on glutathione-Sepharose beads (GE bioscience, Piscataway, NJ) at 4° C. for 1 hr. Samples were washed three times in washing buffer (TBS with 0.5% Triton X-100), and analyzed by immunoblotting BoNT/B-$H_C$ using the anti-HA antibody. For mutants with enhanced binding to h-Syt II, further pull-down assays were carried out by purifying these BoNT/B-$H_C$ mutants as His6 tagged proteins ("His6" disclosed as SEQ ID NO: 13) as described previously.[9]. Pull-down assays were then carried out using immobilized Syt fragments in 100 µl TBS buffer plus 0.5% Triton X-100, with or without gangliosides (60) µg/ml), for 1 hr at 4° C.

Beads were washed three times using TBS buffer plus 0.5% Triton X-100. Ten percent of bound materials were subjected to SDS-PAGE followed immunoblot analysis.

Biolayer interferometry assay. The binding affinities between $H_C$B variants and Syt I/Syt II were measured by BLI assay with the Blitz system (ForteBio®). Briefly, the GST-tagged Syt I or Syt II (20 µg/ml) were immobilized onto Dip and Read™ Anti-GST Biosensors (ForteBio®) and balanced with PBS buffer. The biosensors were then exposed to series concentrations of $H_C$B, followed by washing with PBS. Binding affinities ($K_D$) were calculated using the Blitz system software following manufacture's instruction (ForteBio®).

Neuron culture, lentivirus, and toxin binding/entry assay. Rat cortical neurons were prepared from E18-19 embryos as described previously (Peng et al. PLoS pathogens 7 (3): e1002008 (2011)). Constructs for Syt I KD, mSyt II, and h-Syt II expression in neurons was previously described (Peng et al., J Cell Sci. 125:3233-42 (2012)). Lentiviruses were added to neuron cultures at DIV5 (days in vitro), and toxin binding/entry experiments were carried out on DIV12-14. Toxins were diluted in high $K^+$ buffer (87 mM NaCl, 56 mM KCl, 1.5 mM $KH_2PO_4$, 8 mM $Na_2HPO_4$, 0.5 mM $MgCl_2$, and 1 mM CaCl) and pre-warmed to 37° C. Neurons were exposed to above toxin-containing buffers for 5 minutes at 37° C. followed by washing with PBS. These neurons were either subjected to immunostaining analysis, or incubated in toxin-free medium for additional 24 hours, followed by immunoblotting analysis.

mIPSC recording. Whole-cell patch-clamp recordings were made from DIV 14-18 cultured cortical neurons (DIV 14-18). The pipette solution contained (in mM): 135 CsCl, 10 HEPES, 1 EGTA, 1 Na-GTP, 4 Mg-ATP and 10 QX-314 (pH 7.4, adjusted with CsOH). The resistance of pipettes filled with intracellular solution varied between 4 and 5 MΩ. After formation of the whole-cell configuration and equilibration of the intracellular pipette solution, the series resistance was adjusted to 10 MΩ. Synaptic currents were monitored with an EPC-10/2 amplifier (HEKA) at −70 mV holding potential. The bath solution contained (in mM): 140 NaCl, 5 KCl, 2 CaCl, 1 MgCl2, 10 HEPES, 10 glucose (pH 7.4, adjusted with NaOH). Spontaneous inhibitory postsynaptic currents (sIPSCs) and evoked inhibitory postsynaptic currents (eIPSCs) were pharmacologically inhibited by adding AMPA and NMDA receptor blockers CNQX and APV to the extracellular bath solution. Spontaneous miniature inhibitory postsynaptic currents (mIPSCs) were monitored in the presence of tetrodotoxin (TTX) to block action potentials. Data were analyzed using Clampfit 10 (Molecular Devices R), Origin8 software (Mocrocal Inc.), Mini-Analysis software (Synaptosoft), and Igor (Wavemetrics). Statistical analysis was performed with Student's t-test (*P<0.01). All data shown are means±S.E.M.s.

CONCLUSION

The above-presented results indicate new methods and compositions to improve binding of BoNT/B to its human receptors, and provide a way to create new generations of therapeutic BoNTs, by utilizing the modified receptor binding domain created in the present invention, with improved efficacy and specificity to target human neurons than the currently utilized WT BoNTs.

These efforts show that modifying the protein sequence of BoNT/B-$H_C$ can create new versions that can bind human Syt II with high-affinity. Modification of the BoNT/B-$H_C$ protein sequence can be performed by either targeted mutagenesis (site-directed mutagenesis) or random mutagenesis of each amino acid residue within the region known for binding Syt I/II. These Syt binding regions are well defined by previous co-crystal structural studies[25,26] For instance, it composes of residues 1078-1291 in BoNT/B1 sequence (GenBank® access No.: P10844). Although these studies were performed using BoNT/B1 sequence, all subtypes of BoNT/B can be used as the template to re-create the same or similar mutations as described here. Although the exact position for selected residues may not be identical in different BoNT/B subtypes, the analogous residues in the different BoNT/B subtypes can be easily identified (e.g., by sequence alignment when not at exactly the same position).

Specifically studied were all residues in the Syt II binding interface of BoNT/B based on reported BoNT/B-Syt II complex structure (PDB ID: 2NM1), including K1113, D1115, S1116, P1117, V1118, W1178, Y1181, Y1183, E1191, K1192, F1194, A1196, P1197, S1199, S1201, E1203, F1204, E1245, and Y1256, as listed in FIG. 3B.

Mutagenesis is a common laboratory technique to create engineered protein products. Several methods to introduce mutations, including site-directed mutagenesis, random mutagenesis, combinatorial mutagenesis, and insertional mutagenesis, are available. Site-directed mutagenesis and random mutagenesis were applied to introduce mutations into BoNT/B-$H_C$ sequence. Random mutagenesis is a powerful tool to create mutant libraries for screening. By using PCR primers with doped nucleotides, a pool of mutants was created containing substitutions to all other 19 amino acids at the positions listed in FIG. 3B. The screening was then performed using BACTH system as illustrated in FIG. 4.

Residues at position 1191, 1178, 1183, and 1199 were identified as important for substitution mutations to generate BoNT/B-$H_C$ mutants with enhanced binding to human Syt II. The specific substitutions were E1191M/C/V/Q/L/Y, Y1183C/P, S1199Y/W/E/H. W1178Y/Q/A/S (FIG. 5A, B).

Further quantitative assays revealed that changing residue E1991 to M/C/V/Q resulted in the strongest binding to h-Syt II, as measured by β-galactosidase activity (Figure (A) and pull-down assays (FIG. 6B). Therefore, E1191 was identified as the primary site to introduce mutations that enhance binding to h-Syt II, and substitution mutations of E1191/M/C/V/Q were identified as the primary mutations.

E1191M was used as the primary mutation to explore whether adding a secondary mutation can further enhance binding to h-Syt II (FIG. 7A). Because Y1183C/P, S1199Y/W/E/H, and W1178Y/Q/A/S substitution mutations resulted in "light blue" colonies in BACTH screening (FIG. 5B), these sites were selected as the potential secondary mutation site. Double mutations combining E1191M with these potential secondary mutations were generated and tested. Three mutations, S1199W, S1199Y, and W1178Q were found to enhance binding to h-Syt II, when combined with the primary mutation at E1191M in pull-down assays (FIG. 7A, B). These three substitution mutations were selected as secondary mutations.

Further quantitative assays were carried out to determine the binding affinity between BoNT/B-$H_C$ mutants and h-Syt II, using bio-layer interferometry assay as described in FIG. 8A. Double mutations, with one from primary mutations (M1191M/C/Q/V) and the other from secondary mutations (S1199W/Y, W1178Q), were measured for their binding affinities to h-Syt II (FIG. 8B). The results showed that the following double mutations: E1191M/C/Q/V combined with S1199W/Y, and E1191M/C/V combined with W1178Q have significantly enhanced binding affinities for h-Syt II (FIG.

8B). These eleven double combinations were thus identified as mutations in BoNT/B-$H_C$ that enhance binding to h-Syt II the most.

Engineered BoNT/B-$H_C$ mutants were found not only enhance binding to human Syt II, but also to human Syt I, E1191M/S1199Y and E1191V/S1199Y were used to show that these mutants displayed significantly enhanced binding abilities to human Syt I as well as compared to WT BoNT/B-$H_C$ (FIG. 9).

The modified BoNT/B-$H_C$ mutants may contain amino acids substitutions at one or combinations of the amino acid residues E1191, Y1183, W1178 and S1199 such as E1191M/S1199W, E1191M/S1199Y, E1191M/W1178Q, E1191C/S1199W. E1191C/S1199Y, E1191C/W1178Q, E1191Q/S1199W, E1191Q/S1199Y, E1191V/S1199W, E1191V/S1199Y, and E1191V/W1178Q.

Selected triple mutations by combining mutations at E1191/S1199/W1178 sites were also tested and found to have similar binding affinity as the double mutation at E1191/S1199 sites. For instance, E1191M/S1199W/W1178Q has a similar binding affinity as E1191M/S1199W (FIG. 8B). Therefore, triple mutations exhibited the enhanced binding affinity of the double mutations, although they did not seem to offer significant advantage over double mutations with respect to increased binding affinity.

These results indicate that polypeptides containing BoNT/B-$H_C$ with modified amino acid sequence related to the sequence of WT BoNT/B-$H_C$, wherein the modified BoNT/B-$H_C$ has improved ability to bind human Syt I and II as compared to WT BoNT/B-$H_C$ can be made and used therapeutically. The polypeptides may be, for example, in the form of full-length BoNT/B mutants, truncated BoNT/B mutants or recombined proteins that contain the same amino acid substitutions within the receptor binding domain (BoNT/B-$H_C$), as described above, and also, BoNT/B subtypes with amino acid substitutions at according positions. In addition, BoNT/B subtype can be modified to bind h-Syt II by replacing the residues within their receptor binding domain that are different from BoNT/B1.

The full-length BoNT/B mutants encompassed contain amino acids substitutions at one or combinations (e.g., 2 or 3) of the amino acid residues E1191, Y1183, W1178 and S1199 such as E1191M/S1199W, E1191M/S1199Y, E1191M/W1178Q, E1191C/S1199W, E1191C/S1199Y, E1191C/W1178Q, E1191Q/S1199W, E1191Q/S1199Y, E1191V/S1199W, E1191V/S1199Y, and E1191V/W1178Q. The mutations can be made in the same manner as disclosed above for BoNT/B-$H_C$, using any one of BoNT/B subtypes as templates. These mutated BoNT/B toxins gain enhanced binding to both human Syt II and human Syt I, therefore will achieve higher efficacy and specificity to target human neurons than WT BoNT/B.

REFERENCES FOR THE EXAMPLES SECTION

1. Schiavo, G., Matteoli, M. & Montecucco, C. Neurotoxins affecting neuroexocytosis. *Physiol Rev* 80, 717-766 (2000).
2. Johnson, E. A. Clostridial toxins as therapeutic agents: benefits of nature's most toxic proteins. *Annu Rev Microbiol* 53, 551-575 (1999).
3. Aoki, K. R. Botulinum toxin: a successful therapeutic protein. *Curr Med Chem* 11, 3085-3092 (2004).
4. Montecucco, C. & Molgo, J. Botulinal neurotoxins: revival of an old killer. *Curr Opin Pharmacol* 5, 274-279 (2005).

5. Lange, O., et al. Neutralizing antibodies and secondary therapy failure after treatment with botulinum toxin type A: much ado about nothing? *Clin Neuropharmacol* 32, 213-218 (2009).

6. Chapman, M. A., Barron, R., Tanis, D. C., Gill, C. E. & Charles, P. D. Comparison of botulinum neurotoxin preparations for the treatment of cervical dystonia. *Clin Ther* 29, 1325-1337 (2007).

7. Cote, T. R., Mohan, A. K., Polder, J. A., Walton, M. K. & Braun, M. M. Botulinum toxin type A injections: adverse events reported to the US Food and Drug Administration in therapeutic and cosmetic cases. *J Am Acad Dermatol* 53, 407-415 (2005).

8. Dong, M., Tepp, W. H., Liu, H., Johnson, E. A. & Chapman, E. R. Mechanism of botulinum neurotoxin B and G entry into hippocampal neurons. *J Cell Biol* 179, 1511-1522 (2007).

9. Peng, L., Tepp, W. H., Johnson, E. A. & Dong, M. Botulinum neurotoxin D uses synaptic vesicle protein SV2 and gangliosides as receptors. *PLOS* Pathog 7, e1002008 (2011).

10. Dong, M., et al. Synaptotagmins I and II mediate entry of botulinum neurotoxin B into cells. *J Cell Biol* 162, 1293-1303 (2003).

11. Nishiki, T., et al. Identification of protein receptor for *Clostridium botulinum* type B neurotoxin in rat brain synaptosomes. *J Biol Chem* 269, 10498-10503 (1994).

12. Rummel, A., Karnath, T., Henke, T., Bigalke, H. & Binz, T. Synaptotagmins I and II act as nerve cell receptors for botulinum neurotoxin G. *J Biol Chem* 279, 30865-30870 (2004).

13. Peng, L., et al. Botulinum neurotoxin D-C uses synaptotagmin I/II as receptors and human synaptotagmin II is not an effective receptor for type B, D-C, and G toxins. *J Cell Sci* (2012).

14. Montecucco, C. How do tetanus and botulinum toxins bind to neuronal membranes? *TIBS*, 314-317 (1986).

15. Nishiki, T., et al. The high-affinity binding of *Clostridium botulinum* type B neurotoxin to synaptotagmin II associated with gangliosides GT1b/GD1a. *FEBS Lett* 378, 253-257 (1996).

16. Pang, Z. P., et al. Synaptotagmin-2 is essential for survival and contributes to Ca2+ triggering of neurotransmitter release in central and neuromuscular synapses. *J Neurosci* 26, 13493-13504 (2006).

17. Strotmeier, J., Willjes, G., Binz, T. & Rummel, A. Human synaptotagmin-II is not a high affinity receptor for botulinum neurotoxin B and G: increased therapeutic dosage and immunogenicity. *FEBS Lett* 586, 310-313 (2012).

18. Craxton, M. A manual collection of Syt, Esyt, Rph3a, Rph3al, Doc2, and Dblc2 genes from 46 metazoan genomes—an open access resource for neuroscience and evolutionary biology. *BMC Genomics* 11, 37 (2010).

19. Brin, M. F., et al. Safety and efficacy of NeuroBloc (botulinum toxin type B) in type A-resistant cervical dystonia. *Neurology* 53, 1431-1438 (1999).

20. Pappert, E. J. & Germanson, T. Botulinum toxin type B vs. type A in toxin-naive patients with cervical dystonia: Randomized, double-blind, noninferiority trial. *Mov Disord* 23, 510-517 (2008).

21. Wang, J., et al. Longer-acting and highly potent chimaeric inhibitors of excessive exocytosis created with domains from botulinum neurotoxin A and B. *Biochem J* 444, 59-67 (2012).

22. Rummel, A., Mahrhold, S., Bigalke, H. & Binz, T. Exchange of the H (CC) domain mediating double receptor recognition improves the pharmacodynamic properties of botulinum neurotoxin. *FEBS J* 278, 4506-4515 (2011).

23. Dong, M., et al. SV2 is the protein receptor for botulinum neurotoxin A. *Science* 312, 592-596 (2006).

24. Arnon, S. S., et al. Botulinum toxin as a biological weapon: medical and public health management. *Jama* 285, 1059-1070 (2001).

25. Jin, R., Rummel, A., Binz, T. & Brunger, A. T. Botulinum neurotoxin B recognizes its protein receptor with high affinity and specificity. *Nature* 444, 1092-1095 (2006).

26. Chai, Q., et al. Structural basis of cell surface receptor recognition by botulinum neurotoxin B. *Nature* 444, 1096-1100 (2006).

The invention claimed is:

1. A nucleic acid comprising a nucleotide sequence that encodes a polypeptide comprising a modified receptor binding domain of *Clostridial botulinum* serotype B (B-Hc), wherein the modified B-Hc comprises two or more amino acid substitutions relative to a reference wild type receptor binding domain of a *C. botulinum* serotype B, strain 1 as found in SEQ ID NO: 5, wherein the two or more amino acid substitutions are at positions selected from the group consisting of E1191, S1199, W1178, Y1183, and combinations thereof, wherein:

the substitution at position E1191 is E1191A;

the substitution at position S1199 is selected from the group consisting of S1199W, S1199E, and S1199H;

the substitution at position W1178 is selected from the group consisting of W1178Y, W1178Q, W1178A, and W1178S; and the substitution at position Y1183 is selected from the group consisting of Y1183C, and Y1183P, and wherein the polypeptide is characterized by enhanced binding to human Syt II as compared to that observed with the reference wild type receptor binding domain.

2. The nucleic acid of claim 1, wherein the polypeptide that it encodes comprises:

i) the modified B-Hc possesses 95% or more amino acid sequence identity to the reference wild type receptor binding domain;

ii) the modified B-Hc corresponds to residues 1078-1291 of SEQ ID NO: 5 or residues 859-1291 of SEQ ID NO: 5;

iii) the modified B-$H_c$ is of strain 1; or iv) a combination thereof.

3. The nucleic acid of claim 1, wherein the polypeptide that it encodes is a botulinum neurotoxin (BoNT) polypeptide comprising:

a) a protease domain;

b) a protease cleavage site;

c) a translocation domain; and d) the modified B-Hc.

4. The nucleic acid of claim 3, wherein the protease domain, translocation domain, and protease cleavage site are from serotype selected from the group consisting of A, B, C, D, E, F, G, and combinations thereof.

5. The nucleic acid claim 4, wherein the protease domain, translocation domain, and protease cleavage site are from serotype B, strain 1 or from serotype A, strain 1.

6. The nucleic acid of claim 1, wherein the modified B-Hc comprises two substitution mutations substitutions.

7. The nucleic acid of claim 6, wherein that the modified B-Hc comprises two substitutions that correspond to:

E1191M and S1199E;

E1191M and S1199H;

E1191M and W1178Y;

E1191M and W1178A;

E1191M and W1178S;

E1191M and Y1183C; or

E1191M and Y1183P.

8. The nucleic acid of claim 1, wherein the modified B-Hc comprises two or more substitutions, wherein one of the substitutions is selected from the group consisting of E1191C, E1191V, and E1191Y.

9. The nucleic acid of claim 1, wherein the modified B-Hc comprises three substitutions.

10. The nucleic acid of claim 9, wherein the three substitutions are at positions that correspond to:

E1191, Y1183 and S1199; or

E1191, S1199 and W1178.

11. The nucleic acid of claim 9, wherein the three substitutions are E1191M, S1199W and W1178Q.

12. A nucleic acid vector comprising the nucleic acid of claim 1.

13. A cell comprising the nucleic acid of claim 1.

* * * * *